(12) United States Patent
Mikhailine et al.

(10) Patent No.: US 9,597,673 B2
(45) Date of Patent: Mar. 21, 2017

(54) IRON CATALYSTS WITH UNSYMMETRICAL PNN'P LIGANDS

(71) Applicant: THE GOVERNING COUNCIL OF THE UNIVERSITY OF TORONTO, Toronto (CA)

(72) Inventors: Alexandre Mikhailine, Keswick (CA); Robert H. Morris, Toronto (CA); Paraskevi Olympia Lagaditis, Richmond (CA); Weiwei Zuo, Jiangsu (CN)

(73) Assignee: The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 14/403,770

(22) PCT Filed: May 27, 2013

(86) PCT No.: PCT/CA2013/050405
§ 371 (c)(1),
(2) Date: Nov. 25, 2014

(87) PCT Pub. No.: WO2013/173930
PCT Pub. Date: Nov. 28, 2013

(65) Prior Publication Data
US 2015/0151289 A1 Jun. 4, 2015

Related U.S. Application Data

(60) Provisional application No. 61/651,855, filed on May 25, 2012.

(51) Int. Cl.
| | | |
|---|---|---|
| C07F 15/02 | (2006.01) | |
| C07F 9/572 | (2006.01) | |
| B01J 31/12 | (2006.01) | |
| B01J 31/22 | (2006.01) | |
| C07C 29/145 | (2006.01) | |
| C07F 9/50 | (2006.01) | |
| B01J 31/18 | (2006.01) | |
| B01J 31/20 | (2006.01) | |
| C07C 29/143 | (2006.01) | |
| C07C 311/16 | (2006.01) | |
| C07D 213/30 | (2006.01) | |
| C07D 307/42 | (2006.01) | |
| C07F 9/46 | (2006.01) | |
| C07F 19/00 | (2006.01) | |
| C25B 1/00 | (2006.01) | |

(52) U.S. Cl.
CPC ......... *B01J 31/2265* (2013.01); *B01J 31/189* (2013.01); *B01J 31/20* (2013.01); *C07C 29/143* (2013.01); *C07C 29/145* (2013.01); *C07C 311/16* (2013.01); *C07D 213/30* (2013.01); *C07D 307/42* (2013.01); *C07F 9/46* (2013.01); *C07F 9/5022* (2013.01); *C07F 15/02* (2013.01); *C07F 19/00* (2013.01); *C25B 1/003* (2013.01); *B01J 2231/643* (2013.01); *B01J 2531/0255* (2013.01); *B01J 2531/842* (2013.01); *C07B 2200/07* (2013.01)

(58) Field of Classification Search
USPC .................................... 556/16, 21; 502/155
See application file for complete search history.

(56) References Cited

U.S. PATENT DOCUMENTS

| 8,716,507 B2 * | 5/2014 | Mikhailine ........... C07C 29/141 502/155 |
| 2010/0145087 A1 | 6/2010 | Mikhailine et al. |

FOREIGN PATENT DOCUMENTS

| CA | 2642563 | 4/2010 |
| CA | 2684197 | 4/2011 |

OTHER PUBLICATIONS

Lagaditis, P.O. et al.: Low-valent ene-amido iron complexes for the asymmetric transfer hydrogenation of acetophenone without base. J. Am. Chem. Soc., vol. 133, pp. 9662-9665, 2011.*
International Search Report with Written Opinion corresponding to International Patent Application No. PCT/CA2013/050405, mailed Aug. 16, 2013.
International Preliminary Report on Patentability corresponding to International Patent Application No. PCT/CA2013/050405, completed Sep. 2, 2014.
Mikhailine et al. (Jul. 13, 2012) "The Mechanism of Efficient Asymmetric Transfer Hydrogenation of Acetophenone Using an Iron(II) Complex Containing an (S,S)-Ph$_2$PCH$_2$CH=NCHPhCHPhN=CHCH$_2$PPh$_2$ Ligand: Partial Ligand Reduction is the Key," *J. Am. Chem. Soc.* 134:12266-12280.
Mikhailine et al. (Jul. 1, 2008) "Template Syntheses of Iron(II) Complexes Containing Chiral P—N—N—P and P—N—N Ligands," *Inorganic Chemistry*. 47:6587-6589.
Prokopchuk et al. (Mar. 28, 2012) "Spectroscopic and DFT Study of Ferraaziridine Complexes Formed in the Transfer Hydrogenation of Acetophenone Catalyzed Using trans-[Fe(Co)(NcMe)(PPh$_2$C$_6$H$_4$CH=NCH$_2$—)$_2$-K$^4$P,N,N,P](BF$_4$)$_2$," *Organometallics*. 31:3056-3064.
Prokopchuk et al. (Oct. 9, 2012) "Inner-Sphere Activation, Outer-Sphere Catalysis: Theoretical Study on the Mechanism of Transfer Hydrogenation of Ketones Using Iron(II) PNNP Eneamido Complexes," *Organometallics*. 31:7375-7385.
Zuo et al. (May 26-30, 2013) "The Most Active Asymmetric Transfer Hydrogenation Iron Catalysts," In; 96th Canadian Chemistry Conference and Exhibition. Quebec City, Quebec.—Abstract Only.
Extended Search Report issued on Dec. 10, 2016, for EP 13793278.6, corresponding to PCT/CA2013/050405.

(Continued)

Primary Examiner — Charanjit Aulakh
(74) Attorney, Agent, or Firm — Lathrop & Gage LLP

(57) ABSTRACT

The present invention relates to catalytic materials for hydrogenation or asymmetric hydrogenation. In particular, the invention relates to iron (II) complexes containing unsymmetrical tetradentate diphosphine (PNN'P) ligands with two different nitrogen donor groups useful for catalytic transfer hydrogenation or asymmetric transfer hydrogenation of ketones, aldehydes and imines.

37 Claims, 9 Drawing Sheets

(56) References Cited

OTHER PUBLICATIONS

Supplementary European Search Report dated Dec. 3, 2015, for EP 13793278.6, corresponding to PCT/CA2013/050405.
Ager et al. (Feb. 2012) "Asymmetric homogeneous hydrogenations at scale," Chem. Soc. Rev. 41:3340-3380.
Anderson et al. (2006) "Concise syntheses of tridentate PNE ligands and their coordination chemistry with palladium(II) : A solution- and solid-state study," Dalton Trans. 2006:4134-4145.
Baratta et al. (2005) "Ruthenium(II) Terdentate CNN Complexes: Superlative Catalysts for the Hydrogen-Transfer Reduction of Ketones by Reversible Insertion of a Carbonyl Group into the Ru-H Bond," Angew. Chem., Int. Ed. 44:6214-6219.
Baratta et al. (2005) "2-(Aminomethyl)pyridine—Phosphine Ruthenium(II) Complexes: Novel Highly Active Transfer Hydrogenation Catalysts," Organometallics. 24:1660-1669.
Barbaro et al. (2002) "The first tridentate phosphine ligand combining planar, phosphorus and carbon chirality," Chem. Commun. 2002:2672-2673.
Bauer et al. (May 2011) "Well-Defined Bifunctional Iron Catalysts for the Hydrogenation of Ketones: Iron, the New Ruthenium," Angew. Chem. Int. Ed. 50:5798-5800.
Berlin et al. (1961) "Notes- Poly(diphenylvinylphosphine Oxide)," J. Org. Chem. 26:2537-2538.
Blaser et al. (2003) "Selective Hydrogenation for Fine Chemicals: Recent Trends and New Developments," Adv. Synth. Catal. 345:103-151.
Bogar et al. (2007) "Large-scale ruthenium- and enzyme-catalyzed dynamic kinetic resolution of (rac)-1-phenylethanol," Beilstein J. Org. Chem. 3(50) pp. 1-3.
Buchard et al. (2009) "Coordination of tetradentate X2N2 (X = P, S, O) ligands to iron(II) metal center and catalytic application in the transfer hydrogenation of ketones," Dalton Trans. 2009:1659-1667.
Carpenter et al. (Jun. 2012) "Convenient and improved protocols for the hydrogenation of esters using Ru catalysts derived from (P,P), (P,N,N) and (P,N,O) ligands," Dalton Trans. 41:10136-10140.
Casey et al. (2007) "An Efficient and Chemoselective Iron Catalyst for the Hydrogenation of Ketones," J. Am. Chem. Soc. 129:5816-5817.
Chase et al. (2007) Angew. Chem. Int. Ed. 46:9136. Corrigendum for Chase et al. (2007) "Metal-Free Catalytic Hydrogenation," Angew. Chem. Int. Ed. 46:8050-8053.
Chase et al. (2008) "Lewis acid-catalyzed hydrogenation: B(C$_6$F$_5$)$_3$-mediated reduction of imines and nitriles with H$_2$," Chem. Commun. 2008:1701-1703.
Chase et al. (2007) "Metal-Free Catalytic Hydrogenation," Angew. Chem. Int. Ed. 46:8050-8053.
Clapham et al. (2004) "Mechanisms of the H2-Hydrogenation and Transfer Hydrogenation of Polar Bonds Catalyzed by Ruthenium Hydride Complexes," Coord. Chem. Rev. 248:2201-2237.
Clarke et al. (2007) "Hydrogenation of Aldehydes, Esters, Imines, and Ketones Catalyzed by a Ruthenium Complex of a Chiral Tridentate Ligand," Organometallics 26:16-19.
Del Zotto et al. (2007) [RuCl$_2$(PPh$_3$)(PNN')] Complexes as Efficient Catalysts in Transfer Hydrogenation of Ketones Organometallics 26:5636-5642.
Diaz-Valenzuela et al. (2009) "Enantioselective Hydrogenation and Transfer Hydrogenation of Bulky Ketones Catalysed by a Ruthenium Complex of a Chiral Tridentate Ligand," Chem. Eur. J. 15:1227-1232.
Enthaler et al. (2006) "Biomimetic transfer hydrogenation of ketones with iron porphyrin catalysts," Tetrahedron Lett. 47:8095-8099.
Enthaler et al. (2006) "An Environmentally Benign Process for the Hydrogenation of Ketones with Homogeneous Iron Catalysts," Chem. Asian J. 1:598-604.
Fluckiger et al (Jun. 2011) "Iron(II)-Catalyzed Asymmetric Hydrosilylation of Acetophenone," Eur. J. Org. Chem. 23:4353-4360.

Furuta et al. (2008) "Highly efficient catalytic system for hydrosilylation of ketones with iron(II) acetate—thiophenecarboxylate," Tetrahedron Lett. 49:110-113.
Gao et al. (1996) "A Ruthenium(II) Complex with a C2-Symmetric Diphosphine/Diamine Tetradentate Ligand for Asymmetric Transfer Hydrogenation of Aromatic Ketones," Organometallics 15:1087-1089.
Gao et al. (2000) "New chiral catalysts for reduction of ketones," Chirality 12:383-388.
Genet (2003) "Asymmetric Catalytic Hydrogenation. Design of New Ru Catalysts and Chiral Ligands: From Laboratory to Industrial Applications," Acc. Chem. Res. 36:908-918.
Hashiguchi et al. (1997) "Kinetic Resolution of Racemic Secondary Alcohols by Rull-Catalyzed Hydrogen Transfer," Angew. Chem., Int. Ed. 36:288-290.
Hashiguchi et al. (1995) "Asymmetric Transfer Hydrogenation of Aromatic Ketones Catalyzed by Chiral Ruthenium(II) Complexes," J. Am. Chem. Soc. 117:7562-7563.
Ikariya et al. (2007) "Asymmetric Transfer Hydrogenation of Ketones with Bifunctional Transition Metal-Based Molecular Catalysts," Acc. Chem. Res. 40:1300-1308.
Johnson et al. (2007) "Industrial-Scale Synthesis and Applications of Asymmetric Hydrogenation Catalysts," Acc. Chem. Res. 40:1291-1299.
Junge et al. (Mar. 2011) "Homogeneous catalysis using iron complexes: recent developments in selective reductions," Chem. Commun. 47:4849-4859.
Kandepi et al. (2010) "Iron(II) Complexes Bearing Chelating Cyclopentadienyl-N-Heterocyclic Carbene Ligands as Catalysts for Hydrosilylation and Hydrogen Transfer Reactions," Organometallics. 29:2777-2782.
Lagaditis et al. (2010) "Iron Complexes for the Catalytic Transfer Hydrogenation of Acetophenone: Steric and Electronic Effects Imposed by Alkyl Substituents at Phosphorus," Inorg. Chem. 49:10057-10066.
Langer et al. (Jan. 2011) "Efficient hydrogenation of ketones catalyzed by an iron pincer complex," Angew. Chem. Int. Ed. 50:2120-2124.
Laue et al. (2001) "Continuous Application of Chemzymes in a Membrane Reactor: Asymmetric Transfer Hydrogenation of Acetophenone," Adv. Synth. Catal. 343:711-720.
Li et al. (2006) "The novel water-soluble chiral PNNP-type ligand for the enantioselective reduction of ketones in aqueous media," J. Mol. Catal. A: Chem. 258:113-117.
Li et al. (2010) "Enantioselective, Organocatalytic Reduction of Ketones using Bifunctional Thiourea-Amine Catalysts," Org. Letters. 12:1756-1759.
Malacea et al. (2010) "Asymmetric hydrosilylation, transfer hydrogenation and hydrogenation of ketones catalyzed by iridium complexes," Coord. Chem. Rev. 254:729-752.
Mancheno (Feb. 2011) "New Trends towards Well-Defined Low-Valent Iron Catalysts," Angew. Chem. Int. Ed. 50:2216-2218.
Matsuda et al. (2009) "Recent progress in biocatalysis for asymmetric oxidation and reduction," Tetrahedron: Asym. 20:513-557.
Meyer et al. (2009) "Iron(II) Complexes for the Efficient Catalytic Asymmetric Transfer Hydrogenation of Ketones," Chem. Eur. J. 15:5605-5610.
Mezzetti (2010) "Ruthenium complexes with chiral tetradentate PNNP ligands: Asymmetric catalysis from the viewpoint of inorganic chemistry," Dalton Trans. 39:7851-7869.
Mikhailine et al. (2009) "Efficient Asymmetric Transfer Hydrogenation of Ketones Catalyzed by an Iron Complex Containing a P—N—N—P Tetradentate Ligand Formed by Template Synthesis," J. Am. Chem. Soc. 131:1394-1396.
Mikhailine et al. (2010) "Effect of the Structure of the Diamine Backbone of P—N—N—P ligands in Iron(II) Complexes on Catalytic Activity in the Transfer Hydrogenation of Acetophenone," Inorg. Chem. 49:11039-11044.
Mikhailine et al. (2010) "New cyclic phosphonium salts derived from the reaction of phosphine-aldehydes with acid," Organometal. Chem. 695:1824-1830.

(56) References Cited

OTHER PUBLICATIONS

Mikhailine et al. (Aug. 2012) "Asymmetric Transfer Hydrogenation of Ketimines Using Well-Defined Iron(II)-Based Precatalysts Containing a PNNP Ligand," Org. Lett. 14:4638-4641.
Minnaard et al. (2007) "Asymmetric Hydrogenation Using Monodentate Phosphoramidite Ligands," Acc. Chem. Res. 40:1267-1277.
Mitchell et al. (2000) "An efficient method for the preparation of N,N-disubstituted 1,2-diamines," Tetrahedron Lett. 41:8431-8434.
Morris (2009) "Asymmetric hydrogenation, transfer hydrogenation and hydrosilylation of ketones catalyzed by iron complexes," Chem. Soc. Rev. 38:2282-2291.
Naik et al. (2010) "Efficient Aerobic Wacker Oxidation of Styrenes Using Palladium Bis(isonitrile) Catalysts," Chem. Eur. J. 16:1624-1628.
Naik et al. (2010) "Iron(II)—bis(isonitrile) complexes: novel catalysts in asymmetric transfer hydrogenations of aromatic and heteroaromatic ketones," Chem. Commun. 46:4475-4477.
Naud et al. (2007) "Enantioselective Ketone Hydrogenation: From R&D to Pilot Scale with Industrially Viable Ru/Phosphine—Oxazoline Complexes," Org. Process Res. Dev. 11:519-523.
Noyori et al. (2001) "Asymmetric Catalysis by Architectural and Functional Molecular Engineering: Practical Chemo- and Stereoselective Hydrogenation of Ketones," Angew. Chem., Int. Ed. 40:40-73.
Noyori et al. (1997) "Asymmetric Transfer Hydrogenation Catalyzed by Chiral Ruthenium Complexes," Acc. Chem. Res. 30:97-102.
Phillips et al. (Sep. 2011) "Exploring the role of phosphorus substituents on the enantioselectivity of Ru-catalysed ketone hydrogenation using tridentate phosphine-diamine ligands," Catal. Sci. Technol. 1:1336-1339.
Ranocchiari et al. (2009) "PNNP Macrocycles: A New Class of Ligands for Asymmetric Catalysis," Organometallics 28:1286-1288.
Ringenberg et al. (Mar. 2011) "Merging the best of two worlds: artificial metalloenzymes for enantioselective catalysis," Chem. Commun. 47:8470-8476.
Samec et al. (2006) "Mechanistic aspects of transition metal-catalyzed hydrogen transfer reactions," Chem. Soc. Rev. 35:237-248.
Sandoval et al. (2010) "Chiral $\eta^6$-Arene/N-Tosylethylenediamine—Ruthenium(II) Complexes: Solution Behavior and Catalytic Activity for Asymmetric Hydrogenation," Chem. Asian J. 5:806-816.
Servi et al. (2008) "Chemo-enzymatic deracemization methods for the preparation of enantiopure non-natural α-amino acids," Coord. Chem. Rev. 252:715-726.
Soni et al. (Feb. 2011) "The importance of the N—H bond in Ru/TsDPEN complexes for asymmetric transfer hydrogenation of ketones and imines," Org. Biomol. Chem. 9:3290-3294.
Stephan et al. (2009) "Frustrated Lewis pairs: metal-free hydrogen activation and more," Angew. Chem., Int. Ed. 49:46-76.
Stoop et al. (2000) "Ruthenium(II) Complexes with Chiral Tetradentate $P_2N_2$ Ligands Catalyze the Asymmetric Epoxidation of Olefins with $H_2O_2$," Organometallics 19:4117-4126.
Sues et al. (Jul. 2011) "Stereoelectronic Factors in Iron Catalysis: Synthesis and Characterization of Aryl-Substituted Iron(II) Carbonyl P—N—N—P Complexes and Their Use in the Asymmetric Transfer Hydrogenation of Ketones," Organometallics 30:4418-4431.
Sui-Seng et al. (2008) "Highly Efficient Catalyst Systems Using Iron Complexes with a Tetradentate PNNP Ligand for the Asymmetric Hydrogenation of Polar Bonds," Angew. Chem. Int. Ed. 47:940-943.
Takebayashi et al. (Jun. 2011) "Experimental Investigations of a Partial Ru—O Bond during the Metal—Ligand Bifunctional Addition in Noyori-Type Enantioselective Ketone Hydrogenation," J. Am. Chem. Soc. 133:9666-9669.
Takehara et al. (1993) "Amino alcohol effects on the ruthenium(II)-catalysed asymmetric transfer hydrogenation of ketones in propan-2-ol," Chem. Commun. 1996:233-234.
Thoumazet et al. (2003) "A Cationic 1-(2-Methylpyridine)Phosphole Cymene Ruthenium Chloride Complex as an Efficient Catalyst in the Transfer Hydrogenation of Ketones" Organometallics 22:1580-1581.
Wong et al. (1993) "Preparation of copper(I) binap-$P_2N_2$ complexes; crystal and molecular structure of [Cu(Binap-$P_2N_2$)Br]," Polyhedron. 12:2063-2066.
Xie et al. (Dec. 2010) "Transition Metal-Catalyzed Enantioselective Hydrogenation of Enamines and Imines," Chem. Rev. 111:1713-1760.
Zhou et al. (2010) "Enantioselective synthesis of amines: general, efficient iron-catalyzed asymmetric transfer hydrogenation of imines," Angew. Chem., Int. Ed. 49:8121-8125.
Zweifel et al. (2008) "Ethanol as hydrogen donor: highly efficient transfer hydrogenations with rhodium(I) amides," Angew. Chem., Int. Ed. 47:3245-3249.

\* cited by examiner

IRON CATALYSTS WITH UNSYMMETRICAL PNN'P LIGANDS

The present application is a U.S. National Stage application under 35 U.S.C. 371 of International Application Number PCT/CA2013/050405, filed in English on May 27, 2013, which claims the benefit of and priority to U.S. Provisional Patent Application No. 61/651,855, filed May 25, 2012. The entirety of each application is incorporated herein by reference.

FIELD OF THE INVENTION

The present invention relates to catalytic materials for hydrogenation or asymmetric hydrogenation. In particular, the invention relates to iron (II) complexes containing unsymmetrical tetradentate diphosphine (PNN'P) ligands with two different nitrogen donor groups useful for catalytic hydrogenation, including, for example, transfer hydrogenation and asymmetric transfer hydrogenation of ketones, aldehydes and imines.

BACKGROUND

The asymmetric reduction of polar unsaturated bonds allows the production of valuable chiral secondary alcohols and amines for use as chiral building blocks in industry and academia. Chiral alcohols and amines that are produced by the asymmetric hydrogenation or asymmetric transfer hydrogenation of ketones and imines, respectively, are extensively used in the synthesis of pharmaceuticals, agricultural chemicals, fragrances and materials.

In the biotechnology and pharmaceutical sectors, the ability to synthesize enantiomerically pure small molecules, amino acids, peptides and proteins is of great value. The use of a drug molecule as a single enantiomer reduces the risk of side effects, increases efficacy and accuracy of dosage, and often reduces the dosage required. Further, selective synthesis of the desired enantiomer results in a reduction in cost by reducing waste. In the agrochemical business about 25% of the members of several classes of pesticides and herbicides exist as enantiomers. Volatile, enantiomerically pure alcohols are also particularly valuable in the flavours and fragrances industries where each enantiomer provides a distinctive olfactory sensation. Single enantiomer helical molecules can also impart important optical, electronic and magnetic properties to materials and nanomaterials with applications in electronic switches, motors, sensors, polarizers and displays.

One method of carrying out an asymmetric catalytic reduction is to utilize a transition metal complex. (*Handbook of Homogeneous Hydrogenation*, de Vries, J. G., Elsevier, C. J., Eds., Wiley-VCH: Weinheim, Germany, 2007, Vol. 3, pp 1131-1163; Minnaard, A. J., Feringa, B. L., Lefort, L., de Vries, J. G. *Acc. Chem. Res.* 2007, 40, 1267-1277; Malacea, R., Poli, R., Manoury, E. *Coord. Chem. Rev.* 2010, 254, 729-752; Ikariya, T., Blacker, A. J. *Acc. Chem. Res.* 2007, 40, 1300-1308; Genet, J. P. *Acc. Chem. Res.* 2003, 36, 908-918; Noyori, R., Ohkuma, T. *Angew. Chem. Int. Ed.* 2001, 40, 40-73; *Modern Reduction Methods*, Andersson, P. G., Munslow, I. J., Eds., Wiley-VCH: Weinheim, Germany, 2008.) Another method of carrying out an asymmetric catalytic reduction is to utilize enzymes. (Ringenberg, M. R., Ward, T. R. *Chem. Commun.* 2011, 47, 8470-8476; Bogar, K.; Martin-Matute, B., Backvall, J. E. *Beilstein J. Org. Chem.* 2007, 3, No. 50; Servi, S., Tessaro, D., Pedrocchi-Fantoni, G. *Coord. Chem. Rev.* 2008, 252, 715-726; Matsuda, T., Yamanaka, R., Nakamura, K. *Tetrahedron: Asym.* 2009, 20, 513-557.)

Classical methods for the synthesis of chiral products involve the use of a reagent from the chiral pool or the resolution of a mixture of enantiomers. Both of these methods have drawbacks, including the necessity for expensive reagents, the generation of waste, and the requirement for costly work-up. Other methods including the use of organocatalysts (*Organocatalytic enantioselective reduction of olefins, ketones, and imines* Kagan, H. B., Eds. Wiley-VCH: New York, 2007; Li, D., He, A. Y., Falck, J. R. *Org. Letters* 2010, 12, 1756-1759) and other metal-free compounds (Chase, P. A., Jurca, T., Stephan, D. W. *Chem. Commun.* 2008, 1701-1703; Chase, P. A., Welch, G. C., Jurca, T., Stephan, D. W. *Angew. Chem. Int. Ed.* 2007, 46, 8050-8053; Stephan, D. W., Erker, G. *Angew. Chem. Int. Ed.* 2009, 49, 46-76.) are being developed to offer cheaper and more environmentally friendly alternatives. (Blaser, H. U., Malan, C., Pugin, B., Spindler, F., Steiner, H., Studer, M. *Adv. Synth. Catal.* 2003, 345, 103-151; Naud, F., Spindler, F., Rueggeberg, C. J., Schmidt, A. T., Blaser, H. U. *Org. Process Res. Dev.* 2007, 11, 519-523; *Asymmetric Catalysis on Industrial Scale: Challenges, Approaches and Solutions*, Blaser, H. U., Federsel, H. J., Eds., Wiley-VCH: Weinheim, Germany, 2010.)

Complexes containing platinum group metals (PGMs) such as Pt, Ru, Rh and Ir, and chiral ligands are especially active and have been developed to be highly enantioselective. (*Handbook of Homogeneous Hydrogenation* de Vries, J. G., Elsevier, C. J., Eds., Wiley-VCH: Weinheim, Germany, 2007, Vol. 3, pp 1131-1163; Malacea, R., Poli, R., Manoury, E. *Coord. Chem. Rev.* 2010, 254, 729-752; Hedberg, C. and Gladiali, S., Taras, R. In *Modern Reduction Methods* Andersson, P. G., Munslow, I. J., Eds., Wiley-VCH: Weinheim, Germany, 2008: Chapter 5-6, pp 109-152; Johnson, N. B., Lennon, I. C., Moran, P. H., Ramsden, J. A. *Acc. Chem. Res.* 2007, 40, 1291-1299; Xie, J. H.; Zhu, S. F.; Zhou, Q. L. *Chem. Rev.* 2011, 111, 1713-1760.)

The information gained from mechanistic studies on these catalytic systems greatly assists in the optimization and scaling-up of the process for industrial application (For recent reviews see: Clapham, S. E., Hadzovic, A., Morris, R. H. *Coord. Chem. Rev.* 2004, 248, 2201-2237; Samec, J. S. M., Backvall, J. E., Andersson, P. G., Brandt, P. *Chem. Soc. Rev.* 2006, 35, 237-248; Sandoval, C. A., Bie, F. S., Matsuoka, A., Yamaguchi, Y., Naka, H., Li, Y. H., Kato, K., Utsumi, N., Tsutsumi, K., Ohkuma, T., Murata, K., Noyori, R. *Chem. Asian J.* 2010, 5, 806-816; Soni, R., Cheung, F. K., Clarkson, G. C., Martins, J. E. D., Graham, M. A., Wills, M. *Org. Biomol. Chem.* 2011, 9, 3290-3294; Takebayashi, S., Dabral, N., Miskolzie, M., Bergens, S. H. *J. Am. Chem. Soc.* 2011, 133, 9666-9669; Blaser, H. U., Malan, C., Pugin, B., Spindler, F., Steiner, H., Studer, M. *Adv. Synth. Catal.* 2003, 345, 103-151; *Asymmetric Catalysis on Industrial Scale: Challenges, Approaches and Solutions* Blaser, H. U., Federsel, H. J., Eds. Wiley-VCH: Weinheim, Germany, 2010; Johnson, N. B., Lennon, I. C., Moran, P. H., Ramsden, J. A. *Acc. Chem. Res.* 2007, 40, 1291-1299; Ager, D. J.; de Vries, A. H. M.; de Vries, J. G. *Chem. Soc. Rev.* 2012, 41, 3340-3380.) However, there are some negative features of these catalytic systems, such as high cost, low availability, and high toxicity of the metal, that make them undesirable for some applications.

Recent developments to overcome these drawbacks involve the use of first row transition metals for asymmetric catalysis. Low-valent iron is an especially attractive candidate for this role, since it is inexpensive, abundant, and non-toxic in comparison to ruthenium. Iron-containing catalysts for asymmetric reduction reactions are proving to be promising. (Junge, K., Schroder, K., Beller, M. *Chem. Commun.* 2011, 47, 4849-4859; Morris, R. H. *Chem. Soc. Rev.* 2009, 38, 2282-2291; Bauer, G., Kirchner, K. A. *Angew. Chem. Int. Ed.* 2011, 50, 5798-5800; Mancheno, O. G. *Angew. Chem. Int. Ed.* 2011, 50, 2216-2218.)

A need remains for alternative iron-containing catalytic systems for direct hydrogenation (Casey, C. P., Guan, H. R. *J. Am. Chem. Soc.* 2007, 129, 5816-5817; Sui-Seng, C., Freutel, F., Lough, A. J., Morris, R. H. *Angew. Chem. Int. Ed.* 2008, 47, 940-943; Langer, R., Leitus, G., Ben-David, Y., Milstein, D. *Angew. Chem. Int. Ed.* 2011, 50, 2120-2124) and transfer hydrogenation (Mikhailine, A. A., Lough, A. J., Morris, R. H. *J. Am. Chem. Soc* 2009, 131, 1394-139; Meyer, N.; Lough, A. J., Morris, R. H. *Chem. Eur. J.* 2009, 15, 5605-5610; Morris, R. H. *Chem. Soc. Rev.* 2009, 38, 2282-2291; Lagaditis, P. O., Lough, A. J., Morris, R. H. *Inorg. Chem.* 2010, 49, 10057-10066; Mikhailine, A. A., Morris, R. H. *Inorg. Chem.* 2010, 49, 11039-11044; Lagaditis, P. O., Lough, A. J., Morris, R. H. *J. Am. Chem. Soc.* 2011, 133, 9662-9665; Sues, P. E., Lough, A. J., Morris, R. H. *Organometallics* 2011, 30, 4418-4431; Enthaler, S., Erre, G., Tse, M. K., Junge, K., Beller, M. *Tetrahedron Lett.* 2006, 47, 8095-8099; Enthaler, S., Hagemann, B., Erre, G., Junge, K., Beller, M. *Chem. Asian J.* 2006, 1, 598-604; Furuta, A., Nishiyama, H. *Tetrahedron Lett.* 2008, 49, 110-113; Buchard, A., Heuclin, H., Auffrant, A., Le Goff, X. F., Le Floch, P. *Dalton Trans.* 2009, 1659-1667; Naik, A., Maji, T., Reiser, O. *Chem. Commun.* 2010, 46, 4475-4477; Kandepi, V., Cardoso, J. M. S., Penis, E., Royo, B. *Organometallics* 2010, 29, 2777-2782) of ketone and, recently, ketimines (Zhou, S. L., Fleischer, S., Junge, K., Das, S., Addis, D., Beller, M. *Angew. Chem. Int. Ed.*, 49, 8121-8125). Such alternative systems are preferably highly reactive and selective.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

It is an object of the present invention to provide to catalytic materials and complexes that are useful for hydrogenation or asymmetric hydrogenation. It is another object of the present invention to provide iron (II) complexes containing unsymmetrical tetradentate phosphorus-nitrogen-nitrogen'-phosphorus (P—$N^1$—$N^2$—P) ligands useful for the catalytic transfer hydrogenation or asymmetric transfer hydrogenation of ketones, aldehydes and imines. The unsymmetrical structure has different groups attached to $N^1$ and $N^2$. An important example of the unsymmetrical nature is when $N^1$ is part of a secondary amine donor group with a hydrogen attached to nitrogen (M-NHRR') and $N^2$ is a negatively charged amido donor group (NRR') or the reverse where $N^1$ is the amido and $N^2$ is the amine. Another is when $N^1$ is a negatively charged amido donor group and $N^2$ is a different negatively charged amido donor group, preferably and eneamido group. The synthesis of the iron complexes by a template method results in this unsymmetrical structure naturally and also allows the ready encorporation of an enantiopure chiral (asymmetric) linking group between $N^1$ and $N^2$. Diamines are available in both the (R,R) and (S,S) forms so that both enantiomers of the complexes are easily prepared. The iron complexes also have a pi-acid ligand, typically but not restricted to a carbonyl group. These features are found to beneficial for the activity of iron catalysts for the transfer hydrogenation of substrates containing polar bonds such as C=O (e.g. ketone, aldehyde) and C=N (e.g. imine). The iron compounds with $N^1$ part of a secondary amine donor and $N^2$ part of an imine donor group or the reverse with $N^1$ as the imine and $N^2$ as the amine are useful catalyst precursor complexes.

In accordance with one aspect, there is provided a complex of formula (I)

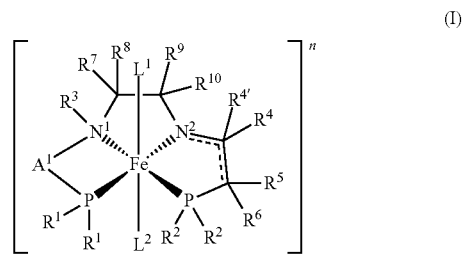

(I)

wherein:
$N^1$ and $N^2$ are nitrogen atoms;
$A^1$ is $C_{1-4}$ alkylene, optionally as part of a five or six-membered ring, or ortho-benzylene optionally as part of a six-membered ring, each of which may be optionally substituted by one or more of $C_1$-$C_{20}$ alkyl, $C_1$-$C_6$ alkoxy, halogen, or amine, wherein the five or six membered ring optionally comprises one or more heteroatom;
each $R^1$ and $R^2$ is independently $C_1$-$C_8$ alkyl, $C_2$-$C_8$ alkenyl, $C_1$-$C_8$ alkoxy, aryloxy, $C_3$-$C_8$ cycloalkyl, aryl or heteroaryl, all of which may be optionally substituted, preferably aryl such as phenyl, para-tolyl and meta-xylyl, or both $R^1$ substituents combine to form an optionally substituted $C_2$-$C_4$ linear or $C_3$-$C_8$ branched alkylene, or form a ring together with the phosphorus atom to which they are attached, and/or both $R^2$ substituents combine to form an optionally substituted $C_2$-$C_4$ linear or $C_3$-$C_8$ branched alkylene, or form a ring together with the phosphorus atom to which they are attached;
$R^3$ is H or absent;
$R^4$, $R^5$ and $R^8$ are each independently H, or $C_1$-$C_8$ alkyl, $C_2$-$C_8$ alkenyl, aryl, or cycloalkyl, each of which may be optionally substituted;
$R^{4'}$ is H or absent;
$R^6$ is H or absent;
$R^7$, $R^9$ and $R^{10}$ are each independently H, or $C_1$-$C_8$ alkyl, $C_2$-$C_8$ alkenyl, aryl, or cycloalkyl, each of which may be optionally substituted, or $R^7$ and $R^9$ together with the carbon atoms to which they are attached form an optionally substituted $C_{5-8}$ cycloalkyl ring, or $R^9$ and $R^{10}$ together with the carbon atom to which they are attached form a carbonyl group;
$L^1$ is CO, CNR, $CN^-$, N-heterocyclic carbene or NO, wherein R is $C_1$-$C_8$ alkyl, linear or branched, for example n-Bu or tert-Bu, optionally substituted with vinyl or triethoxysilane, or aryl such as phenyl, tolyl, 4-vinylphenyl, 4-alkylphenyl, all of which may be optionally substituted with vinyl, triethoxysilane or phosphinate;
$L^2$ is absent or is hydride, optionally substituted pyridine, N-methylacetamide, N-methylformamide, optionally substituted imidazole, halide, or $R^aOH$, $NCR^a$ or $^-OR^a$, wherein $R^a$ is aryl, heteroaryl, $C_1$-$C_8$ alkyl, $C_2$-$C_8$ alkenyl or $C_3$-$C_8$ cycloalkyl, all of which may be optionally substituted, or $R^b{}_3N$ wherein each $R^b$ is independently H, methyl or ethyl, or $R^c(CO)R^c$ wherein each $R^c$ is independently $C_1$-$C_8$ alkyl, aryl, or heteroaryl; and n is 0, +1, or +2, wherein when n is +1 or +2, the complex further comprises at least one non-coordinating anion Y, wherein the total charge of all non-coordinating anions in the complex is equal to −n In accordance with one embodiment, $R^3$ is H and $L^2$ is hydride, optionally substituted pyridine, N-methylacetamide, N-methylformamide, optionally substituted imidazole, halide, or $R^aOH$, $NCR^a$ or $^-OR^a$, wherein $R^a$ is aryl, heteroaryl, $C_1$-$C_8$ alkyl, $C_2$-$C_8$ alkenyl or $C_3$-$C_8$ cycloalkyl, all of which may be optionally substituted, or $R^b{}_3N$ wherein each $R^b$ is independently H, methyl or ethyl, or $R^c(CO)R^c$ wherein each Re is independently $C_1$-$C_8$ alkyl, aryl, or heteroaryl.

In accordance with one embodiment, $R^{4'}$ is H. In accordance with another embodiment, the complex further comprises at least one non-coordinating anion Y.

In accordance with another embodiment, there is provided a complex of formula (I), wherein $A^1$ is

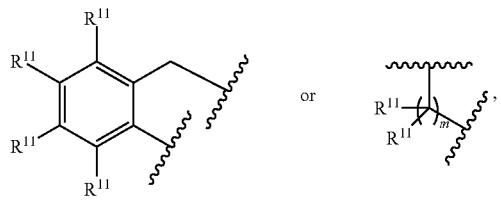

and wherein each $R^{11}$ is independently H, or optionally substituted $C_1$-$C_8$ alkyl, $C_2$-$C_8$ alkenyl, aryl, cycloalkyl, sulfonato, nitro, amino, alkoxy, carboxy, or carboxylato; and m is 1, 2, or 3.

In accordance with another embodiment, there is provided a complex having the structure of formula (II):

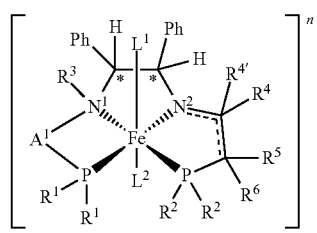

(II)

In accordance with another embodiment, there is provided a complex having the structure of formula (III):

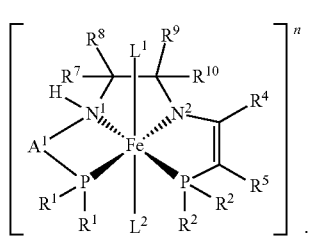

(III)

In accordance with another embodiment, there is provided a complex having the structure of formula (IV):

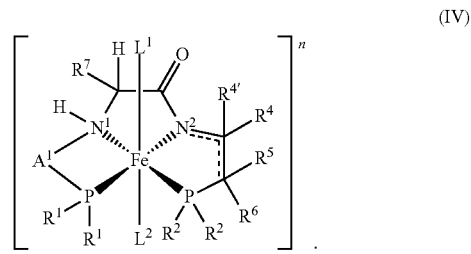

(IV)

In accordance with another embodiment, there is provided a complex having the structure of formula (IV), wherein $R^7$ is H, methyl, $NH_2$, $-CH_2CONH_2$, $-CH_2COOH$, $-CH_2SH$, $-CH_2CH_2COOH$, $-CH_2CH_2CONH_2$, $-CH_2(CH_3)_2$, $-CH_2CH(CH_3)_2$, $-CHCH_3CH_2CH_3$, $-(CH_2)NH_2$, $-CH_2Ph$, $-CH_2$-p-PhOH, $-CH_2CH_2SCH_3$, $-CH_2OH$, $-CHOHCH_3$, optionally substituted aryl,

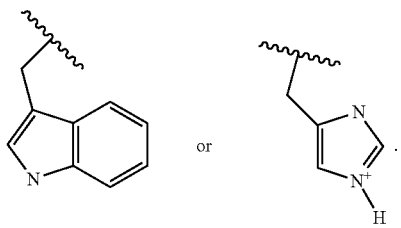 [SMILES: *Cc1c[nH]c2ccccc12 ; *Cc1c[nH+]c[nH]1]

In accordance with another embodiment, there is provided a complex having the formula of (I), (II), (III) or (IV), wherein the complex is chiral. In accordance with another aspect, the complex has (R,R) or (S,S) stereochemistry.

In accordance with another embodiment, there is provided a complex having the formula of (I), (II), (III) or (IV), wherein n is +1 or +2 and Y is $BF_4^-$, $PF_6^-$, $SbF_6^-$, $ClO_4^-$, $CH_3SO_3^-$, $CF_3SO_3^-$, $C_6H_5SO_3^-$, p-$CH_3C_6H_4SO_3^-$, $FeCl_4^{2-}$, $FeBr_4^{2-}$, phosphates, carboranes, or $B(R^d)_4^-$ or $Al(R^d)_4^-$, wherein each $R^d$ is independently an optionally substituted $C_1$-$C_6$ alkyl, aryl, phenyl, $C_6H_3(CF_3)_2$ and $C_6F_5$, halogen, pseudohalogen, $C_1$-$C_8$ alkoxide, or aryloxide. In one preferable embodiment, Y is $BPh_4^-$.

Preferred embodiments of the complex are

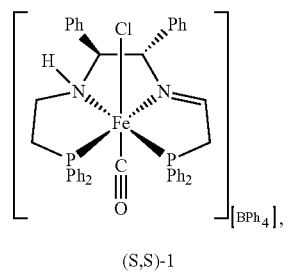

(S,S)-1

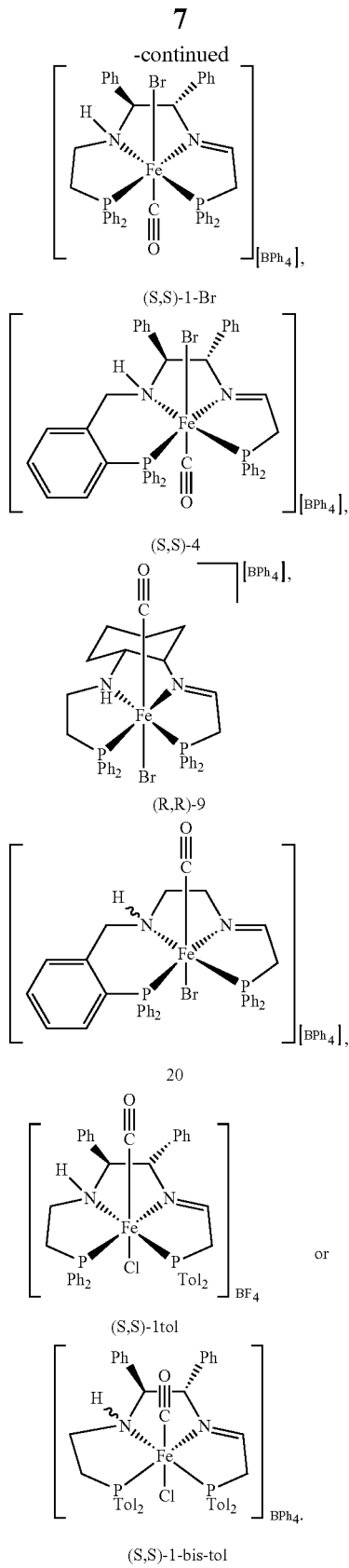

isomers of the catalyst in exactly the same fashion as described here for the (S,S) isomers. Similarly the (S,S) isomer of the diamine trans-1,2-diaminocyclohexane is commercially available and can be used to make the (S,S) isomer of catalyst 9 with exactly the same method as described for the (R,R) isomer. Diastereomers have been observed with the amine nitrogen in each of its configurations (R) or (S). Similarly diastereomers have been observed with the carbonyl group above the PNNP plane as in (R,R)-9 or below the PNNP plane as in (S,S)-1 as shown above. Exemplary, non-limiting, syntheses are described below that lead to predominately one diastereomer.

In accordance with another aspect, there is provided a use of a complex as described herein, in a transfer hydrogenation of a substrate. In accordance with one embodiment, the complex is chiral and the transfer hydrogenation is an asymmetric transfer hydrogenation. In accordance with another embodiment, the substrate is a ketone, aldehyde, or imine.

In accordance with another embodiment, the transfer hydrogenation is carried out in a two phase system.

In accordance with another aspect, there is provided a composition comprising a complex as described herein, a base and a hydrogenation substrate.

In accordance with another aspect, there is provided a composition comprising a complex as described herein and at least one additive, promoter, or additional catalyst.

In accordance with another embodiment, there is provided a composition comprising an iron complex as described herein and a support structure. In one preferred embodiment, the support structure is a polymeric support, metal support or silica support.

In accordance with another aspect of the present application, there is provided a process for the preparation of the complex of formula (I), the process comprising the step of reducing one imine group in a diimine complex of formula (X)

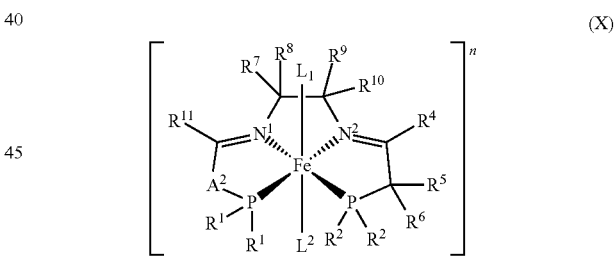

where substituents $R^1$, $R^2$ and $R^4$-$R^{10}$ are the same as defined above, $R^{11}$ is H, or optionally substituted $C_1$-$C_8$ alkyl, $C_2$-$C_8$ alkenyl, aryl, cycloalkyl, sulfonato, nitro, amino, alkoxy, carboxy, or carboxylato, and $A^2$ is $C_{1-3}$ alkylene, optionally as part of a five or six-membered ring together with $R^{11}$ and the carbon to which it is attached, or ortho-benzylene optionally as part of a six-membered ring, each of which may be optionally substituted by one or more of $C_1$-$C_{20}$ alkyl, $C_1$-$C_6$ alkoxy, halogen, or amine, wherein the five or six membered ring optionally comprises one or more heteroatom, and wherein, in the complex of formula (I), $R^3$ is H and $A^1$ is $A^2$-$CHR^{11}$—.

In accordance with another aspect of the present application, there is provided a process for the preparation of the complex of formula (Ia), the process comprising the step of converting the dienamido complex of Formula (XI) to the complex of formula (Ia)

Other isomers of these complexes exist and can be made using the methods described herein. For example the (R,R) isomer of the diamine NH$_2$CHPhCHPhNH$_2$ is commercially available and can be used to make the corresponding (R,R)

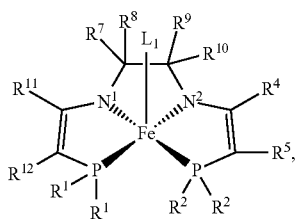

(XI)

where $R^{11}$ and $R^{12}$ are each independently H, or optionally substituted $C_1$-$C_8$ alkyl, $C_2$-$C_8$ alkenyl, aryl, cycloalkyl, sulfonato, nitro, amino, alkoxy, carboxy, or carboxylato, or $R^{11}$ and $R^{12}$, together with the carbons to which they are attached, form a five or six membered ring that is optionally substituted by one or more of $C_1$-$C_{20}$ alkyl, $C_1$-$C_6$ alkoxy, halogen, or amine, wherein the five or six membered ring optionally comprises one or more heteroatom, and wherein, in the complex of formula (Ia), $L^2$, $R^3$, $R^6$ and $R^{4'}$ are absent and where $A^1$ is —$CHR^{12}CHR^{11}$—.

In accordance with another aspect of the present application, there is provided a process for the preparation of the complex of formula (I), the process comprising the step of reacting a phosphonium dimer of Formula (VI) with a PNN proligand of Formula (V) and an iron complex in the presence of a base

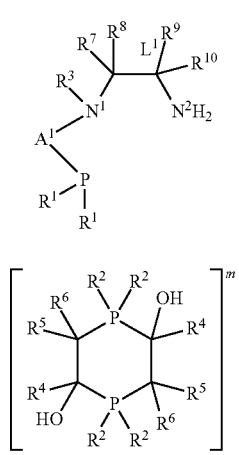

(V)

(VI)

where substituents $R^1$-$R^{10}$ and $A^1$ are the same as defined above.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION OF THE INVENTION

Definitions

Figure 1:
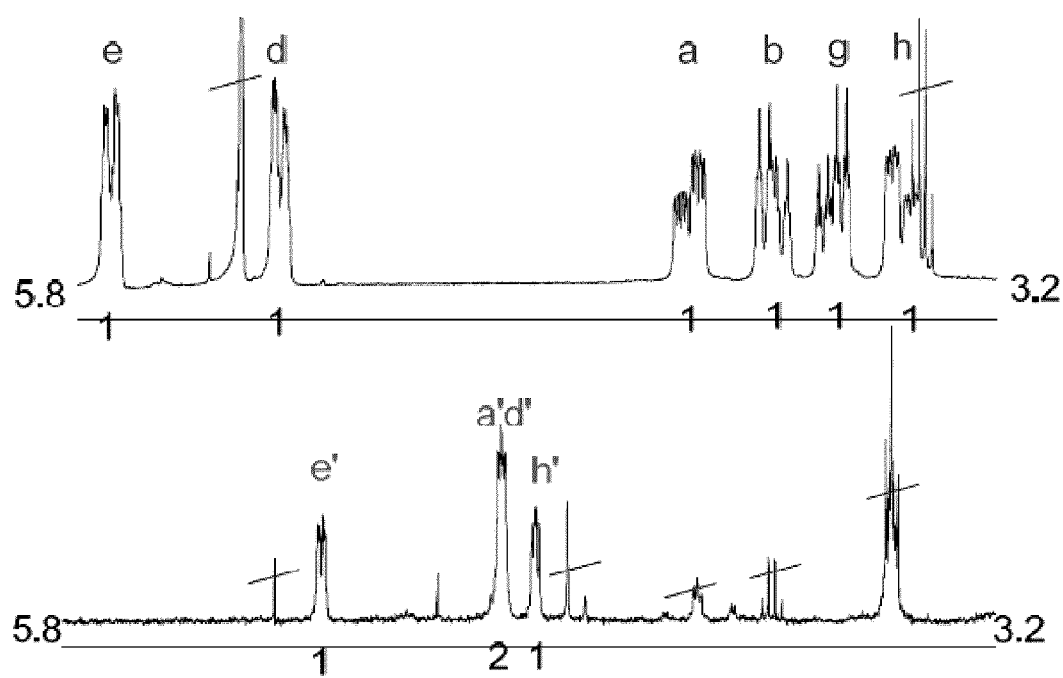
FIG. 1 depicts the bis(eneamido) complex (S,S)-8 and the comparison of a selected region (3.2-5.8 ppm) of the $^1$H NMR spectrum of the complexes (S,S)-7 and (S,S)-8.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or ingredient(s) as appropriate.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

As used herein, "alkyl" refers to a linear, branched or cyclic, saturated or unsaturated hydrocarbon group which can be unsubstituted or is optionally substituted with one or more substituents. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1- butyl, 1-heptyl and 1-octyl. As used herein the term "alkyl" encompasses cyclic alkyls, or cycloalkyl groups.

The term "alkylene" as used herein means a bivalent alkyl group.

The term "cycloalkyl" as used herein refers to a non-aromatic, saturated monocyclic, bicyclic or tricyclic hydrocarbon ring system containing at least 3 carbon atoms. Examples of $C_3$-$C_{12}$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, the term "alkenyl" refers to a straight, branched or cyclic hydrocarbon group containing at least one double bond which can be unsubstituted or optionally substituted with one or more substituents.

As used herein, "alkynyl" refers to an unsaturated, straight or branched chain hydrocarbon group containing at least one triple bond which can be unsubstituted or optionally substituted with one or more substituents.

As used herein, "allenyl" refers to a straight or branched chain hydrocarbon group containing a carbon atom connected by double bonds to two other carbon atoms, which can be unsubstituted or optionally substituted with one or more substituents.

As used herein, "aryl" refers to hydrocarbons derived from benzene or a benzene derivative that are unsaturated aromatic carbocyclic groups of from 6 to 100 carbon atoms, or from which may or may not be a fused ring system, in some embodiments 6 to 50, in other embodiments 6 to 25, and in still other embodiments 6 to 15. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted 4-ethylphenyl and the like.

As used herein, "heteroaryl" refers to an aryl that includes from 1 to 10, in other embodiments 1 to 4, heteroatoms selected from oxygen, nitrogen and sulfur, which can be substituted or unsubstituted.

As used herein, a "heteroatom" refers to an atom that is not carbon or hydrogen, such as nitrogen, oxygen, sulfur, phosphorus, chlorine, bromine, and iodine. The term "heteroaromatic" as used herein refers to a five- or six-membered aromatic ring comprising at least one hetero moiety selected from O, S, N, NH and $NC_{1-4}$alkyl. Heteroaromatic groups include, for example, furanyl, thiophenyl, pyrrolyl, 1,2- or 1,3-oxazolyl, 1,2- or 1,3-diazolyl, 1,2,3- or 1,2,4-triazolyl, and the like. The term "heteromoiety" as used herein means a heteroatom-containing moiety.

As used herein, a "heterocycle" is an aromatic or non-aromatic monocyclic or bicyclic ring of carbon atoms and from 1 to 4 heteroatoms selected from oxygen, nitrogen and sulfur, and which can be substituted or unsubstituted. Included within the term "heterocycle" are heteroaryls, as defined above. Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

As used herein, "halogen" or "halo" refers to F, Cl, Br or I. The term "halide" refers to a halogen atom bearing a negative charge.

As used herein, a "coordinating atom" refers to an atom having a lone pair of electrons capable of coordinating, or forming a covalent dative bond, with a metal atom.

As used herein, "substituted" refers to the structure having one or more substituents. A substituent is an atom or group of bonded atoms that can be considered to have replaced one or more hydrogen atoms attached to a parent molecular entity. Examples of substituents include aliphatic groups, halogen, arylcarbonyloxy, alkoxycarbonyloxy, aryloxycarbonyloxy, alkoxycarbonyl, aminocarbonyl, alkylthiocarbonyl, alkoxyl, phosphate ester, phosphonato, phosphinato, cyano, tertiary amino, tertiary acylamino, tertiary amide, imino, alkylthio, arylthio, sulfonato, sulfamoyl, tertiary sulfonamido, nitrile, trifluoromethyl, heterocyclyl, aromatic, and heteroaromatic moieties, ether, ester, boron-containing moieties, tertiary phosphines, and silicon-containing moieties. The term "optionally substituted" means unsubstituted or substituted.

As used herein, a dashed line in a chemical structure is intended to indicate that a double bond may or may not be present. In the case where two adjacent bonds are shown with a dashed line, only one of the bonds can be a double bond.

As used herein, the term "amide" refers both to functional groups represented by the formula $NR_2C(O)R'$ and to functional groups represented by the formula $R_2N^-$.

As used herein, the term "electron withdrawing group" refers to an electronegative group capable of polarizing a bond with a carbon atom. Some examples of electron withdrawing groups are halogens, $CF_3$, nitro, nitrile, carbonyl and substituted carbonyl.

The term "fluoro-substituted" as used herein refers to a group in which one or more, including all, of the hydrogen atoms have been replaced with a fluorine atom.

The terms "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas). Examples of suitable protecting groups include but are not limited to t-BOC, Ts, Ms, TBDMS, TBDPS, Tf, Bn, allyl, Fmoc, $C_{1-16}$acyl and the like. t-BOC as used herein refers to the group t-butyloxycarbonyl. Ac as used herein refers to the group acetyl. Ts (tosyl) as used herein refers to the group p-toluenesulfonyl. Ms as used herein refers to the group methanesulfonyl. TBDMS as used herein refers to the group t-butyldimethylsilyl. TBDPS as used herein refers to the group t-butyldiphenylsilyl. Tf as used herein refers to the group trifluoromethanesulfonyl. Ns as used herein refers to the group naphthalene sulphonyl. Bn as used herein refers to the group benzyl. Fmoc as used here refers to the group fluorenylmethoxycarbonyl The term "PNNP" refers to the atoms in the ligand, in sequence, which coordinate to the metal centre of the catalyst. In the described tetradentate ligands, the coordinating atoms are phosphorus-nitrogen-nitrogen-phosphorous, hence P—N—N—P.

As used herein, the terms "catalyst", "catalyst complex" and "complex" refer to the hexa-coordinate iron (II) species. These terms encompass both the catalyst precursors, as well as the active catalysts. These species can be neutrally charged and can exist without a counterion, or can be positively charged and associated with one or more non-coordinating anions(s) to balance the charge.

As used herein, the term "activated catalyst" refers to a structure which can be generated upon chemical treatment of a catalyst or catalyst precursor. The activated catalyst can be generated in situ prior to reaction with the substrate. The activated catalyst can also be isolated for later use, or added to a reaction as is.

As used herein, the term "non-coordinating anion" refers to a negatively charged ion that associates with a positively charged catalyst to charge balance the catalyst complex. The non-coordinating anion can be any conjugate base of a strong acid.

As used herein, the term "ligand", abbreviated L, refers to a chemical species that coordinates with the iron centre of the catalyst. The ligand is a Lewis base that can be, for example: a carbon donor such as carbon monoxide, carbene, cyanide or isocyanide (isonitrile); a nitrogen donor, such as nitrosyl, amine, imine, amide, N-heterocycles, nitriles, dinitrogen, or hydrazine; a phosphorous donor, such as phosphines or phosphites; a boron donor, such as boryl; a hydrogen donor, such as dihydrogen, hydride, borohydride, aluminum hydride or other hydride complexes; silane; a silicon donor, such as, silyl; an oxygen donor, such as alcohols, alkoxides, ethers, esters, amides, carboxylates, carboxylic acids, phosphine oxides, sulfoxides or sulfones; a sulfur donor, such as thiols, sulfoxides, thiophenes or sulphides; or a fluorine donor, such as $BF_4^-$.

As used herein, the terms "induction" and "induction period" refers to the initial period of a chemical reaction wherein the rate of the reaction is slow. The induction period is the time required to generate a critical amount of the active catalyst to accelerate the chemical reaction. A chemical reaction having no induction period is characterized by an immediate acceleration of the reaction because there is a sufficient concentration of the active catalyst at the start of the reaction.

As used herein, the term "transfer hydrogenation" refers to the movement, mediated by a catalyst, of a dihydrogen equivalent from a hydrogen source, typically an alcohol such as isopropanol or a formate salt, to a molecule with an unsaturated group such as a carbonyl or imine.

As used herein, the term "asymmetric transfer hydrogenation" refers to a transfer hydrogenation of a prochiral ketone or imine to produce an enantioenriched alcohol or amine, catalyzed by an enantiomeric or enantiopure metal complex.

As used herein, the term "two phase system", refers to the conditions of a reaction wherein two immicible liquids form an interface where the catalyst is in one phase, typically water, and the substrate to be hydrogenated is in another phase. Carrying out reactions in a two phase system often increases the ease of separation of the product from the catalyst.

Complexes

Described herein are catalysts useful for hydrogenation and/or asymmetric hydrogenation. Specifically, the described catalysts are iron (II) complexes containing tetradentate diphosphine (PNNP) ligands.

Complexes as described herein have the general structure of formula (I)

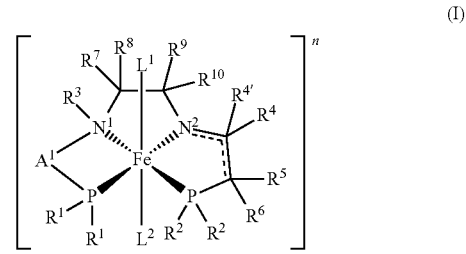

wherein:

$N^1$ and $N^2$ are nitrogen atoms;

$A^1$ is $C_{1-4}$ alkylene, optionally as part of a five or six-membered ring, or ortho-benzylene optionally as part of a six-membered ring, each of which may be optionally substituted by one or more of $C_1$-$C_{20}$ alkyl, $C_1$-$C_6$ alkoxy, halogen, or amine, wherein the five or six membered ring optionally comprises one or more heteroatom;

each $R^1$ and $R^2$ is independently $C_1$-$C_8$ alkyl, $C_2$-$C_8$ alkenyl, $C_1$-$C_8$ alkoxy, aryloxy, $C_3$-$C_8$ cycloalkyl, aryl or heteroaryl, all of which may be optionally substituted, preferably aryl such as phenyl, para-tolyl and meta-xylyl, or both $R^1$ substituents combine to form an optionally substituted $C_2$-$C_4$ linear or $C_3$-$C_8$ branched alkylene, or form a ring together with the phosphorus atom to which they are attached, and/or both $R^2$ substituents combine to form an optionally substituted $C_2$-$C_4$ linear or $C_3$-$C_8$ branched alkylene, or form a ring together with the phosphorus atom to which they are attached;

$R^3$ is H or absent;

$R^4$, $R^5$ and $R^8$ are each independently H, or $C_1$-$C_8$ alkyl, $C_2$-$C_8$ alkenyl, aryl, or cycloalkyl, each of which may be optionally substituted;

$R^{4'}$ is H or absent;

$R^6$ is H or absent;

$R^7$, $R^9$ and $R^{10}$ are each independently H, or $C_1$-$C_8$ alkyl, $C_2$-$C_8$ alkenyl, aryl, or cycloalkyl, each of which may be optionally substituted, or $R^7$ and $R^9$ together with the carbon atoms to which they are attached form an optionally substituted $C_{5-8}$ cycloalkyl ring, or $R^9$ and $R^{10}$ together with the carbon atom to which they are attached form a carbonyl group;

$L^1$ is CO, CNR, $CN^-$, N-heterocyclic carbene or NO, wherein R is $C_1$-$C_8$ alkyl, linear or branched, for example n-Bu or tert-Bu, optionally substituted with vinyl or triethoxysilane, or aryl such as phenyl, tolyl, 4-vinylphenyl, 4-alkylphenyl, all of which may be optionally substituted with vinyl, triethoxysilane or phosphinate;

$L^2$ is absent or is hydride, optionally substituted pyridine, N-methylacetamide, N-methylformamide, optionally substituted imidazole, halide, or $R^aOH$, $NCR^a$ or $^-OR^a$, wherein $R^a$ is aryl, heteroaryl, $C_1$-$C_8$ alkyl, $C_2$-$C_8$ alkenyl or $C_3$-$C_8$ cycloalkyl, all of which may be optionally substituted, or $R^b_3N$ wherein each $R^b$ is independently H, methyl or ethyl, or $R^c(CO)R^c$ wherein each $R^c$ is independently $C_1$-$C_8$ alkyl, aryl, or heteroaryl; and n is 0, +1, or +2, wherein when n is +1 or +2, the complex further comprises at least one non-coordinating anion Y, wherein the total charge of all non-coordinating anions in the complex is equal to −n.

In one embodiment, when $R^3$ is H, $L^2$ is hydride, optionally substituted pyridine, N-methylacetamide, N-methylformamide, optionally substituted imidazole, halide, or $R^aOH$, $NCR^a$ or $^-OR^a$, or $R^b{}_3N$, or $R^c(CO)R^c$.

$L^1$ and $L^2$ are shown above in an axial coordination above and below the plane created by the coordination of the PNNP ligand with the iron centre of the complex, respectively. Those of skill in the art will understand that while the definitions for $L^1$ and $L^2$ are set out above, their orientation can be reversed, such that $L^1$ can be located in an axial coordination below the above-noted plane and $L^2$ can be located in an axial coordination above the above-noted plane. This reversed structure is a diastereomer of the first, which may have different activity and selectivity as a catalyst than the first. Although the structures drawn in the present application are of a single diastereomer, it should be understood that the related diastereomers are also encompassed by the present application.

When the complex of formula (I) has an ene-amine at nitrogen $N^2$, the complex will have the structure of formula (Ia) (which is equivalent to the structure of formula (III) when $R^3$ is H):

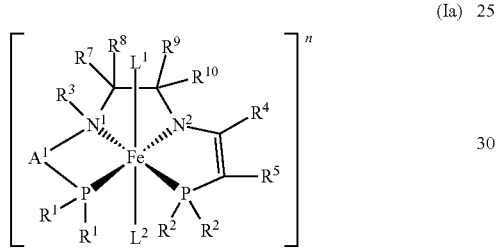

(Ia)

When the complex of formula (I) has an imine at nitrogen $N^2$, the complex will have the structure of formula (Ib):

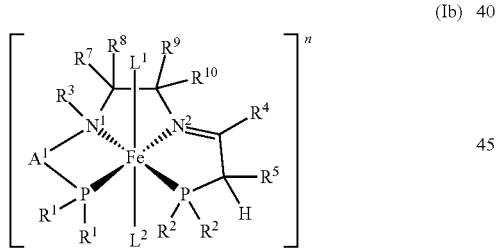

(Ib)

When the complex of formula (I) has an amide at nitrogen $N^2$, the complex will have the structure of formula (Ic):

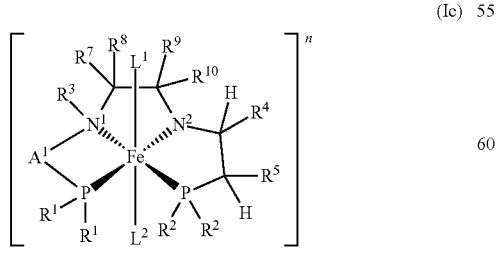

(Ic)

The complex can optionally comprise at least one non-coordinating anion. The non-coordinating anion can be any conjugate base of a strong acid. Non-limiting examples include halides, $B(OR)_4^-$, $Al(OR)_4^-$, $P(OR)_6^-$, $BF_4^-$, $PF_6^-$, $SbF_6^-$, $OS(O)_2R^-$, where R is alkyl or aryl, $CH_3SO_3^-$, $CF_3SO_3^-$, $C_6H_5SO_3^-$, p-$CH_3C_6H_4SO_3^-$, $ClO_4^-$, $FeCl_4^{2-}$, $FeBr_4^{2-}$, phosphates, carboranes, optionally substituted, or $B(R^d)_4^-$ or $Al(R^d)_4^-$, wherein each $R^d$ is independently an optionally substituted $C_1$-$C_6$ alkyl, aryl, phenyl, $C_6H_3(CF_3)_2$ and $C_6F_5$, halogen, pseudohalogen, $C_1$-$C_8$ alkoxide, or aryloxide.

Specific, non-limiting, examples of the catalyst complexes are shown below:

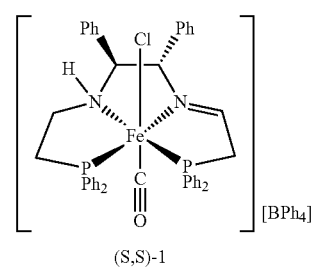

(S,S)-1

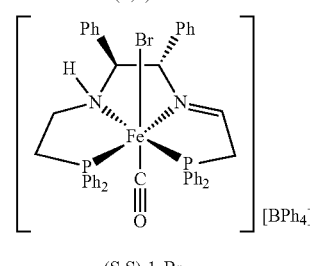

(S,S)-1-Br

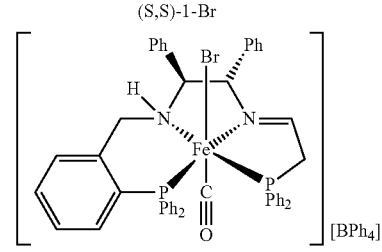

(S,S)-4

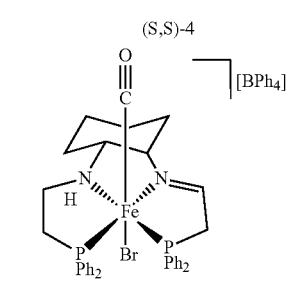

(R,R)-9

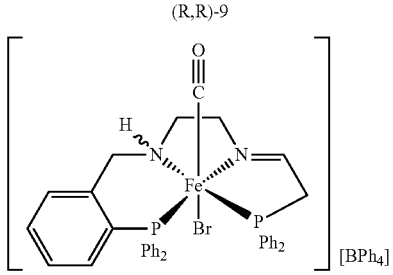

20

-continued

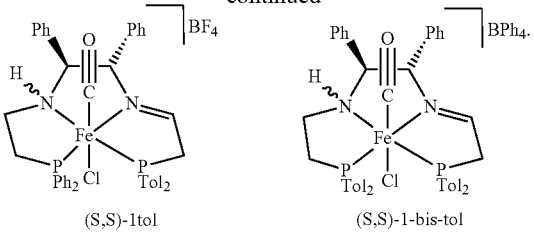

(S,S)-1tol      (S,S)-1-bis-tol

The diastereomers of the above complexes are further examples of the present iron catalyst complexes.

Imine complexes as presently described can be activated upon treatment with a base and a reducing agent, as shown in Scheme 1. Non-limiting examples of the base include an amine or phosphazene or an amide, alkoxide, hydroxide or hydride salt. Non-limiting examples of the reducing agent include a primary or secondary alcohol, boron or aluminum hydride compound, formate salt or other organic hydride source such as NADH and hydrazine. As shown in Scheme 1 the complex of formula (I) includes, $L^1$=CO, $L^2$=halide, $R^3$=H, $R^6$=H. MOR is a base such as potassium tert-butoxide or potassium hydroxide; and, in the reaction shown in Scheme 1, a non-coordinating anion Y is eliminated as MY.

Scheme 1: Activation of Imine Complexes ($R^6$ = H)

The activated catalyst can be generated in situ prior to reaction with the substrate, or can be prepared independently and isolated for later use.

Upon treatment of (S,S)-1 with basic isopropanol, for example, the complex can be converted into its corresponding active species. In one specific example, (S,S)-1 is converted into (S,S)-2 and (S,S)-3 as shown in Scheme 2.

Scheme 2: Activation of (S,S)-1

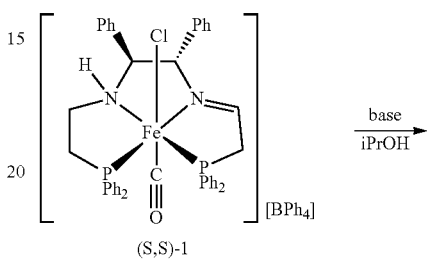

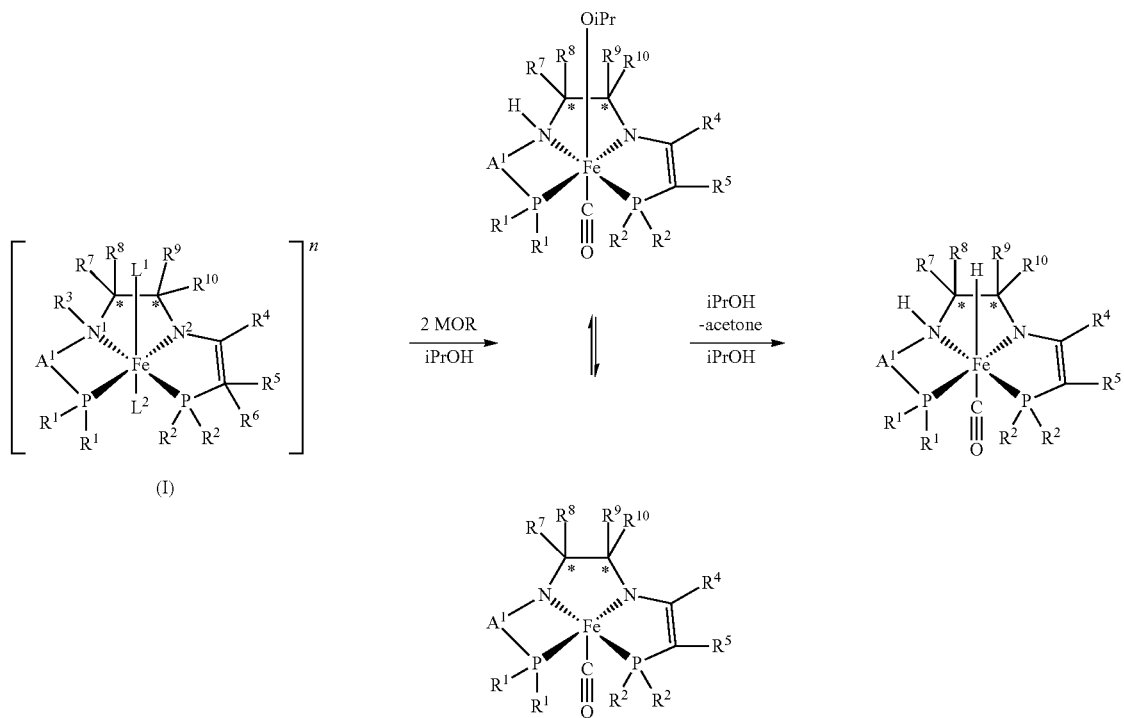

(I)

During activation of the complex, the imine nitrogen in the —$CR^4$—$CR^5$— ring (on the right side of the complex as depicted above) is converted to an eneamide. Specifically, the carbon (α to the $PR^2_2$) in the —$CR^4$—$CR^5$— ring loses a proton ($R^6$=H). Also, the amine nitrogen (on the left side of the complex as depicted above) is deprotonated to give a neutral bis amide complex, or a neutral amine alkoxide complex [Fe(OiPr)(CO)(P—NH—N—P)] can form. These complexes can then react with isopropanol or another hydrogen source to generate the reductant hydride amine iron complex.

-continued

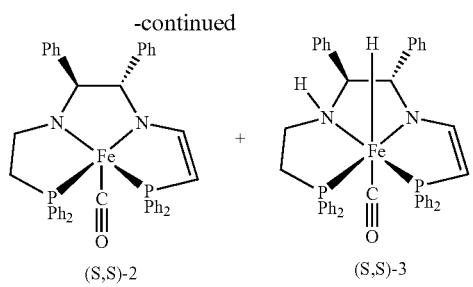

(S,S)-2      (S,S)-3

(S,S)-2 may react with alcohols HOR present in solution to give a neutral amine alkoxide complex [Fe(OR)(P—NH—N—P)(CO)] complex as shown in Scheme 1.

In another specific example, (S,S)-4 is converted into (S,S)-5 and (S,S)-6 as follows:

Scheme 3: Activation of (S,S)-4

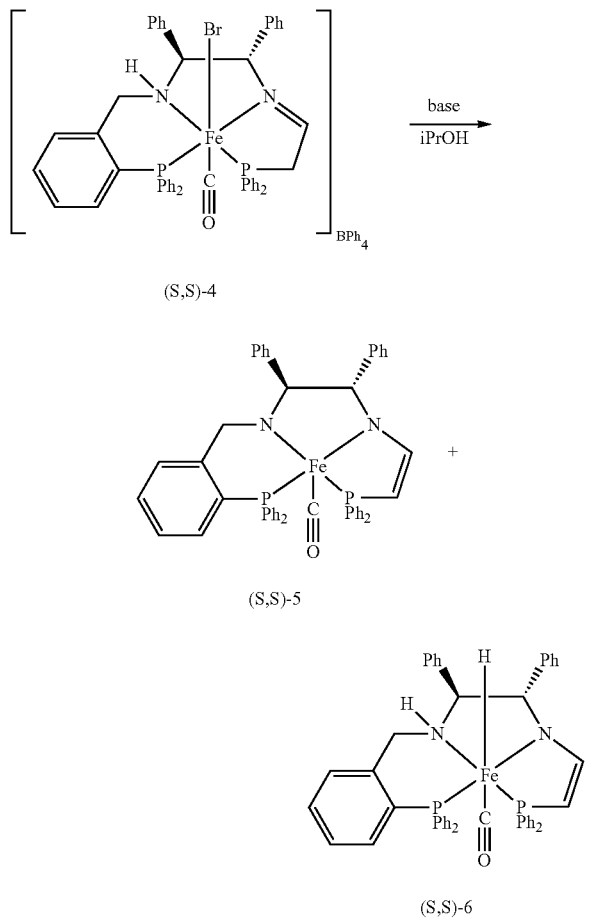

(S,S)-5 can react with alcohols HOR present in solution to give a neutral amine alkoxide complex [Fe(OR)(P—NH—N—P)(CO)] complex as shown generally in Scheme 1.

Catalytic Hydrogenation Methods

The presently described catalysts and complexes are useful for catalytic hydrogenation of unsaturated chemical bonds such as, for example, imines and carbonyl groups. These catalysts are also useful for the effective asymmetric hydrogenation of ketones and imines to give enantiomeric alcohols and amines. Specifically, the activated amine hydride complexes have been shown to be capable of transferring a $H_2$ equivalent (a proton and a hydride) to a ketone or imine polar bond.

Some reactions that may be catalyzed by the presently described compounds are: transfer hydrogenation of ketones, aldehydes, or imines; hydrogenation of ketones, aldehydes, imines, esters, amides, or epoxides; dehydrogenation of alcohols; dehydrogenative coupling of alcohols to produce esters; dehydrogenative coupling of alcohols and amines to produce amides or imines; reductive amination of ketones or aldehydes; hydrosilylation of ketones, aldehydes, imines, or epoxides; hydroboration of aldehydes, imines, esters, amides, or epoxides; hydroamination; hydration; epoxidation; C—C and C—X bond formation including cyanation of ketones, Michael additions, Mukaiyama-aldol reaction, conjugate addition of nitromethane to alpha-hydroxy enones, and ring opening of aziridines; kinetic resolution; dynamic kinetic resolution; 1,3-Dipolar Cycloadditions; Diels-Alder reactions; retro-Diels-Alder reactions; sigmatropic rearrangements; electrocyclic reactions; and combinations of these reactions in tandem.

The present catalysts can be utilized for preparing alcohols or non-racemic alcohols, respectively. Imine groups can similarly be hydrogenated or asymmetrically hydrogenated to provide amines, or non-racemic amines, respectively. It is understood that when an enantiopure catalyst is used the products of these organic reactions will be enantioenriched when a reactant is prochiral.

In some reactions, the present catalysts can be active for transfer hydrogenation at room temperature.

The products of the hydrogenation reactions can be used in subsequent reactions to prepare commercial end products, such as, for example, pharmaceuticals, agrichemicals, cosmetics and nutriceuticals. In one particular example, a catalyst complex as described herein is utilized to improve the process for manufacture of the antiemetic drug, Aprepitant (EIVIEND™ by Merck & Co.), which is a mediator of the neurokinin1 (NK1) receptor. In this example, the substrate is (3,5)-bis-(trifluoromethyl)acetophenone (Scheme 3).

Scheme 3: Production of a valuable enantio-enriched alcohol.

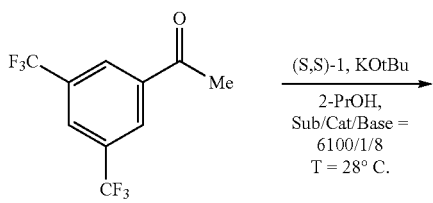

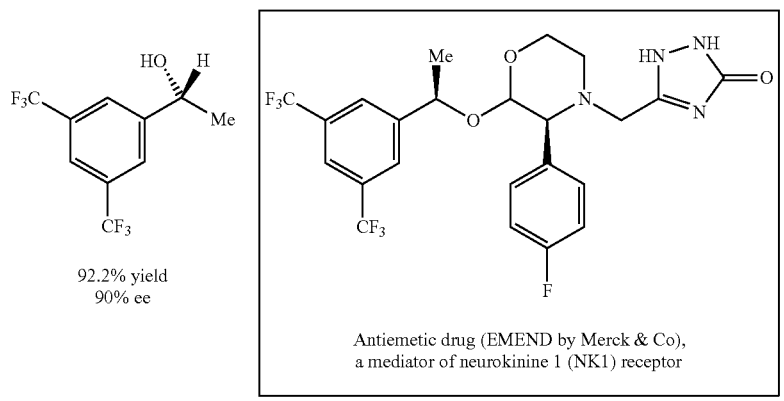

92.2% yield
90% ee

Antiemetic drug (EMEND by Merck & Co), a mediator of neurokinine 1 (NK1) receptor Unlike previously reported catalyst precursors such as (S,S)-7 (United States Patent Application Publication No. US 2010/0145087, incorporated herein by reference), shown below, it has been found that there is a shortened or no induction period before the present catalysts and complexes start working in the reaction.

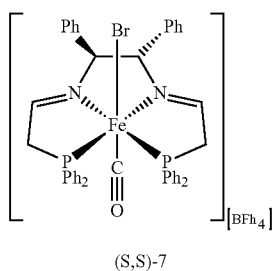

(S,S)-7

Without wishing to be bound by theory, it is thought that the induction period observed when using complexes like (S,S)-7 is caused by the need to reduce the PNNP ligand. However, it has now been found that the complexes described herein, such as (S,S)-1, are activated by a rapid deprotonation reaction thereby providing a higher concentration of the catalyst at the beginning of the reaction.

The present complex and catalyst structures and synthesis allows several opportunities for attachment to a solid or polymeric support. Such catalysts bound to supportive structures simplify catalyst recovery from the reaction, phase separation, or allow continuous flow reactions. Functionalization of said supports can occur via a functional group on the R substituents, or via an isonitrile ligand, or via the phosphorus donor or of one of the other carbons of the ligand skeleton. Synthesis of isonitrile (isocyanide) ligands with a vinyl group for polymerization into a polystyrene support or a triethoxysilane group or an alkoxytriethoxylsilane is well known. (*Chem. Eur. J.* 2010, 16, 1624) Specifically, these can be employed for attachment to a silica surface, or a second isonitrile group for attachment to a metal surface. Similarly, a vinyl, triethoxysilane, azide, amine or carboxylic acid functional group can be incorporated into an R substituent on the tetradentate ligand so that it can be attached to a solid support via polymerization, condensation with a surface functionalized with silicon-hydroxyls groups, click chemistry on a surface functionalized with an alkyne, condensation with a surface functionalized with an aldehyde or carboxylate or a surface functionalized with an amine, respectively. The catalyst can also be held to a support surface by ionic attractions.

Again, without wishing to be bound by theory, a proposed mechanism of the transfer hydrogenation of acetophenone using a complex as presently described is shown in Scheme 4. An alkoxide amine complex may form in place of (S,S)-2 (see Scheme 1).

Scheme 4: Proposed Mechanism of Catalytic Transfer Hydrogenation

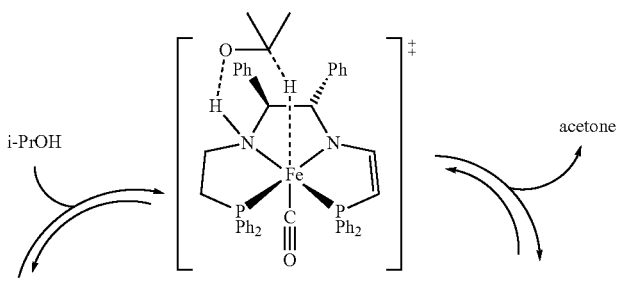

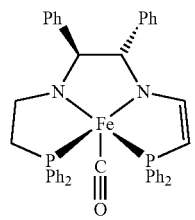

(S,S)-2

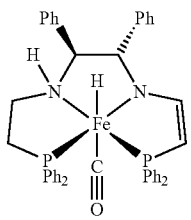

(S,S)-3

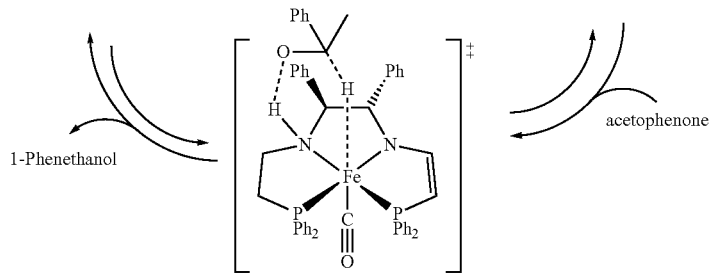

Synthesis of Iron Complexes

The presently described iron complexes can be prepared using various synthetic methods, using starting materials that are commercially available or readily synthesized.

In one embodiment, there is provided a method (method 1) of synthesizing a complex of Formula (I) containing an unsymmetrical amine imine ligand that comprises the step of reducing one imine group in a diimine complex of Formula (X) as in Scheme 5.

Scheme 5.
Method 1 for preparing complex I from a diimine precursor complex X.

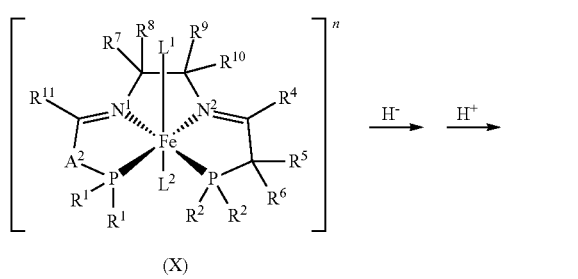

In the above Scheme 5, the substituent $R^{11}$ is H, $C_1$-$C_{20}$ alkyl, $C_1$-$C_6$ alkoxy, halogen, or amine.

In this embodiment, complex of formula X is treated first with a hydride reductant and then with an acid. Non-limiting examples of the hydride reductant are mixtures of primary or secondary alcohols with bases; non limiting examples of the bases are an amine or phosphazene or an amide, alkoxide, hydroxide or hydride salt. The hydride reductant is preferably isopropoxide. Other non-limiting examples of the reducing agent include a boron or aluminum hydride compound, formate salt or other organic hydride source such as NADH and hydrazine. The conditions of the reaction are usually temperatures near room temperature where complex X is dissolved or suspended in a solvent that does not react and remove the hydride from the hydride reductant. Strongly protic solvents should be avoided. The acid in the second step is preferably a hydrogen halide but could be any Bronsted acid with a $pK_a$ less than 14. A reagent such as ammoniaborane can deliver both the hydride and proton. Oxygen from air should be excluded when conducting the reaction.

A non-limiting example of the above method is depicted in the scheme 6 below:

Scheme 6: Method 1 to prepare (S,S)-1

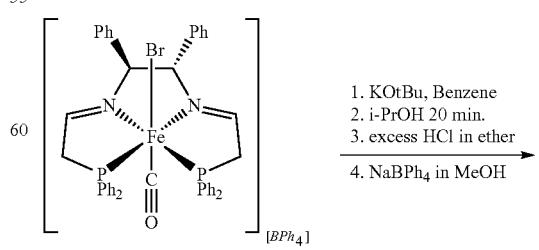

1. KOtBu, Benzene
2. i-PrOH 20 min.
3. excess HCl in ether
4. NaBPh$_4$ in MeOH (S,S)-7

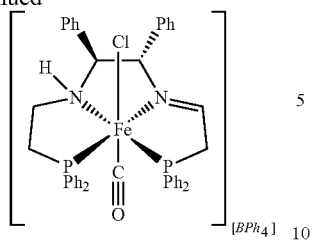

(S,S)-1

In another embodiment, there is provided a method (method 2) of synthesizing a complex of Formula (I) that comprises the step of converting the dienamido complex of Formula (XI) to the complex with an unsymmetrical amido-enamido ligand of Formula (I) (Scheme 7).

Scheme 7.
Method 2 for preparing complex I from a dienamido precursor complex XI.

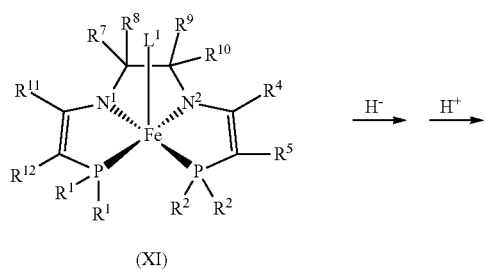

(XI)

(I) with $A^1 = —CHR^{12}—CHR^{11}—$ $L^2, R^3, R^6$ and $R^{4'}$ absent

In this embodiment, the complex of formula XI is treated first with a weak acid and then a hydride source or a reagent such as a secondary or primary alcohol, preferably isopropanol that delivers both of these functions. The conditions of the reaction are usually temperatures near room temperature where complex XI is dissolved or suspended in a solvent that does not react and remove the hydride from the hydride reductant. Protic solvents other than secondary or primary alcohols should be avoided. The complexes in this reaction must be protected from oxygen at all times. The product can be reacted in a further step with a Bronsted acid with a $pK_a$ less than 5, preferably a hydrogen halide to produce a six coordinate complex that is stable to dioxygen.

A non-limiting example of this method is provided in the Scheme 8 set out below.

Scheme 8: The proposed mechanism for method 2 to make (S,S)-1.

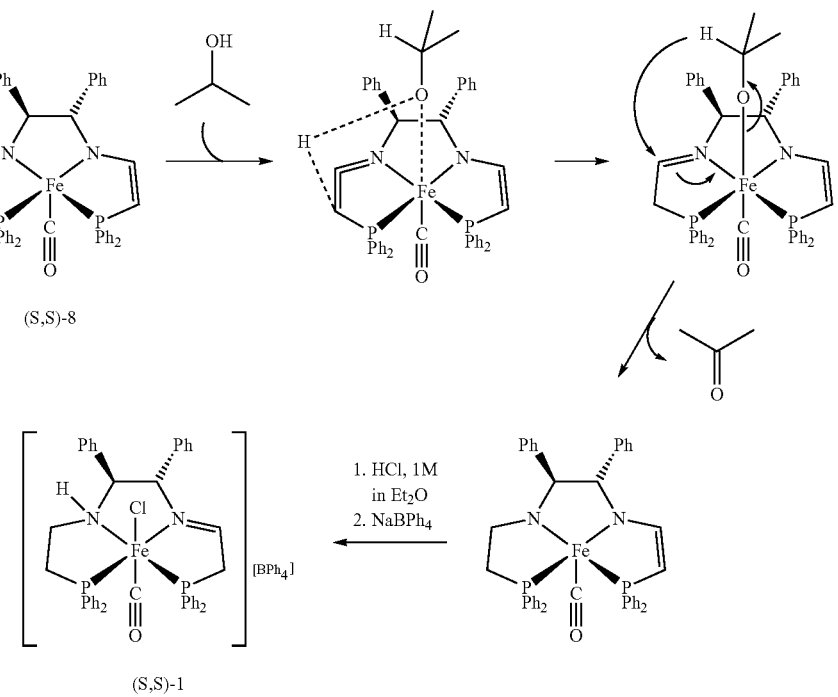

In another embodiment there is provided a method of synthesizing the complex of Formula (I) with $R^{4'}$ absent, which comprises the step of reacting a phosphonium dimer of Formula (VI) with a PNN proligand of Formula (V) and an iron complex, such as $[Fe(H_2O)]_6[BF_4]_2$, or other ferrous salts under basic conditions (Scheme 9).

Scheme 9. General synthesis of a complexes I with an unsymmetrical amine-imine ligand from a P—NH—NH$_2$ ligand (V) and a phosphonium salt (VI) templated by a ferrous salt.

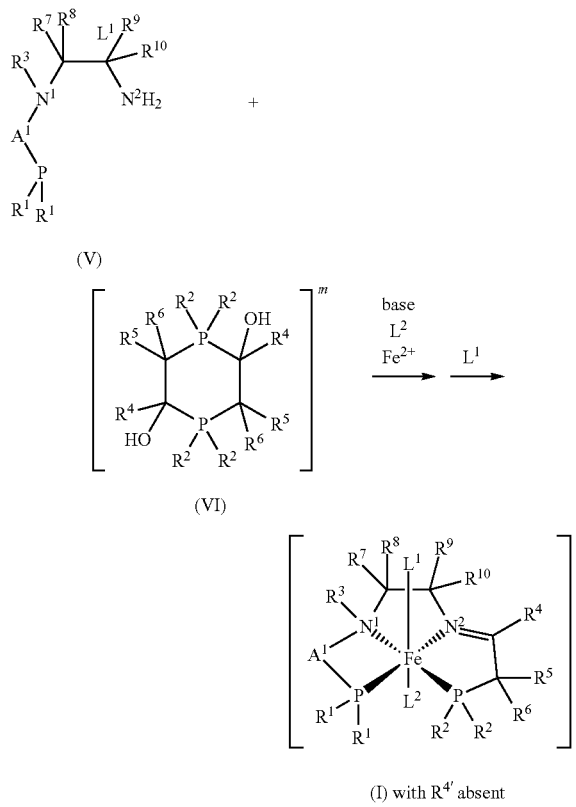

The synthesis of the iron complexes involves two main steps followed in certain cases with the precipitation and isolation of the complex by addition of the alkali metal salt of a non coordinating anion such as tetraphenylborate. In the first the main step the metal salt, the PNN ligand V, the phosphonium dimer VI, the base are combined in the correct proportions in a coordinating solvent such as acetonitrile at room temperature. When the PNN ligand is oxygen sensitive this reaction has to be conducted under a blanket of inert gas such as nitrogen or argon. The reaction times range from seconds to three hours. The reaction is complete when the colour of the solution stops changing. In the second step the solvent is evaporated and the mixture is dissolved in acetone and reacted with the pi-acid ligand $L^1$, typically carbon monoxide (1-10 atm), typically in the presence of an alkali metal salt of a halide (Cl$^-$, Br$^-$, I$^-$), to produce complex I. The reaction with $L^2$ may take up to 3 hours and may require a second exposure to $L^2$ to drive the reaction to completion.

To gain a better understanding of the invention described herein, the following examples are set forth. It should be understood that these examples are for illustrative purposes only. Therefore, they should not limit the scope of this invention in any way.

EXAMPLES

Example 1

Synthesis of Complexes

General Method

All manipulations that involved air- or moisture-sensitive materials were performed using Schlenk techniques or a glovebox under an argon or nitrogen atmosphere. Solvents of high purity (ACS grade or higher) were purchased from Caledon Laboratory Chemicals and were further degassed and dried using standard procedures prior to all manipulations and reactions. (Perrin, D. D., Armarego, W. L. F., Perrin, D. R., *Purification of Laboratory Chemicals*. 2nd ed., Pergamon Press: Oxford, 1980.) Deuterated solvents were purchased from Cambridge Isotope Laboratories, INC and distilled and dried over activated molecular sieves. Acetophenone was distilled under argon and stored under molecular sieves in a glovebox prior to being used in the reduction reactions.

Other reagents used were purchased from commercial sources and utilized without further purification. NMR spectra of the samples that were prepared under argon in degassed solvents were recorded at ambient temperature and pressure using a 400 MHz Varian Gemini [$^1$H (400 MHz), $^{13}$C{$^1$H} (100 MHz), and $^{31}$P{$^1$H} (161 MHz)]. $^1$H NMR spectra were internally referenced to tetramethylsilane (TMS, 0 ppm). $^{13}$C NMR spectra were internally referenced to the carbon resonances of the solvent. The ESI-MS data on samples in methanol/water were done on an AB/Sciex QStar mass spectrometer with an ESI source. The elemental analyses were performed on a Perkin-Elmer 2400 CHN elemental analyzer.

A. Synthesis of Complex (S,S)-1: Method 1

In this example, complex (S,S)-1 was prepared using a method that comprised the step of reducing a diimine complex to the amine-imine complex (see Scheme 6 above). The diimine complex (S,S)-7 was synthesized as described in previous reports. The (R,R) complexes are prepared in an identical fashion starting from the (R,R)-dpen diamine (Mikhailine, A. A, Morris, R. H. Inorg. Chem. 2010, 49, 11039-11044)

The structure of complex (S,S)-1 is similar to the structure of complex (S,S)-7 except that one of the imine functionalities of the ligand is reduced to the amine. The reduction possibly occurred via selective transfer of the hydride from i-PrO$^-$ to one of the imines of the ligand as described in Scheme 8. It also has to be noted that only one diastereomer of complex (S,S)-1 was observed (two possible diastereomers may arise from reduction of one or the other imine of the ligand), since only two doublets were observed in $^{31}$P{$^1$H}NMR spectra, indicating that the reaction is stereospecific.

B. Synthesis of Complex (S,S)-1: Method 2

In order to gain information about the structures of the catalytically active complexes, iPrOH was added to the complex (S,S)-8 (see Scheme 8 above). The green solution turned an orange-red color after 20 min. When the reaction was quenched with a 1 M solution of HCl in diethyl ether (excess was added) the solution became bright yellow. The solvent was evaporated to give a yellow solid, the chloride salt of (S,S)-1.

The major species in the $^{31}$P {$^1$H} NMR spectrum of the solid dissolved in CD$_2$Cl$_2$ had two doublet resonances at 56.2 and 66.0 ppm with J$_{P-P}$=39.3 Hz (~85% relative to all the species that produced $^{31}$P resonances). The solid was purified by precipitation with NaBPh$_4$ from MeOH solution and identified as the amine-imine complex (S,S)-1 (Scheme 8 above) on the basis of HRMS ESI$^+$, $^1$H and $^{31}$P {$^1$H} NMR spectroscopy.

iPrOH (3 mL) was cooled to −25° in a freezer in an argon glovebox and added to a vial charged with stirring bar containing complex (S,S)-8 (0.014 g, 0.020 mmol). The reaction mixture was stirred and allowed to warm up to 25° C. A gradual change of color of the solution was observed from green to orange-red over the course of 25 min of the reaction. The reaction was quenched with a 1M solution of HCl in diethyl ether (excess added), which instantaneously gave a yellow solution. The solvent was evaporated from the reaction mixture to a give yellow solid as a product. The $^{31}$P {$^1$H} NMR spectrum of the crude product in CD$_2$Cl$_2$ showed that the major product had doublet resonances at 55.15 and 64.92 ppm with J$_{p-p}$=39.4 Hz, which accounted for more than 85% of the material present. The compound was further purified. The crude product was dissolved in 1 mL of methanol followed by the addition of a solution (1 mL) of NaBPh$_4$ (0.013 g, 0.038 mmol) in methanol. The product (S,S)-1 was isolated as a yellow solid (yield: 0.011 g, 53%).

(S,S)-1: $^1$H NMR (500 MHz, CD$_2$Cl$_2$) δ: 2.61-2.77 (m, 2H, NCH$_2$), 3.09-3.33 (m, 2H, PCH$_2$ amine side), 3.81-3.95 (m, 2H, PCH$_2$ imine side), 4.38-4.49 (m, 1H, C(Ph)H amine side), 4.57-4.69 (m, 1H, NH), 4.93-5.02 (m, 1H, C(Ph)H imine side), 7.70-7.82 (m, 1H, N=CH), 6.84-7.67 (m, 50H, ArH); $^{13}$C{$^1$H} NMR (100 MHz; CD$_2$Cl$_2$) δ: 46.72-47.11 (m, PCH2), 49.46 (s, HNCH$_2$), 49.51-49.92 (m, PCH$_2$), 76.50 (s, NC(Ph)H), 77.69 (s, NC(Ph)H), 121.3 (s, BPh), 124.-125.1 (m, BPh), 129.9-135.6 (m, ArCH), 135.2-136.2 (m, BPh), 163.7 (m, JCB=49.3 Hz, BPh)

The resonances for the carbonyl (CO) and imine (N=C) carbons were not detected in the spectra due to their longer relaxation times compared to the other carbons in the structure and the lower intensity of the signal due to the expected multiple splitting by $^{31}$P nuclei; $^{31}$P{H} NMR (161 MHz; CD$_2$Cl$_2$): 55.15 (d, J$_{PP}$=39.4 Hz), 64.92 (d, J$_{PP}$=39.4 Hz); HRMS (ESI-TOF) m/z calculated for [C$_{43}$H$_{40}$N$_2$P$_2$FeOCl]$^+$: 753.1648, found: 753.1637.

Synthesis of Complex (S,S)-8 Starting with Complex (S,S)-7

Scheme 10: Synthesis of complex (S,S)-8

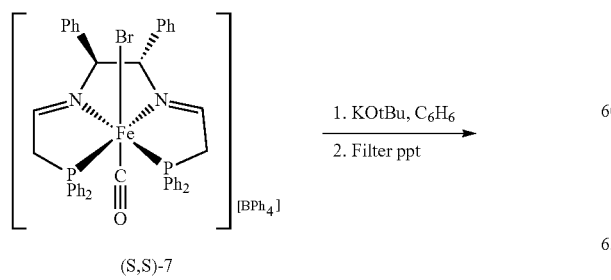

(S,S)-7

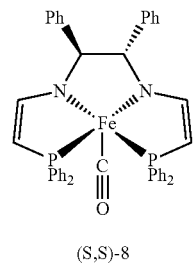

(S,S)-8

The complex (S,S)-7 (Fe(CO)(Ph$_2$PCH=CHN—((S,S)—CH(Ph)CH(Ph))-NCH=CHPPh$_2$)) was obtained using a known method. (Mikhailine, A., Lough, A. J., Morris, R. H. J. Am. Chem. Soc. 2009, 131, 1394-1396) In an argon glovebox, a solution of KOtBu (sublimed, 0.013 g, 0.112 mmol) in 5 mL of benzene was added to a vial charged with a stirring bar containing complex (S,S)-7 (0.050 g, 0.044 mmol). The solution instantaneously became green and a white precipitate was observed. The reaction mixture was stirred for an additional 10 min, filtered through the glass-frit and the solvent was evaporated from the resulting green solution to give a bright green powder. The powder was redissolved in 5 mL of hexanes upon the addition of a few drops of benzene. This solution was filtered through the Celite and the solvent was evaporated. Yield: 0.019 g, 59.3%.

(S,S)-8: $^1$H NMR (400 MHz, C$_6$D$_6$) δ: 4.49-4.57 (m, 1H, PCH), 4.59-4.68 (m, 1H, PCH, 1H, NC(Ph)H), 5.06-5.16 (m, 1H, NC(Ph)H), 6.94-7.50 (m, 30H, ArH), 7.31-7.51 (m, 2H, NCH); $^{31}$P {H} NMR (161 MHz; C$_6$D$_6$) δ: 68.9 (d), 68.6 (d) ppm $^2$J$_{PP}$=25 Hz.

The $^1$H NMR spectra of the product in benzene-d$_6$ shows that the resonances corresponding to the hydrogen atoms of the complex (S,S)-7 are absent but a new set of multiplets was observed. These peaks were assigned to the hydrogens Ha', Hd', He' and Hh' of the neutral bis(ene-amido) iron complex (S,S)-8 as shown below.

Scheme 11: Conversion of (S,S)-7 to (S,S)-8

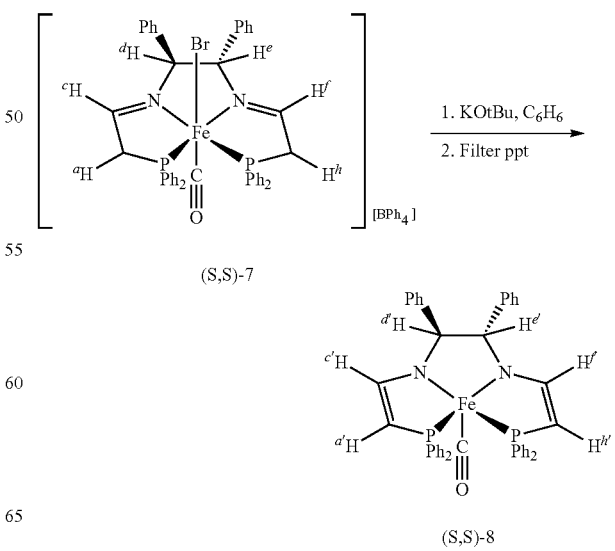

The formation of the bis(eneamido) complex (S,S)-8 and the comparison of a selected region (3.2-5.8 ppm) of the $^1$H NMR spectrum of the complexes (S,S)-7 and (S,S)-8 is are shown in FIG. 1. Coupling between Ha'-Hc' and Hf'-Hh' were identified using 2D COSY experiments to locate the resonances of Hc' and Hf' that were overlapping with aromatic peaks. An absence of the resonances arising from tetraphenylborate in the $^{11}$B NMR spectrum and in the aromatic region of $^1$H NMR spectra peaks is consistent with the formulation of (S,S)-8 as a neutral complex. This highly soluble complex gave an AB pattern in the $^{31}$P {1H} NMR spectrum at 68.9 and 68.6 ppm with $^2J_{P-P}$=25 Hz, which is consistent with a structure having two inequivalent phosphorus atoms.

The decomposition of compound (S,S)-8 in solution or in the solid state under an inert atmosphere occurred after days, but after seconds in the air. Decomposition in solution is signalled by a broadening of the peaks in the $^1$H NMR spectra, resulting from the formation of paramagnetic species, and by a change of color from a deep green to a brown-green. This high reactivity prevented the full characterization of this compound using elemental analysis, high resolution mass spectroscopy or X-ray diffraction.

C. Synthesis of (S,S)-1 and Related Complexes (S,S)-1-Tol,(S,S)-1-Bis-Tol and (S,S)-1-Br Using Method 3

This synthesis of complexes (S,S)-1 and (S,S)-1tol involved two steps. First new enantiopure ligands (S,S)—PAr$_2$CH$_2$CH$_2$NHCHPhCHPNH$_2$, Ar=Ph ((S,S)-21), Tol ((S,S)-22) were made via an iron-based route in 75% yield (Scheme 12). Then the precatalysts were produced in approximately 40% overall yield using a flexible template synthesis (Scheme 13, see below). Few enantiopure P—NH—NH$_2$ ligands are known and they are mainly made from the commercially available phosphine-aldehyde 2-PPh$_2$C$_6$H$_4$CHO or PAr$_2$C$_6$H$_4$CHO. (Clarke, M. L.; Diaz-Valenzuela, M. B.; Slawin, A. M. Z. Organometallics 2007, 26, 16; Diaz-Valenzuela, M. B.; Phillips, S. D.; France, M. B.; Gunn, M. E.; Clarke, M. L. Chem. Eur. J. 2009, 15, 1227; Phillips, S. D.; Andersson, K. H. O.; Kann, N.; Kuntz, M. T.; France, M. B.; Wawrzyniak, P.; Clarke, M. L. Catal. Sci. Technol. 2011, 1, 1336; Carpenter, I.; Eckelmann, S. C.; Kuntz, M. T.; Fuentes, J. A.; France, M. B.; Clarke, M. L. Dalton Trans. 2012, 41, 10136; and Laue, S.; Greiner, L.; Wolfinger, J.; Liese, A. Adv. Synth. Catal. 2001, 343, 711). A P—NH—NH$_2$ ligand (2-PPh$_2$C$_6$H$_4$CH$_2$NHCHPh CHPhNH$_2$) was also synthesized via the condensation of 2-PPh$_2$C$_6$H$_4$CHO and trifluoroacetyl mono-protected (1S, 2S)-1,2-diphenylethylene-diamine ("(S,S)-dpen"). Most enantiopure PNNP and P—NH—NH—P ligands are also made from the reaction of PAr$_2$C$_6$H$_4$CHO phosphine-aldehydes with chiral diamines. (Stoop, R. M.; Bachmann, S.; Valentini, M.; Mezzetti, A. Organometallics 2000, 19, 4117; Gao, J. X.; Ikariya, T.; Noyori, R. Organometallics 1996, 15, 1087; Gao, J. X.; Zhang, H.; Yi, X. D.; Xu, P. P.; Tang, C. L.; Wan, H. L.; Tsai, K. R.; Ikariya, T. Chirality 2000, 12, 383; Wong, W. K.; Gao, J. X.; Wong, W. T.; Che, C. M. Polyhedron 1993, 12, 2063; Li, B.-Z.; Chen, J.-S.; Dong, Z.-R.; Li, Y.-Y.; Li, Q.-B.; Gao, J.-X. J. Mol. Catal. A: Chem. 2006, 258, 113; Ranocchiari, M.; Mezzetti, A. Organometallics 2009, 28, 1286; and Mezzetti, A. Dalton Trans. 2010, 39, 7851).

Scheme 12: Preparation of the (S,S)-PAr$_2$CH$_2$CH$_2$NHCHPhCHPhNH$_2$ ligands (S,S)-21 (Ar = Ph), and (S,S)-22, (Ar = Tol)

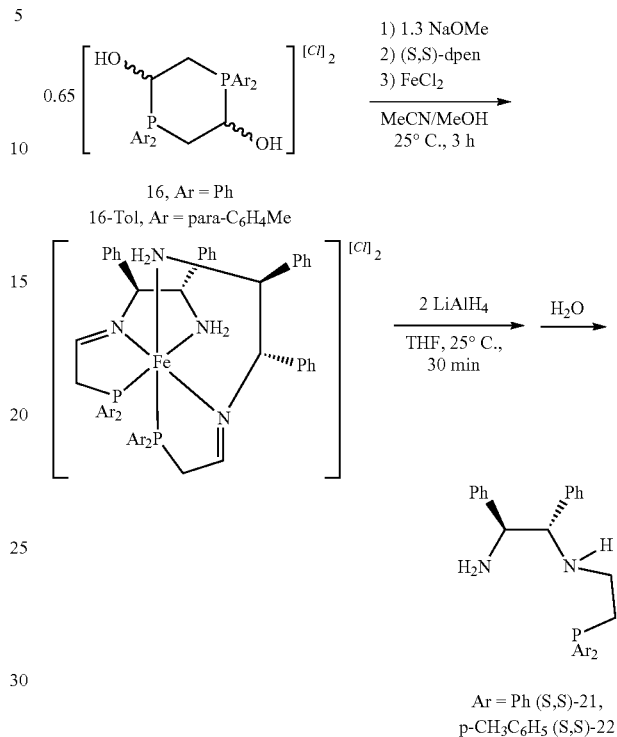

The related phosphino-imine-amine (P—N—NH$_2$) moiety in the previously reported mer-bis-tridentate complexes could be produced in a multicomponent template reaction utilizing the respective phosphonium precursor 16 or 16-tol (Mikhailine, A. A.; Lagaditis, P. O.; Sues, P.; Lough, A. J.; Morris, R. H. J. Organometal. Chem. 2010, 695, 1824-1830), (1R,2R)-1,2-diphenylethylene-diamine ((S,S)-dpen) and [Fe(H$_2$O)$_6$][BF$_4$]$_2$. (Mikhailine, A. A.; Kim, E.; Dingels, C.; Lough, A. J.; Morris, R. H. Inorg. Chem. 2008, 47, 6587) The direct reduction of the imine moiety in the complex by LiAlH$_4$ produces the desired the P—NH—NH$_2$ ligand when it is released from the metal template by reaction with water in the air in 75% yield. The compounds (S,S)-21 and (S,S)-22 are slightly air sensitive and white oily compounds. The (R,R) forms of the ligand are prepared simply by using (R,R)-dpen.

For the diphenylphosphino ligand (S,S)-21, the $^{31}$P {1H} NMR spectrum shows a singlet at −20.1 ppm and the $^1$H NMR spectrum reveals two doublets at 3.68 and 3.91 ppm corresponding to the (S,S)-stilbenyl (CHPhCHPh) backbone hydrogens of the dpen backbone. The —CH$_2$— groups in the ethylene backbone show two multiplets at 2.21 and 2.53 ppm respectively. It should be noted that a slight excess of the phosphonium dimer and a reaction time of 3 h were required to promote the full consumption of the dpen, even though 80% of the reaction occurs immediately after mixing the reactants. Other iron(II) precursors including FeBr$_2$ and [Fe(H$_2$O)$_6$][BF$_4$]$_2$ were also tested, but did not give better results. FeBr$_2$ reacts faster but side products are formed while using [Fe(H$_2$O)$_6$][BF$_4$]$_2$ gave a mixture of several products. In addition, a workup in the air after the protolysis step gave purer products. This may be explained by the oxidation of low-valent iron species, produced by the reduction of iron(II) compounds with LiAlH$_4$, to oxides which can be removed by filtration through Celite.

Experimental:

(i) Synthesis of the Proligands (S,S)—PAr$_2$CH$_2$CH$_2$NHCHPhCHPhNH$_2$, Ar=Ph ((S,S)-21), Tol ((S,S)-22)

Synthesis of (1S,2S)—N$^1$-(2-(diphenylphosphino)ethyl)-1,2-diphenylethane-1,2-diamine ((S,S)-21)

In an argon glovebox, FeCl$_2$ (71.6 mg, 0.565 mmol) was dissolved in MeOH (5 mL) with stirring for about 10 min. (S,S)-1,2-diphenylethylenediamine (120 mg, 0.565 mmol) was dissolved in MeCN (5 mL) in another 20 mL vial. The phosphonium compound 16 (195 mg, 0.367 mmol) was completely dissolved in MeOH (15 mL), and this solution was added to a suspension of NaOMe (39.7 mg, 0.735 mmol) in MeOH (5 mL) in a 10 mL flask charged with a stirring bar, and the mixture was stirred for 5 min. The FeCl$_2$ and (S,S)-1,2-diphenylethylenediamine solution were added to the above colorless solution and it instantaneously became purple. This was allowed to stir for 3 h at room temperature. The solvent was evaporated from the resulting purple solution to give a dark red powder. Then lithium aluminum hydride (42.9 mg, 1.13 mmol) was added followed by 20 mL THF. The resulting black suspension was stirred at room temperature for 30 min. The flask was then taken out of the glovebox and the reaction was quenched with 1 mL of degassed H$_2$O to give a white suspension, which was stirred at room temperature for 15 min. THF was removed under vacuum to give a gray solid, to which, in air, was added 50 mL of H$_2$O and the mixture was stirred for 5 min. The organic product was extracted with dichloromethane (3×30 mL). The DCM solution was filtered through a pad of Celite and the solvent was evaporated. The white oily product was used for the synthesis of iron complexes without further purification. The PNN ligand (S,S)-21 is slightly air sensitive and $^{31}$P NMR analysis indicates that about 4% of the product was oxidized during the workup. However, it is sensitive to both acid and base, and aluminum oxide and silica gel and as a result, further purification was not carried out. $^1$H NMR spectroscopy indicated that the purity was about 90% with some (S,S)-1,2-diphenylethylenediamine and a small portion (less than 5%) of an unknown impurity. $^{31}$P {$^1$H} NMR showed a major singlet at −20.1 ppm for the major product, a small singlet at around 30 ppm for the oxidized product (around 4%) and 2~3 unknown impurities of negligible quantity. yield, 0.180 g, 75%. (S,S)-21: $^1$H NMR (400 MHz, CD$_2$Cl$_2$) δ: 1.68 (brs, NH and NH$_2$), 2.21 (m, 2H, CH$_2$), 2.53 (m, 2H, CH$_2$), 3.68 (d, 1H, $^3$J$_{HH}$=8.0 Hz, —NC(Ph)H), 3.91 (d, 1H, $^3$J$_{HH}$=8.0 Hz, —NC(Ph)H), 7.15-7.45 (m, 20H, ArH). $^{31}$P {$^1$H} NMR (161 MHz; CD$_2$Cl$_2$) δ: −20.1.

Synthesis of (1S,2S)—N$^1$-(2-(di(para-tolyl)phosphino)ethyl)-1,2-diphenylethane-1,2-diamine ((S,S)-22)

This compound was made as for (S,S)-21 using the phosphonium dimer 16-tol (215 mg, 0.367 mmol) in 62.5% yield (0.16 g). $^{31}$P {$^1$H} NMR (161 MHz; CD$_2$Cl$_2$) δ: −20.2.

ii) Synthesis of Complexes (S,S)-1 and (S,S)-1Tol

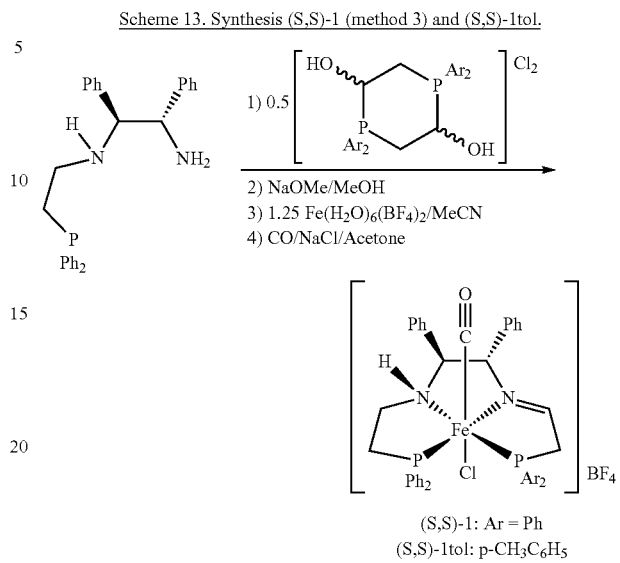

Scheme 13. Synthesis (S,S)-1 (method 3) and (S,S)-1tol.

(S,S)-1: Ar = Ph
(S,S)-1tol: p-CH$_3$C$_6$H$_5$

Figure 7:
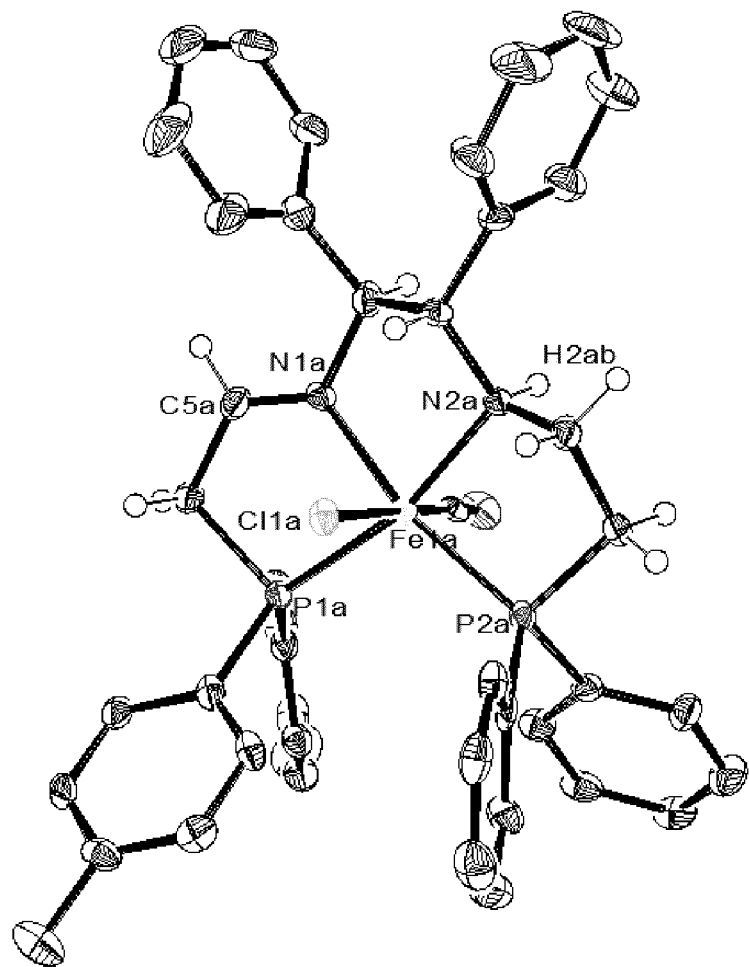
FIG. 7 depicts an ORTEP (with thermal ellipsoids at 50% probability) plot of the X-ray structure of complex (S,S)-1tol (the $BF_4$ anion was omitted for clarity)

The PNN(H)P iron(II) complexes trans-[Fe(CO)(Cl)(PAr$_2$CH$_2$CH=NCHPhCHPhNHCH$_2$CH$_2$PPh$_2$)BF$_4$ ((S,S)-1, Ar=Ph; (S,S)-1tol, Ar=para-CH$_3$C$_6$H$_5$) were synthesized via a template synthesis involving the corresponding phosphonium dimer 16 or 16-tol, [Fe(H$_2$O)]$_6$[BF$_4$]$_2$, NaOMe and enantiopure P—NH—N(H$_2$) ligand (S,S)-21 in MeCN/MeOH solution, followed by an acetonitrile/carbon monoxide exchange reaction in the presence of NaCl in acetone (Scheme 13. Complex (S,S)-1 and (S,S)-1tol precipitate from MeOH solution as BF$_4^-$ salts in moderate yields ((S,S)-1, 42.1%; (S,S)-1tol, 40.5%). The $^{31}$P {$^1$H} NMR spectrum of complex (S,S)-1 in CD$_2$Cl$_2$ had two doublet resonances at 60.2 and 64.9 ppm with J$_{PP}$=40.3 Hz, consistent with a structure having two inequivalent phosphorus atoms. The ν$_{C=O}$ was found at 1978 cm$^{-1}$. The $^{31}$P {$^1$H} NMR spectrum of complex (S,S)-1tol in CD$_2$Cl$_2$ had two doublet resonances at 57.9 and 61.3 ppm with J$_{PP}$=40.6 Hz, A crystals of (S,S)-1tol was analyzed by single crystal X-ray diffraction. As shown in FIG. 7, the geometry around iron is a distorted octahedron with a carbonyl and chloride ligand trans to each other. One notable feature of this structure is that the N(1A)-C(5A) length (1.256(7) Å) is much shorter than that of N(2A)-C(3A) (1.486(7) Å), and these data are in the typical range of C—N bond lengths of imine and amine compounds respectively, consistent with the presence of both amine and imine functionalities in complex (S,S)-1. Similar to its bis(imine) analogues (Mikhailine, A.; Lough, A. J.; Morris, R. H. J. Am. Chem. Soc. 2009, 131, 1394; Lagaditis, P. O.; Lough, A. J.; Morris, R. H. Inorg. Chem. 2010, 49, 10057; Sues, P. E.; Lough, A. J.; Morris, R. H. Organometallics 2011, 30, 4418; and Mikhailine, A. A.; Kim, E.; Dingels, C.; Lough, A. J.; Morris, R. H. Inorg. Chem. 2008, 47, 6587) complex (S,S)-1 has a very wide P—Fe—P angle of 108.96(6)°, probably as a consequence of the small chelate ring sizes (5-,5-,5-membered rings). Noteworthy, the amine proton and the chloride Cl(1A) are located on the different sides of the coordination plane defined by the Fe, N and P atoms. This is interesting as, after activation by base, this chloride ligand would be displaced by a hydride. If such a configuration with the NH next to the carbonyl were maintained in the catalytic conditions, the NH would not be expected to participate in an HFe—NH metal-ligand bifunctional transfer of hydride and proton to the substrate polar bond in an outer sphere mechanism of reduction. However we have evidence that this configuration is not maintained during catalysis (vide infra).

Experimental:

In an argon glovebox, a solution of [Fe(H$_2$O)$_6$][BF$_4$]$_2$ (179 mg, 0.530 mmol) in MeCN (5 mL), a solution of (S,S)-21 (180 mg, 0.424 mmol) in MeOH (3 mL), and a solution of the corresponding phosphonium dimer procursor 16 or 16-tol (112 mg, 0.212 mmol for 16) in MeOH (5 mL) were added into a suspension of NaOMe (22.9 mg, 0.424 mmol) in MeOH (2 mL) in a 20 mL vial charged with a stirring bar. The purple reaction mixture was stirred for 3 h at room temperature. The solvent was removed from the reaction mixture to give a deep purple solid. This was mixed with sodium chloride (27.3 mg, 0.466 mmol) and redissolved in acetone (20 mL) and placed under an atmosphere of carbon monoxide (1.1 atm) and stirred for 3 h at room temperature to give an orange solution with a white precipitate. Acetone was removed under vacuum to afford a yellow solid to which MeOH (2 mL) was added. The brown red solution was shaken to cause the precipitation of a yellow crystalline product, which was washed with MeOH (1 mL) and dried under reduced pressure. Crystals of (S,S)-1tol suitable for X-ray diffraction analysis were grown by slow diffusion of methanol into the DCM solution within 3 h. (S,S)-1: yield, 0.150 g, 42.1%. $^{31}$P {$^1$H} NMR (161 MHz; CD$_2$Cl$_2$) δ: 60.2, 64.9, d, J$_{PP}$=40.3 Hz. (S,S)-1tol: yield, 0.149 g, 40.5%. $^{31}$P {$^1$H} NMR (161 MHz; CD$_2$Cl$_2$) δ: 57.9, 61.3 d, J$_{PP}$=40.6 Hz.

(iii) Synthesis of Complex (S,S)-1Bis-Tol

The complex (S,S)-1bis-tol was prepared using the synthetic method set out above for preparing (S,S)-1 and (S,S)-1tol, except that both (S,S)-22 and the phosphonium compound (16-tol) were substituted with tolyl groups. The following scheme shows the method used to synthesize complex (S,S)-1bis-tol in 20% yield. The lower yield resulted from the higher solubility of the complex.

Scheme 14. Preparation of (S,S)-1bis-tol by use of method 3.

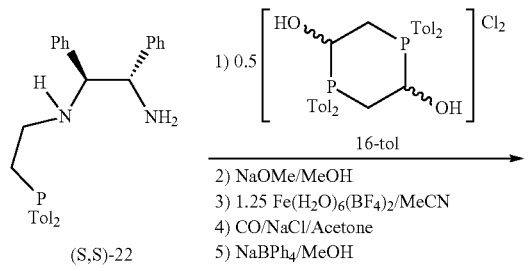

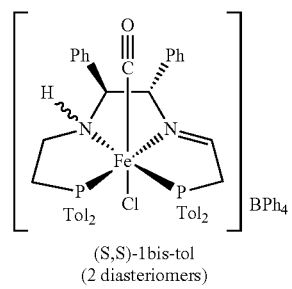

(S,S)-1bis-tol
(2 diasteriomers)

Experimental:

In an argon glovebox, a solution of [Fe(H$_2$O)$_6$][BF$_4$]$_2$ (179 mg, 0.530 mmol) in MeCN (5 mL), a solution of (S,S)-22 (192 mg, 0.424 mmol) in MeOH (3 mL), and a solution of the phosphonium dimer procursor 16-tol (124 mg, 0.212 mmol) in MeOH (5 mL) were added into a suspension of NaOMe (22.9 mg, 0.424 mmol) in MeOH (2 mL) in a 20 mL vial charged with a stirring bar. The purple reaction mixture was stirred for 3 h at room temperature. The solvent was removed from the reaction mixture to give a deep purple solid. This was mixed with sodium chloride (27.3 mg, 0.466 mmol) and redissolved in acetone (20 mL) and placed under an atmosphere of carbon monoxide (1.1 atm) and stirred for 3 h at room temperature to give an orange solution with a white precipitate. Acetone was removed under vacuum to afford a yellow solid to which a sodium tetraphenylborate (145 mg, 0.424 mmol) solution in MeOH (2 mL) was added. Yellow precipitate was formed and filtered. The filtrate was washed with MeOH (5×2 mL) and with diethylether (2×2 mL) and dried under vacuum. Yield: 95 mg, 20%. Two diastereomers in a ratio of 1:1.5 were observed. The major isomer: $^{31}$P {$^1$H} NMR (161 MHz; CD$_2$Cl$_2$) δ: 54.5, 60.3, d, J$_{PP}$=43.2 Hz. The minor isomer: $^{31}$P {$^1$H} NMR (161 MHz; CD$_2$Cl$_2$) δ: 54.2, 63.2, d, J$_{PP}$=40.1 Hz.

(iv) Synthesis of Bromide Analogue of Complex (S,S)-1

The bromide analogue of complex (S,S)-1 can be synthesized according to the following general scheme:

Scheme 15: Synthesis of bromide analogue of complex (S,S)-1

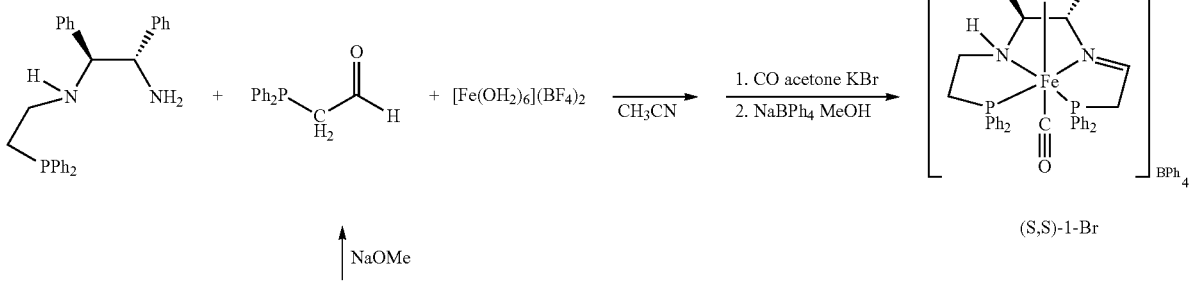

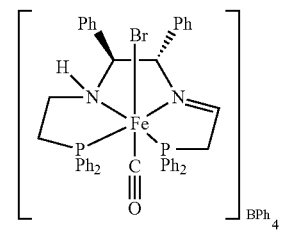

(S,S)-1-Br

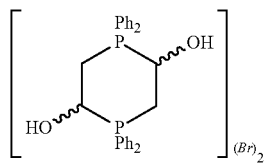
D. Synthesis of Catalyst (R,R)-9, an Analogue of (S,S)-1
The complex (R,R)-9 was prepared via a template synthesis using a phosphonium dimer 16, [Fe(H₂O)]₆[BF₄]₂, and a proligand PNN 15 under basic conditions, followed by an acetonitrile/carbon monoxide exchange reaction, as shown in Scheme 16.
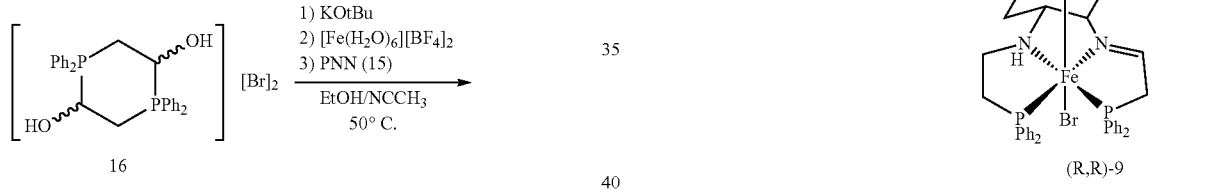
i) Synthesis of Proligand 15
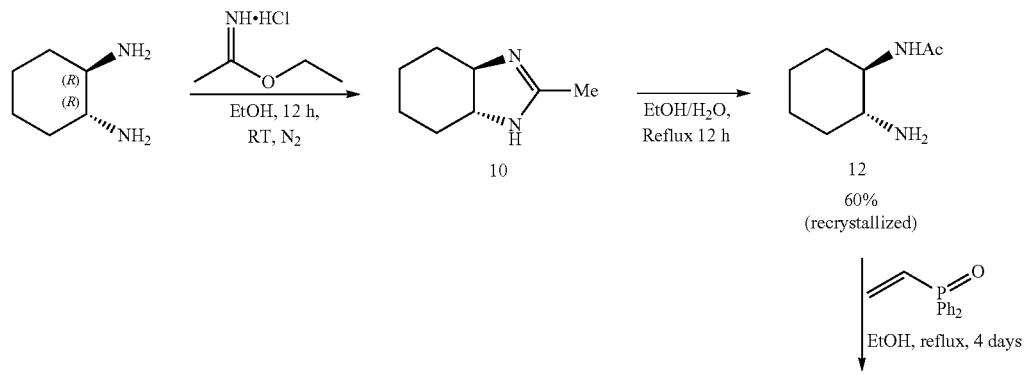

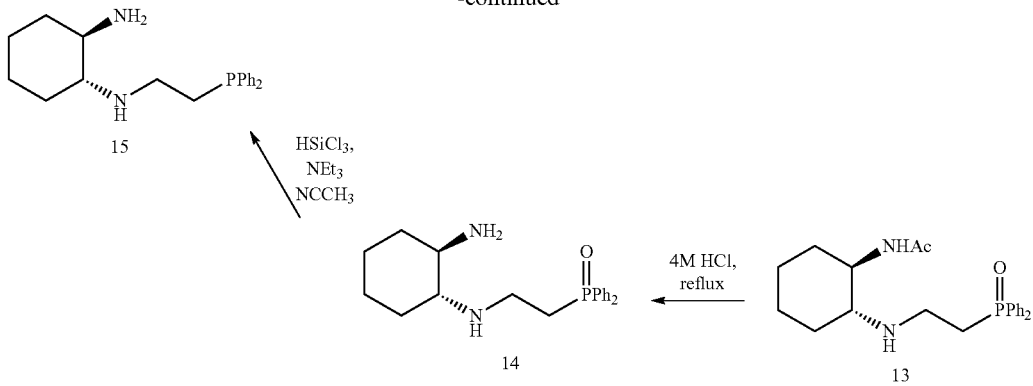

Compound 12 was made following literature procedure starting from (R,R)-1,2-diaminocyclohexane. (Mitchell, J. M., Finney, N. S. *Tetrahedron Lett.* 2000, 41, 8431). Diphenylvinylphosphine oxide was made following literature procedure. (Berlin, K., Butler, G., *J. Org. Chem.* 1961, 26, 2537-2538, Barbaro, P., Bianchini, C., Giambastiani, G., Togni, A., *Chem. Commun.* 2002, 2672-2673; Anderson, C. E., Apperley, D. C., Batsanov, A. S., Dyer, P. W., Howard, J. A. K., *Dalton Trans.* 2006, 4134-4145.)

Compound 13 was synthesized as follows: A round bottom flask was charged with compound 12 (0.5 g, 3.20 mmol) and diphenylvinylphosphine oxide (0.73 g, 3.20 mmol) and ethanol (20 mL). The mixture was allowed to reflux and was complete after 4 days. The solvent was removed in vacuo and the oily residue was triturated with $Et_2O$ until a white sticky solid was obtained and not further purified. $^{31}$P NMR ($CDCl_3$): 32.6 ppm (~90% purity; ~10% diphenylvinylphosphine oxide). MS ESI: 385.2 m/z (PNN+H).

Compound 14 was synthesized as follows: Compound 13 was dissolved in 25 mL of 4M HCl and refluxed overnight. The reaction was then cooled down to room temperature, made basic by adding 4M NaOH (75 mL) and then extracted with 2% methanol-dichloromethane (2×100 mL). The organic phases were combined, dried with $Na_2SO_4$ and concentrated under vacuum to afford an off-white solid (0.7 mg, 64% starting from compound 2). $^{31}$P NMR ($CDCl_3$): 31.6 ppm. MS ESI: 343.2 m/z (PNN+H).

Compound 15 was synthesized as follows: Under an inert atmosphere, compound 14 (1.7 g, 0.005 mol) was dissolved with acetonitrile (50 mL). To this flask $NEt_3$ (2.5 g, 0.025 mol) was added via syringe. The Schlenk flask was then cooled to 0° C. and $HSiCl_3$ (2.5 mL, 0.025 mol) was added. The mixture was refluxed overnight. The reaction was cooled to 0° C. and quenched by the addition of 75 mL degassed 10% NaOH solution. The top organic layer was removed and dried over $Na_2SO_4$, then concentrated to afford a pale yellow oil (1.1 g, 68%). $^{31}$P NMR ($CD_3CN$): −20.7 ppm, MS ESI: 326.2 m/z (PNN+H)

ii) Synthesis of (R,R)-9 (Scheme 16 Above)

Phosphonium compound 16 was prepared according to a known procedure. (Mikhailine, A. A., Morris, R. H., *Inorg. Chem.* 2010, 49, 11039-11044.) A vial was charged with compound 16 (100 mg, 0.162 mmol), KOtBu (37 mg, 0.324 mmol), 20 mL ethanol and 5 mL acetonitrile. To this mixture $[Fe(H_2O)_6][BF_4]_2$ (164 mg, 0.486 mmol) was added, followed by compound 15 (106 mg, 0.324 mmol). The mixture was transferred to a Schlenk flask and the mixture was allowed to stir overnight at 50° C. A sample was taken for $^{31}$P NMR spectroscopy and showed the reaction was complete in the formation of compound 17 (62.5 and 67.2 ppm; $J_{PP}$=26 Hz). The solvent was then removed and the pink residue was dissolved in dichloromethane (10 mL) and filtered. A small scoop (~30 mg) of KBr was added and the mixture was allowed to stir under a CO atm headspace. After 2 days, the solvent was removed, taken up with MeOH, filtered to removed excess KBr and added to a vial with $NaBPh_4$ (140 mg) in 1 mL MeOH. A yellow precipitate formed but an appreciable amount still remained in solution (as since the filtrate was yellow). The solvent was removed, taken up with dichloromethane and filtered. The solvent was removed and the residue was triturated with pentane until (R,R)-9 as a dark yellow solid was isolated (180 mg, 55%). A $^{31}$P NMR spectrum revealed two compounds: 54.6 & 60.6 ppm ($J_{PP}$=38 Hz) and 54.9 & 64.2 ppm ($J_{PP}$=39 Hz). MS ESI: 701.1 m/z.

E. Synthesis of Complex (S,S)-4

Scheme 18: General Synthesis of (S,S)-4

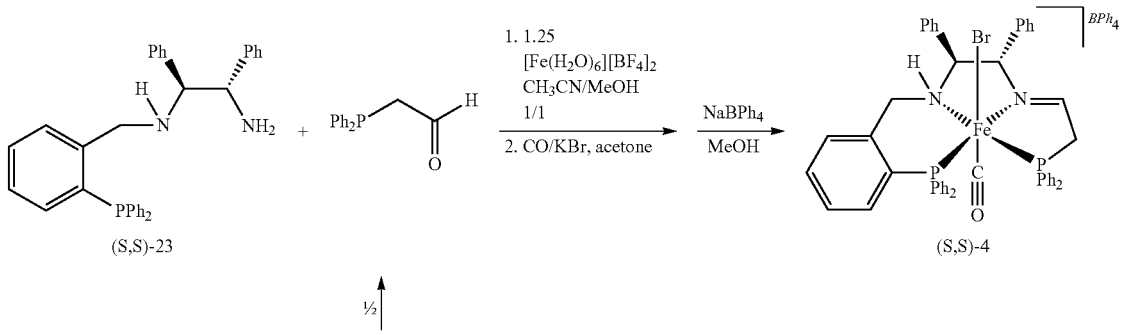

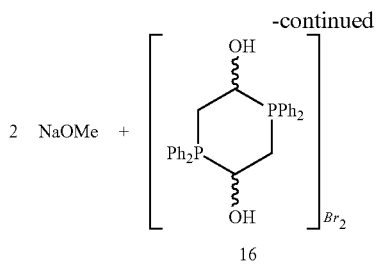

16 i) Synthesis of Proligand PNHNH$_2$ (S,S)-23

The method for the preparation of mono-substituted diimines can also be applied for the preparation of the PNN ligand with (1S,2S)-diphenylethylenediamine (DPEN). An alternative synthetic protocol involving initial protection of the diamine, which was previously described by A. Togni and co-workers (Fluckiger, M.; Togni, A., Eur. J. Org. Chem. 2011, 4353-4360) can also utilized, as described below, and involves the reaction of (S,S)-DPEN with ethyl-trifluoroacetate (Scheme 19).

Scheme 19: Synthesis of mono-protected (S,S)-DPEN

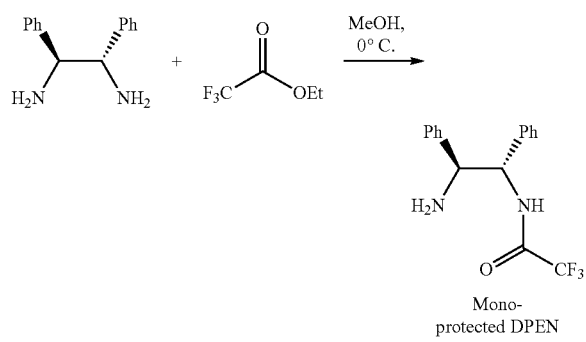

The mono-protected DPEN can undergo a selective condensation reaction with an aldehyde in MeOH with addition of catalytic amounts of glacial acetic acid to give the desired imine, which after the reduction and deprotection with an excess of sodium borohydride gives the desired PNNH$_2$ ligand, as shown in Scheme 20 below.

Scheme 20: Synthesis of the PNNH$_2$ ligand (S,S)-23

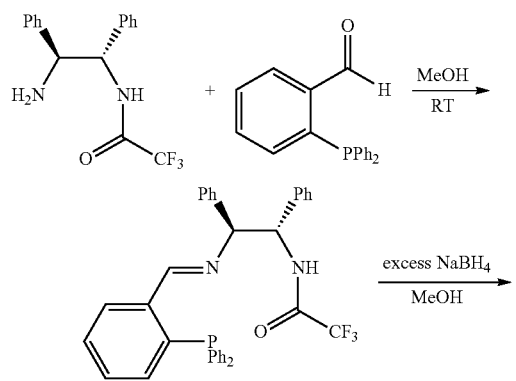

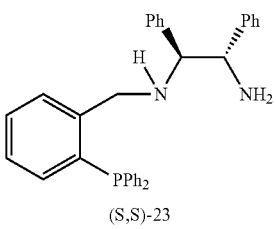

(S,S)-23 ii) Synthesis of (S,S)-4

In an Ar-glovebox the P—N—NH$_2$ ligand (S,S)-23 (1 eq, m=0.10 g, mol=0.21 mmol) and [Fe(H$_2$O)$_6$][BF$_4$]$_2$ (1.25 eq, m=0.087 g, mol=0.26 mmol) were dissolved in the solvent mixture of methanol (15 mL) and acetonitrile (1 mL). The solution instantaneously changed color from colorless to a red-orange. The phosphonium dimer 16 (0.5 eq, m=0.064 g, mol=0.103 mmol) and NaOMe (1 eq, m=0.011 g, mol=0.21 mmol) were dissolved in methanol (2 mL) and stirred for 5 min to obtain a colorless homogeneous solution. The solution containing the phosphonium dimer was added to the solution containing the Fe(II) precursor and PNNH$_2$ ligand over a period of 2 minutes. There was no visible change of color of the solution. After 3 hours the solvent was removed under vacuum and the resulting yellow-red solid was re-dissolved in 4 mL of acetone and KBr (m=0.04 g, mol=0.30 mmol) was added. The suspension was placed under CO atmosphere for 2 hours to give a yellow-brown solution with precipitate. The precipitate was filtered and solvent removed from eluate under reduced pressure to give a yellow solid. The solid was re-dissolved in MeOH (5 mL) and a solution of NaBPh$_4$ (1 eq, m=0.07 g, mol=0.21 mmol) in 3 mL of MeOH was added. The precipitate was formed instantaneously and filtered. The filtrate was washed with MeOH (5×2 mL) and with diethylether (2×2 mL) and dried under vacuum.

(S,S)-4: $^{31}$P NMR (121 MHz, CD$_2$Cl$_2$) δ: 38.7(d) and 52.1(d) ppm (2J$_{PP}$=39.8 Hz); and at 43.5(d) and 51.2(d) ppm (2J$_{PP}$=42.0 Hz). MS (ESI-TOF) m/z calculated for [C$_{48}$H$_{42}$BrFeN$_2$OP$_2$]+:859.1299, found: 859.1318. The $^{31}$P NMR spectrum of complex (S,S)-4 showed that the product is a mixture of two diastereomers of (S,S)-4, which give rise to the resonances at 38.7(d)/52.1(d) ppm ($^2$J$_{PP}$=39.8 Hz) and at 43.5(d)/51.2(d) ppm ($^2$J$_{PP}$=42.0 Hz).

F. Synthesis of the 6,5,5 Catalyst 20 Via Complex 19

Scheme 21: Synthesis of precursor complex 19

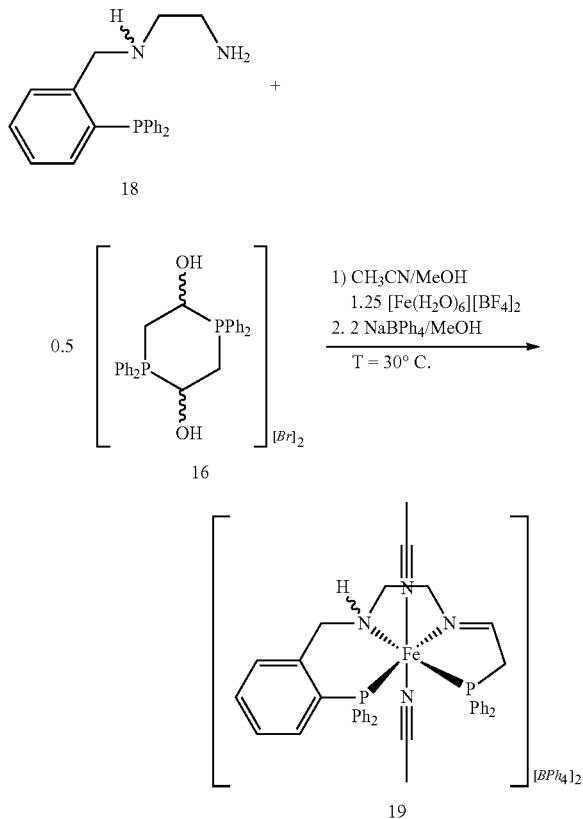

Scheme 22: Synthesis of complex 20

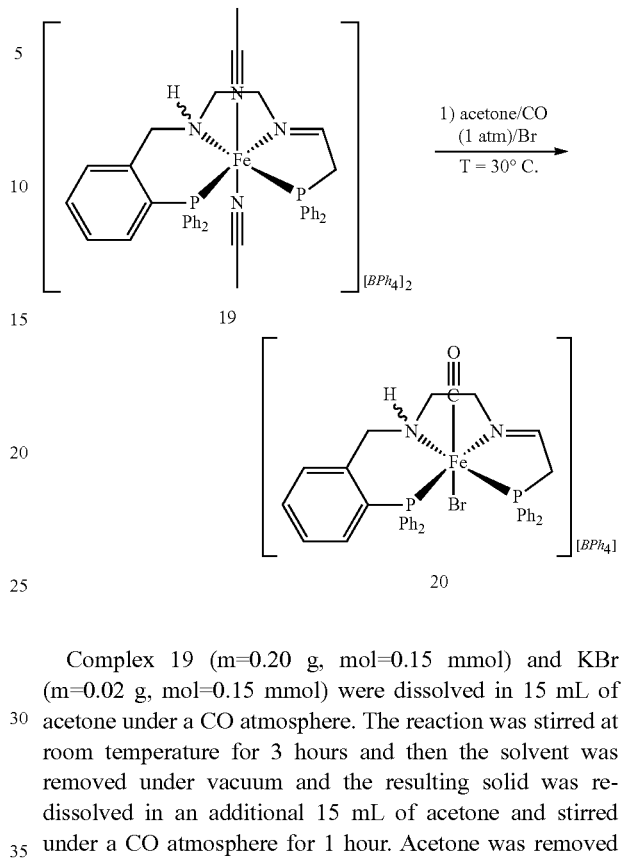

In an Ar-glovebox the PNNH$_2$ ligand 18 (Carpenter, I.; Eckelmann, S. C.; Kuntz, M. T.; Fuentes, J. A.; France, M. B.; Clarke, M. L. *Dalton Trans.* 2012, 41, 10136-10140.) (1 eq, m=0.15 g, mol=0.46 mmol) and [Fe(H$_2$O)$_6$][BF$_4$]$_2$ (1.25 eq, m=0.19 g, mol=0.58 mmol) were dissolved in the solvent mixture of methanol (15 mL) and acetonitrile (1 mL). The solution instantaneously changed color from colorless to a red-orange. The phosphonium dimer 16 (0.5 eq, m=0.14 g, mol=0.23 mmol) and NaOMe (1 eq, m=0.025 g, mol=0.46 mmol) were dissolved in methanol (2 mL) and stirred for 5 min to obtain a colorless homogeneous solution. The solution containing the phosphonium dimer was added to the solution containing the Fe(II) precursor and PNNH$_2$ ligand over a 2 min period. There was no visible change of color of the solution. After 3 hours the solvent was removed under vacuum and the resulting red solid was redissolved in 4 mL of methanol. The resulting homogeneous solution was added to the solution of NaBPh$_4$ (2 eq, m=0.32 g, mol=0.92 mmol) in 2 mL of methanol with vigorous stirring. The resulted pink precipitate was filtered, dried under vacuum and washed with diethylether (2×2 mL). The solid was redissolved in dichloromethane (2 mL) to give a pink solution and white precipitate that was filtered to give a transparent solution. The solvent was removed to give a pink solid that was washed with diethylether (2×2 mL). Yield: m=0.32 g, 92%; $^{31}$P NMR (121 MHz, CD$_2$Cl$_2$) δ: 49.9 (d, $^2J_{PP}$=29.5 Hz), 54.2 (d, $^2J_{PP}$=29.5 Hz); MS (ESI-TOF) m/z calculated for [C$_{35}$H$_{34}$N$_2$P$_2$Fe]$^{2+}$: 300.1, found: 300.1.

Complex 19 (m=0.20 g, mol=0.15 mmol) and KBr (m=0.02 g, mol=0.15 mmol) were dissolved in 15 mL of acetone under a CO atmosphere. The reaction was stirred at room temperature for 3 hours and then the solvent was removed under vacuum and the resulting solid was redissolved in an additional 15 mL of acetone and stirred under a CO atmosphere for 1 hour. Acetone was removed under vacuum and the resulting yellow-brown solid was washed with diethylether (2×3 mL) and redissolved in 1 mL of dichloromethane. The cloudy solution was filtered to give a yellow transparent solution. Solvent was removed under vacuum and washed with diethylether (2×3 mL). The product was isolated as a yellow-brown solid (yield: 0.12 g, 77%). Data for the major isomer (85% of the mixture according to the $^{31}$P NMR).

Complex 20: $^{31}$P {H} NMR (161 MHz; CD$_2$Cl$_2$): 55.53 (d, $^2J_{PP}$=44.8 Hz), 65.93 (d, $^2J_{PP}$=44.8 Hz); Data for the minor isomer (15% of the mixture): $^{31}$P {H} NMR (161 MHz; CD$_2$Cl$_2$): 40.1 (d, $^2J_{PP}$=44.0 Hz), 51.6 (d, $^2J_{PP}$=44.0 Hz); HRMS (ESI-TOF) m/z calculated for [C$_{36}$H$_{34}$N$_2$P$_2$FeOBr]+: 707.0673, found: 707.0766.

Example 2

Catalytic Reduction of Acetophenone

General Reaction

The catalytic reduction of acetophenone to 1-phenylethanol is a standard reaction used to test asymmetric transfer hydrogenation (ATH) catalysts. The optimized conditions for the ATH of acetophenone to produce enantioenriched 1-phenylethanol using iPrOH as a solvent and a reducing agent were previously reported and are summarized in Scheme 23, below. (Mikhailine, A. A., Morris, R. H. *Inorg. Chem.* 2010, 49, 11039-11044.)

Scheme 23: General reaction of the catalytic reduction of acetophenone

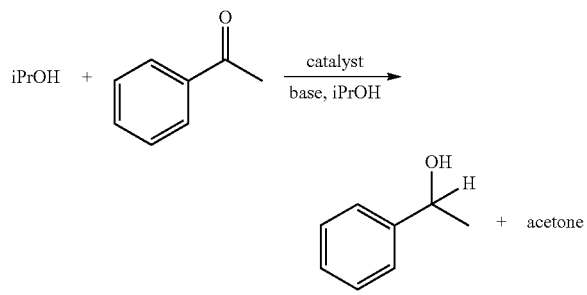

A. Catalytic Reduction of Acetophenone Using Complexes (S,S)-7 and (S,S)-1

The stock solutions were prepared in a glovebox. The stock solution 1 (SS1) was prepared by dissolving the catalyst in acetophenone. The stock solution 2 (SS2) was prepared by dissolving KOtBu in i-PrOH. Prepared solutions were used only after all solids were completely dissolved and for less than two days. A required mass of the SS1 was added to a vial containing i-PrOH charged with a stirring bar and acetophenone to form mixture 1(M1). A required mass of SS2 was added to the second vial containing i-PrOH to give mixture 2 (M2). In order to ensure a constant temperature of the experiment, M1 and M2 were placed into a sand bath with a coil connected to a Fisher Scientific temperature control unit for 15 minutes.

To initiate the reaction, M1 and M2 were mixed by transferring the solutions from a vial to a vial and then placed into a sand bath above a stirring plate. The samples were taken by syringe as small portions of the reaction mixture and then injected into septa-sealed GC-vials containing aerated i-PrOH for efficient quenching of the reaction. Samples were analyzed using a Perkin Elmer Autosystem XL chromatograph with a chiral column (CP chirasil-Dex CB 25 m×2.5 mm). Hydrogen gas was used as a mobile phase at a column pressure of 5 psi. The injector temperature was 250° C., and a FID temperature was 275° C. The amount of the 1-phenylethanol in the sample was determined relative to the acetophenone. The retention times of acetophenone, 1-phenylethanol (R) and 1-phenylethanol (S) were found to be 5.02, 8.73 and 9.42 min. respectively, if the temperature of the oven was kept at 130° C. Conditions: mol (cat)=6.47×10$^{-4}$ mmol, mol (ketone)=3.96 mmol, mol (KOtBu)=5.24×10$^{-3}$ mmol, m (iPrOH)=6 g

TABLE 1

| Entry | R$^I$ | Cat/Sub/Base | Temperature [° C.] | Time [hour] | Conv. [%] | ee [%] |
|---|---|---|---|---|---|---|
| (SS)-1 | Me | 1/6000/8 | 28 | 0.30 | 88 | 82 (R) |

Figure 2:
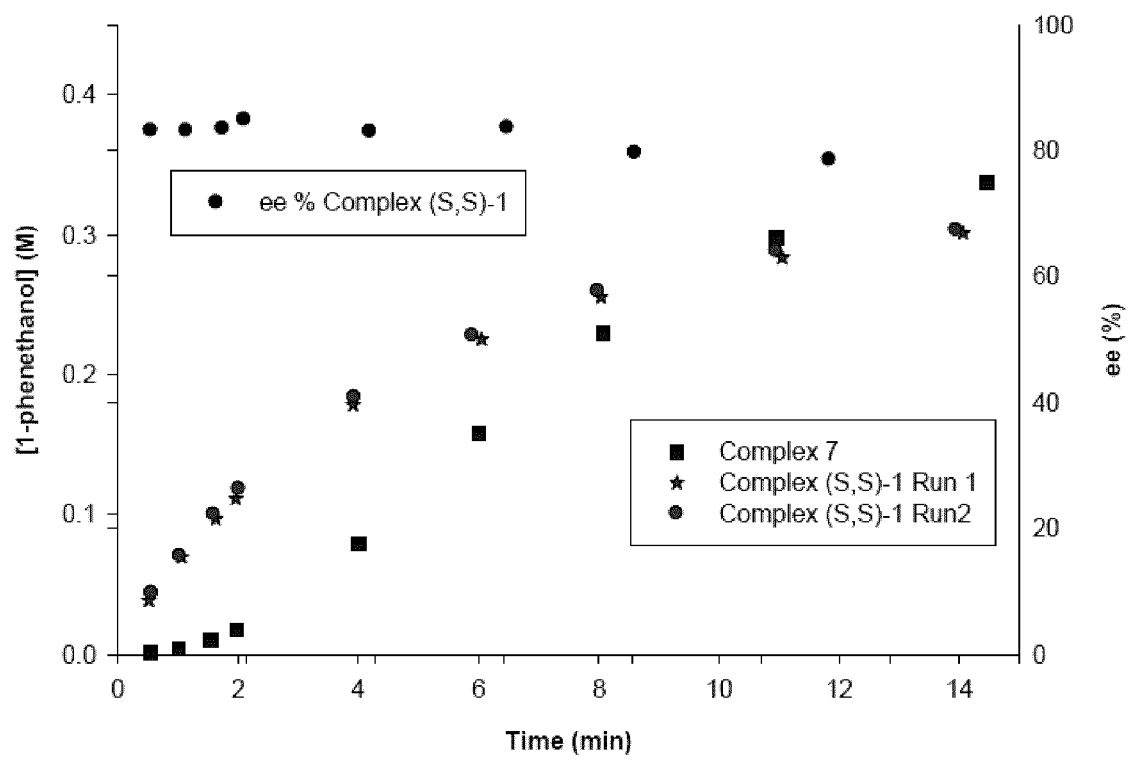
FIG. 2 graphically depicts a reaction profiles of catalytic reduction of acetophenone using complexes (S,S)-7 and (S,S)-1 under standard conditions.

The use of complex (S,S)-1 as a catalyst precursor under the standard conditions results in the rapid catalytic reduction of acetophenone without an induction period as shown in FIG. 2. Complex (S,S)-1 is found to catalyze the reduction of acetophenone with turnover frequency of 55,000 h$^{-1}$ at 25% conversion under conditions where known precatalyst (S,S)-7 gives 30,000 h$^{-1}$. The enantiomeric excess of formed 1-phenylethanol was found to be 82% when the reaction was catalyzed by complexes (S,S)-1 or (S,S)-7.

TABLE 2

Catalyst activity at 30° C. in basic isopropanol ([iPrOH] = 12.5M)

| Complex | [Acetophenone] (M) | Complex (M) × 10$^{-5}$ | [KOtBu] (M) × 10$^{-4}$ | Maximum rate (M/min) × 10$^{-2}$ | e.e |
|---|---|---|---|---|---|
| (S,S)-7 (standard conditions) | 0.412 | 6.74 | 5.45 | 3.53 | 82% |
| (S,S)-1 (Run 1) | 0.412 | 6.76 | 5.45 | 5.02 | 82% |
| (S,S)-1 (Run 2) | 0.412 | 6.76 | 6.46 | 5.14 | 82% |
| (S,S)-8 | 0.412 | 6.76 | — | 5 | 82% |
| (S,S)-4 | 0.868 | 3.10 | 2.59 | 58 | |
| (S,S)-9 | 0.412 | 6.76 | 5.45 | 0.2 | 64% |
| 20 | 0.41 | 6.43 | 7.62 | 9.8 | |

B. Catalytic Reduction of Acetophenone Using Complex (S,S)-8: Mechanistic Investigations Compound (S,S)-8 was directly reacted with a mixture of the acetophenone in iPrOH (standard conditions applied) without the addition of base to test whether it is within the catalytic cycle.

Run 1: A solution of acetophenone (0.476 g, 3.96 mmol) in iPrOH (7.192 g) was prepared in an argon glovebox and the temperature of the solution equilibrated to 28° C. The solution was added to the vial with complex (S,S)-8 to initiate the reaction. The reaction progress was monitored by taking samples of the reaction mixture and quenching them by injection into aerated iPrOH in a sealed GC vial.

Run 2: The solvent iPrOH (7.192 g) was thermostatted at 28° C. and added to the vial containing complex (S,S)-8 and stirred for 4 min. Acetophenone (0.476 g, 3.96 mmol) was added to the reaction mixture to initiate the reaction. The reaction progress was monitored in a similar fashion as in Run 1.

Run 3: Acetophenone (0.476 g, 3.96 mmol) was thermostatted at 28° C. and added to the vial containing complex (S,S)-8 and stirred for 4 min. Isopropanol (7.192 g) was added to the reaction mixture to initiate the reaction. The reaction progress was monitored in a similar fashion as in Run 1.

Run 4: Same as Run 2, but the activation reaction with iPrOH was left for 12.4 min before adding the substrate.

Figure 3:
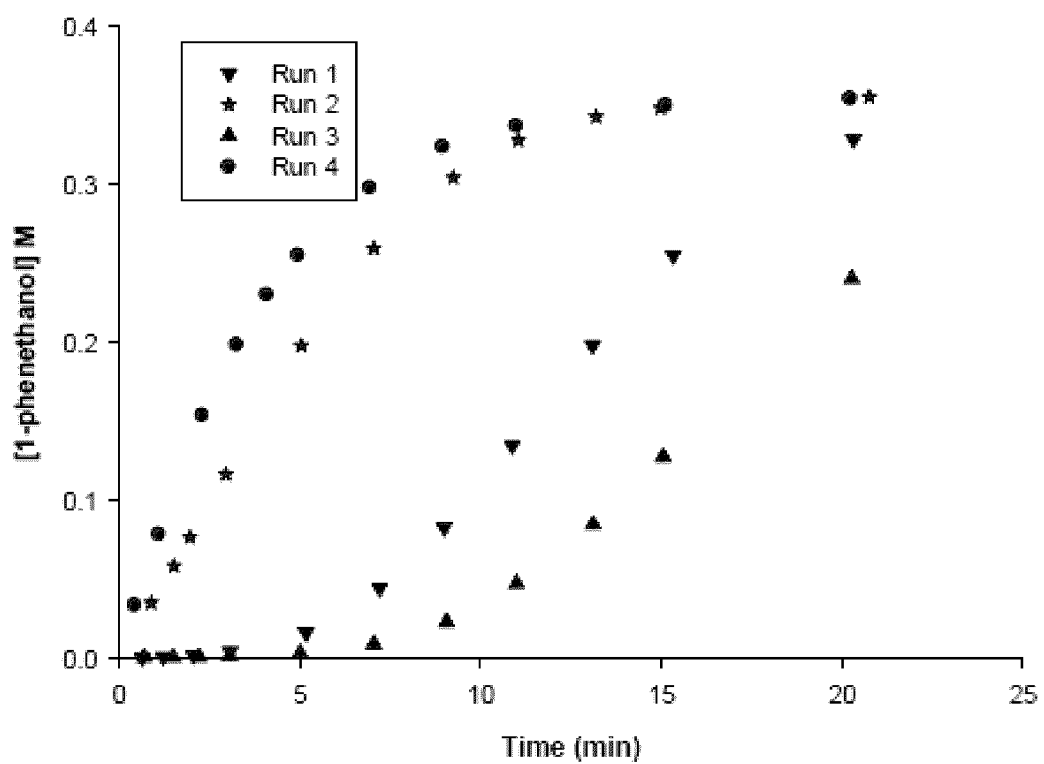
FIG. 3 graphically depicts the catalytic reduction of acetophenone using complex (S,S)-8.

The observed reaction profile in terms of the formation of 1-phenylethanol with time is presented in FIG. 3. The reactivity and enantioselectivity of the complex (S,S)-8 in the process of acetophenone reduction are comparable to these observed with complex (S,S)-7 activated by base. On the other hand, the apparent activation period indicates that complex (S,S)-8 needs to be activated prior to the catalytic cycle to take place; thus it is not within the catalytic cycle.

Since the reaction of complex (S,S)-8 with iPrOH and acetophenone led to the formation of the active catalyst (FIG. 3, Run 1), it can be concluded that one of these reagents is responsible for the activation of (S,S)-8. Each was reacted with the complex (S,S)-8 for four minutes prior to the addition of the other in order to identify, which of the two substances is an activating agent (FIG. 3, Run 2 and Run 3, respectively). The induction period disappeared when (S,S)-8 is pre-reacted with iPrOH (Run 2) but is very pronounced when acetophenone is reacted with (S,S)-8 before iPrOH is added (Run 3). These observations show that the activation of the green complex (S,S)-8 results from its reaction with iPrOH. The longer induction period of Run 3 relative to Run 1 (FIG. 2) is consistent with the finding of the kinetic study that the enolate of acetophenone prolongs the period of activation of the catalyst.

The kinetic studies also predict that the formation of the active species in the solution is a continuous process that takes place during the entire acetophenone reduction step of the reaction. This implies that the concentration of the active catalytic species and the rate of 1-phenylethanol formation will be greater if the pre-activation of the green compound (S,S)-8 with iPrOH is allowed to occur for a longer period of time, keeping other conditions the same. The reaction where (S,S)-8 is pre-activated with iPrOH for 12 min (FIG. 3. Run 4) verifies that this is the case.

C. Catalytic Reduction of Acetophenone Using Complex (S,S)-4

Figure 4:
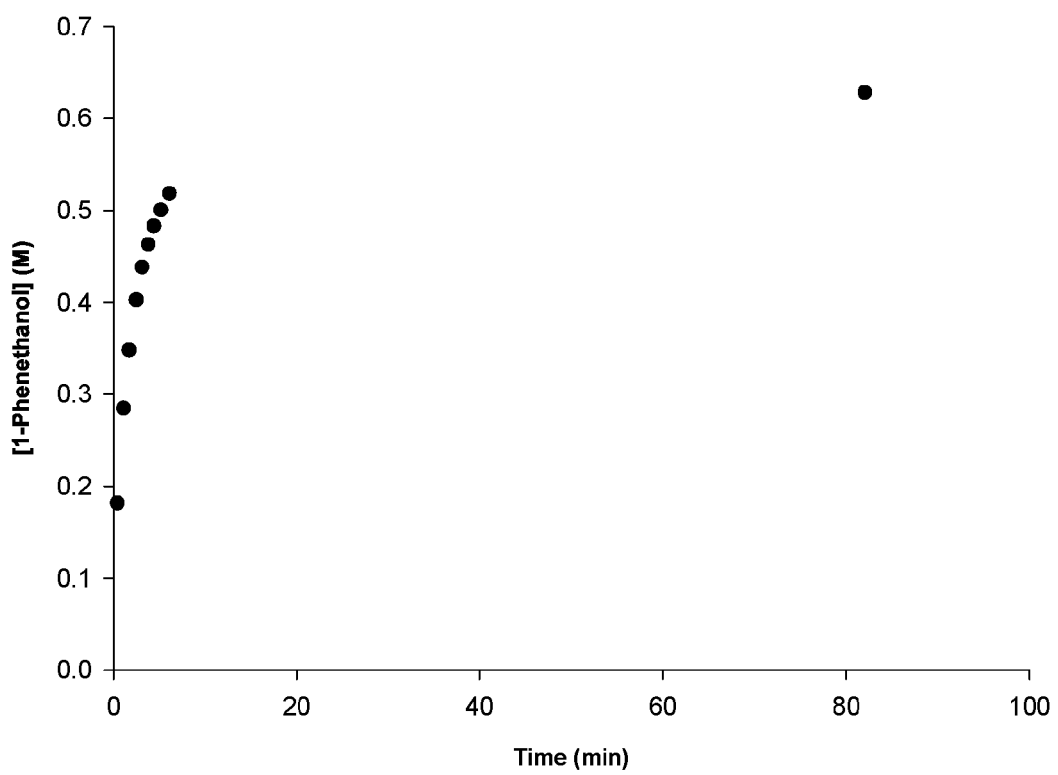
FIG. 4 graphically depicts the mixture of diastereomers of complex (S,S)-4 in the transfer hydrogenation of acetophenone in basic 2-PrOH.

The mixture of diastereomers of complex (S,S)-4 was tested as a catalyst for the transfer hydrogenation of acetophenone in basic 2-PrOH. These results are plotted in FIG. 4. The maximum rate of conversion of acetophenone to 1-phenylethanol is observed in the first minute of the reaction. This indicates that the activation of (S,S)-4 to an active species upon reaction with base is a fast process compared to a slow activation of the precatalysts containing diimine functional groups in the ligand (second generation). The initial turn over frequency (TOF) of (S,S)-4 was determined at 20% of conversions and is equal to 620 000 h$^{-1}$. Conditions: [acetophenone]=0.868 M, [5]=3.10×10$^{-5}$ M, [KO$^t$Bu]=2.59×10$^{-4}$ M, [2-PrOH]=11.8 M.

M1 and M2 were placed into a temperature stirring control unit (IKA RSCT basic) for 15 minutes. To initiate the reaction, M1 and M2 were efficiently mixed by transferring the solutions from vial to vial. The final concentrations of the reagents were adjusted to be as follows: [acetophenone]=0.868 M, [(S,S)-4]=3.07×10$^{-5}$ M, [KOtBu]=2.59×10$^{-4}$ M and [i-PrOH]=11.8 M. The samples were taken and analyzed as described above.

D. Catalytic Reduction of Acetophenone Using Complex (R,R)-9

Figure 5:
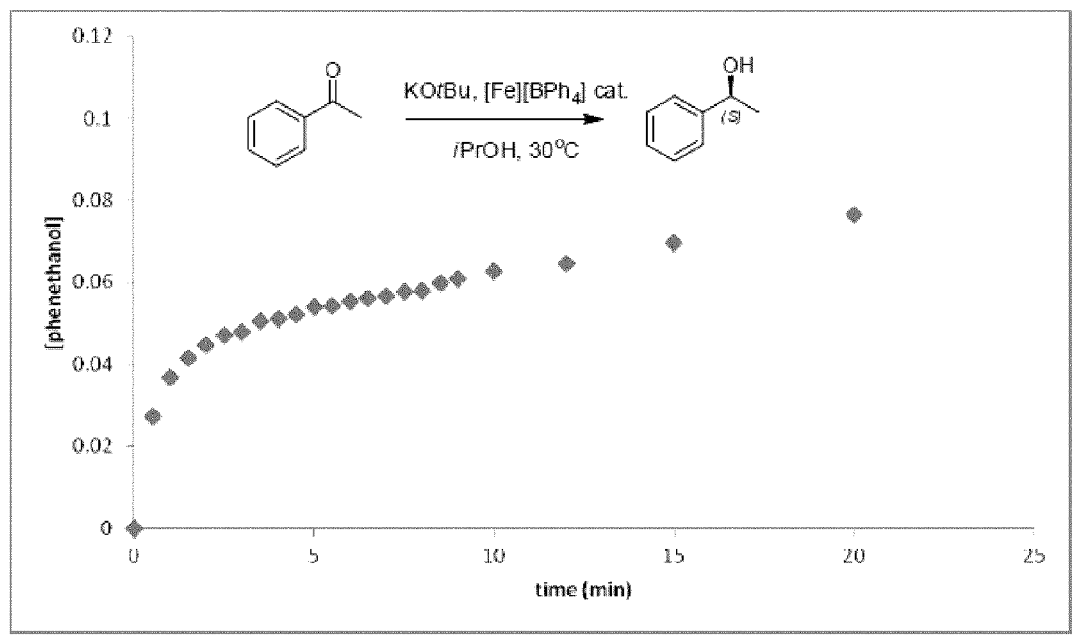
FIG. 5 graphically depicts the catalytic reduction of acetophenone using complex (S,S)-9.
Figure 6:
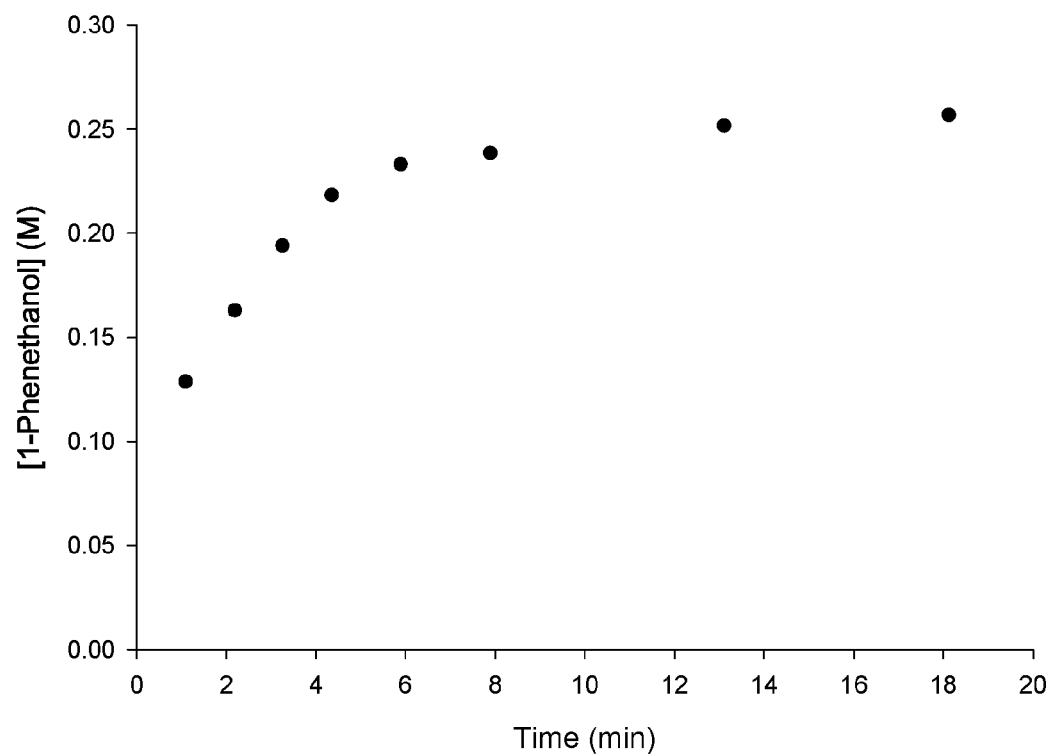
FIG. 6 graphically depicts the catalytic reduction of acetophenone using iron based precatalyst 20.

A vial was charged with 0.11 g of a cat. stock solution (10 mg compound 8 in 0.56 g acetophenone), 0.53 g acetophenone and 8 g isopropanol. To this vial, 0.08 g of a base stock solution (10 g KOtBu in 1 g iPrOH) and 0.5 g iPrOH was added via syringe to initiate catalysis. (C/B/S=1/8/3000). The samples were taken and analyzed by GC as described above. The results are shown in FIG. 5.

1-phenylethanol was produced in 22% conversion after 25 min with an ee of 64%. This is the same enantiomeric excess observed by use of the bisimine precatalyst [Fe(CO)(Br)(PPh$_2$CH$_2$CH=N—(R,R)—C$_6$H$_{10}$N=CHCH$_2$PPh$_2$)] (BPh$_4$) ((R,R)-11, see Mikhailine, A. A.; Morris, R. H. Inorg. Chem. 2010, 49, 11039-11044) However, the initial activity of complex (R,R)-9 is much higher, since the Scheme 24: The transfer hydrogenation of acetophenone using (S,S)-4 as a catalyst

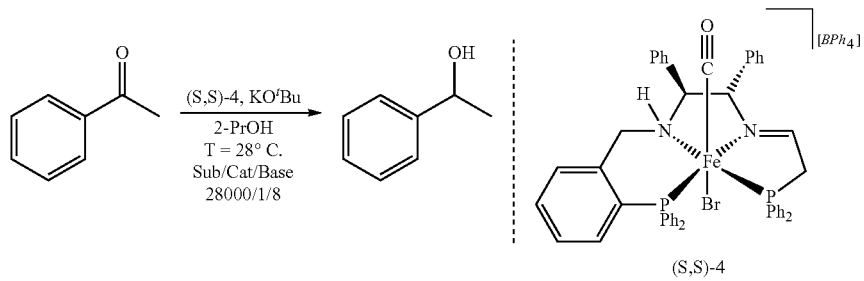

The stock solutions were prepared in a glovebox. The stock solution 1 (SS1) was prepared by dissolving the precatalyst (S,S)-4 (m=0.011 g) in acetophenone (1.531 g). The stock solution 2 (SS2) was prepared by dissolving KOtBu (0.010 g) in i-PrOH (1.022 g). The solutions were used only after all the solids were completely dissolved and for less than two days. SS1 (0.051 g) was added to a vial charged with a stirring bar containing i-PrOH (m=6.606 g) and acetophenone (m=1.004 g) to form mixture 1 (M1). SS2 (m=0.030 g) was added to a second vial containing i-PrOH (m=0.504 g) to give mixture 2 (M2). In order to ensure a constant temperature of the experiment inside a glovebox, bisimine precatalyst (R,R)-11 has an activation period. Complexes of this type with a diaminocyclohexane backbone typically show lower activity than the stilbenyl backbone of catalysts like (S,S)-1. However this catalytic run is further evidence that the use of the imineamine tetradentate ligand, like that of (S,S)-1 or (R,R)-9 leads directly to the catalytically active species without an induction period unlike the bisimine precatalysts (S,S)-7 and (R,R)-11, respectively.

E. Catalytic Reduction of Acetophenone Using Iron Based Precatalyst 20

Scheme 25: Catalytic reduction of acetophenone using precatalyst 20

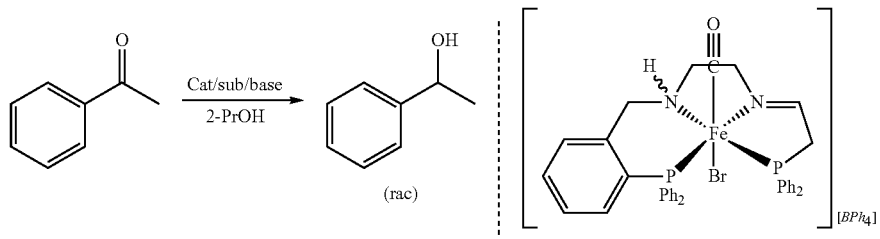

The stock solutions were prepared in a glovebox. The stock solution 1 (SS1) was prepared by dissolving the precatalyst 20 (m=0.010 g) in acetophenone (1.527 g). The stock solution 2 (SS2) was prepared by dissolving KOtBu (0.010 g) in iPrOH (1.022 g). These solutions were used only after all the solids were completely dissolved and for less than two days. SS1 (0.098 g) was added to a vial charged with a stirring bar containing iPrOH (m=6.631 g) and acetophenone (m=0.379 g) to form mixture 1 (M1). SS2 (m=0.085 g) was added to a second vial containing iPrOH (m=0.516 g) to give mixture 2 (M2). In order to ensure a constant temperature of the experiment inside a glovebox, M1 and M2 were placed into a temperature stirring control unit (IKA RSCT basic) for 15 minutes.

To initiate the reaction, M1 and M2 were efficiently mixed by transferring the solutions from vial to vial. The final ratios of components of the reaction were as follows: Conditions: cat:base:sub=1:11:6400; the final concentrations of the reagents were adjusted to be as follows [acetophenone]= 0.410 M, [20]=6.43×10$^{-5}$ M, [KOtBu]=7.62×10$^{-4}$ M and [iPrOH]=12.4 M. V (iPrOH)=9.7 (mL); Temperature=34-35° C.

The samples were taken and analyzed by GC as described above. The results of the catalytic run are represented in FIG. 5. The initial turn over frequency (TOF) (at 30% conv)=1.05×10$^5$ (h$^{-1}$). However this activity is only sustained for the first 30% conversion. Activity drops off to a lower level after a few minutes but still proceeds.

Example 3

Asymmetric Transfer Hydrogenation of Ketimines

Complex (S,S)-1 can catalyze the ketones and imines in the same fashion reported for complex (S,S)-7. Indeed the complexes as presently described can be used in transfer hydrogenation of ketimines to secondary amines with good enantioselectivity according to the following scheme:

Scheme 26: Transfer Hydrogenation of Imines

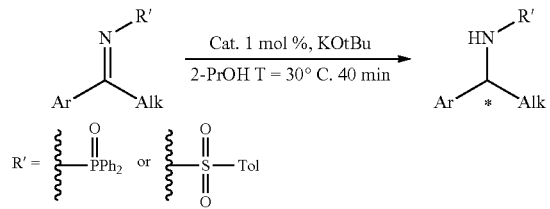

Example 4

Catalytic Reduction of Trans-4-Phenyl-3-Buten-2-One

The complex (S,S)-1 was used to catalyze the reduction of trans-4-phenyl-3-buten-2-one. The reaction was performed using 6.48×10$^{-7}$ mol of complex (S,S)-1 in 8 mL of 2-propanol with 8 equivalents of KO$^t$Bu and 6100 equivalents of substrate at a temperature of 30° C. The results of are provided in the table below.

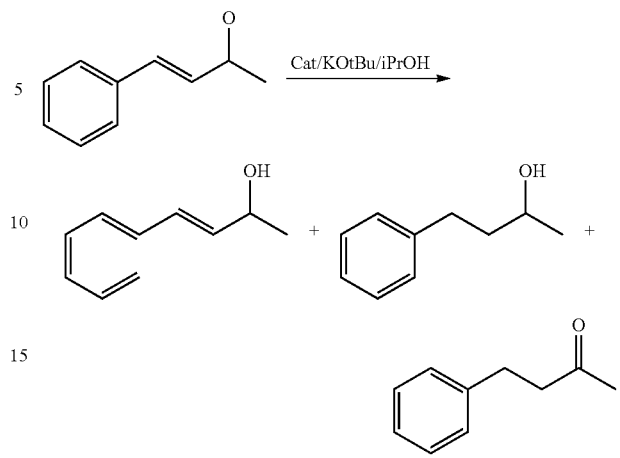

| Time (min) | Conv (%) ee (%) | Conv (%) ee (%) | Conv (%) ee (%) |
|---|---|---|---|
| 4 | 56.0 45.0 | 0 | 1 |
| 20 | 58.5 28.5 | 6.58 rac | 1 |
| 120 | 59.5 rac | 12.87 rac | 1 |

Example 5

Catalytic Asymmetric Reduction—Mechanistic Study

Promising results in the asymmetric transfer hydrogenation of ketone and imines by use of iron(II) complexes with the PNNP ligands containing two imine and two phosphorous functionalities ((R,R)-24 and (S,S)-7, Chart 1) have been previously reported. (Sui-Seng, C.; Freutel, F.; Lough, A. J.; Morris, R. H. Angew. Chem., Int. Ed. 2008, 47, 940; Meyer, N.; Lough, A. J.; Morris, R. H. Chem. Eur. J. 2009, 15, 5605; Mikhailine, A.; Lough, A. J.; Morris, R. H. J. Am. Chem. Soc. 2009, 131, 1394; Lagaditis, P. O.; Lough, A. J.; Morris, R. H. Inorg. Chem. 2010, 49, 10057; and Sues, P. E.; Lough, A. J.; Morris, R. H. Organometallics 2011, 30, 4418) The first generation of these iron catalysts (24, Chart 1) is very active at room temperature (2600 h$^{-1}$ turnover frequency (TOF)) for acetophenone transfer hydrogenation to 1-phenylethanol in 63% ee using isopropanol as the reductant. The second generation of these iron catalysts ((S,S)-7, Chart 1), which still maintain the key phosphorus and nitrogen PNNP chelates but have smaller chelate ring showed exceptionally high activity and enantioselectivity in the catalytic reduction of ketones; a TOF up to 30 000 h$^{-1}$ and enantioselectivity up to 90% for acetophenone reduction can be obtained by varying the substituents on the phosphorus atoms.

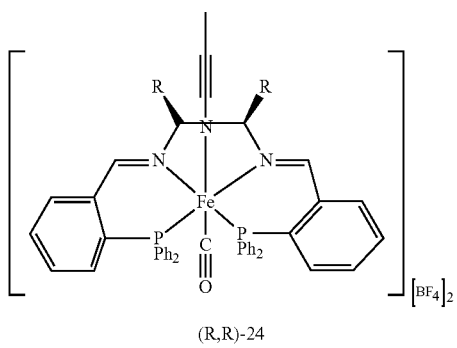

(R,R)-24

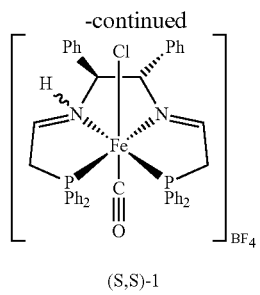

(S,S)-1

Chart 1. Our Three Generations of Active Asymmetric Transfer Hydrogenation Catalysts The mechanism of the asymmetric hydrogen transfer from isopropanol to acetophenone catalyzed by an iron(II) complex [Fe(CO)(Br)(P,N,N,P)]BPh$_4$ ((S,S)-7) with an enantiopure P,N,N,P ligand (S,S)—{PPh$_2$CH$_2$CH=NCHPh-}$_2$ has been studied. (Mikhailine, A. A.; Maishan, M. I.; Lough, A. J.; Morris, R. H. *J. Am. Chem. Soc.* 2012, 134, 12266) These studies showed that the slow step was the activation of the catalyst by reduction of the ligand to a P,N(H),N,P form (S,S)—{PPh$_2$CH$_2$CH$_2$NHCHPhCHPhNCH=CHPPh$_2$} in trans-Fe(H)(P,NH,N,P)(CO) ((S,S)-3) followed by rapid catalysis (Scheme 27). The turnover frequency in the time range of the maximum rate was $3 \times 10^4$ h$^{-1}$ when the solvent was isopropanol containing KO$^t$Bu at 30° C. The high activity is significant since it compares to the current best catalysts for this process, which utilize expensive, rare and toxic platinum metals like ruthenium and iridium.

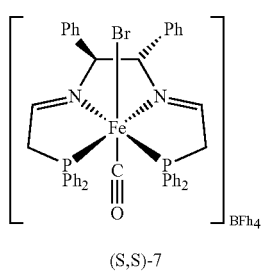

(S,S)-7

Scheme 27: The proposed mechanism for the asymmetric hydrogenation of acetophenone by transfer from isopropanol catalyzed by an iron(II) system produced by activation of complex (S,S)-7 with isopropoxide

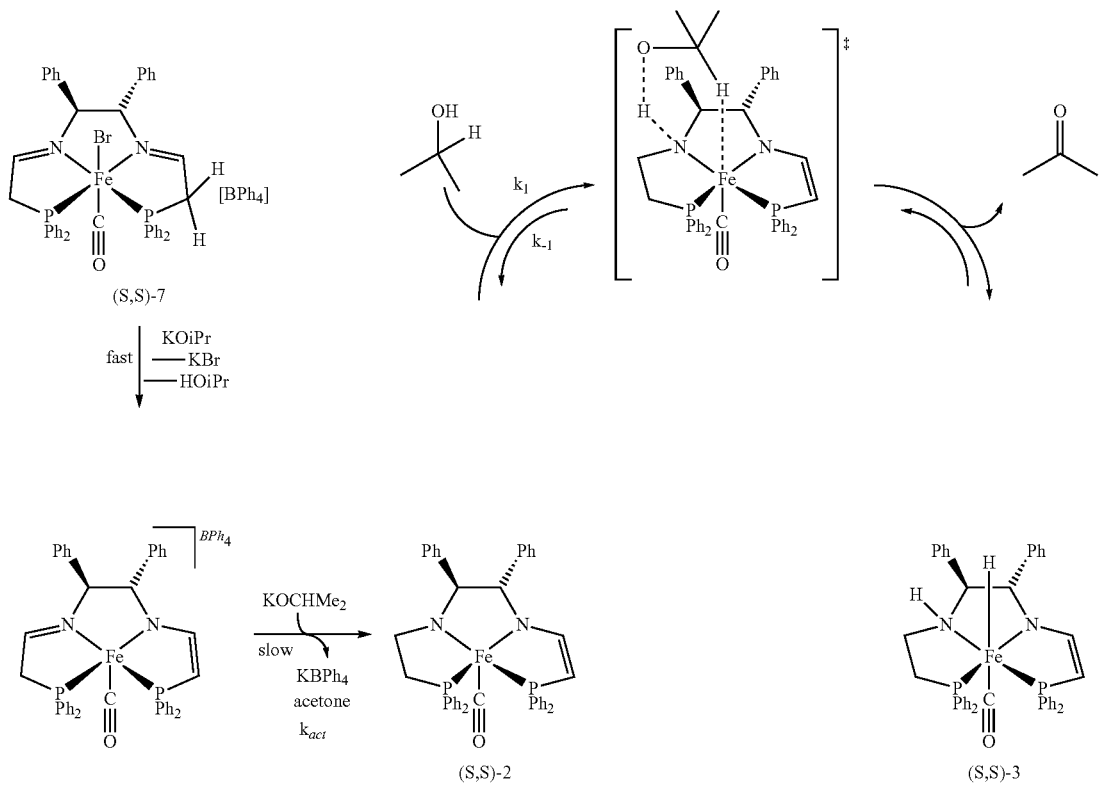

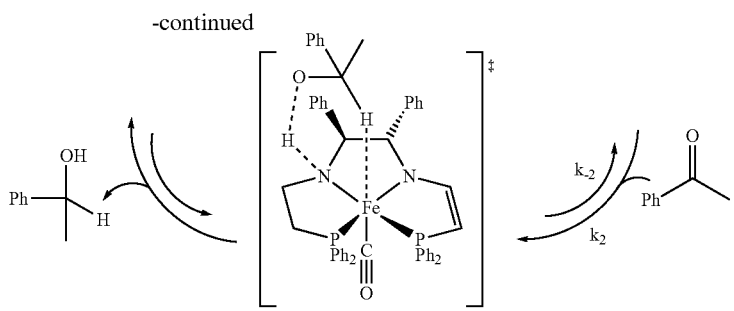

Density functional theory (DFT) studies on the transfer hydrogenation catalyzed by Fe(II) PNNP bis(ene-amido) model complexes have revealed a stepwise inner sphere activation step where a hydride is transferred from isopropyl alcohol to an imine carbon on the ligand to form the unsymmetrical amido-(ene-amido) active species. The calculated free energy barrier of this step was found to be the highest along the whole catalytic reaction coordinate. The catalytic cycle operates via a stepwise outer-sphere mechanism where an $H^+/H^-$ pair is transferred across the amido nitrogen and iron atom, respectively, with the rate-limiting step being hydride transfer to/from isopropyl alcohol/acetophenone. (Prokopchuk, D. E.; Morris, R. H. Organometallics 2012, 31, 7375)

In this Example, the direct synthesis of the iron hydride complex (S,S)-3 (Scheme 27 above) and the iron amide complex (S,S)-2 and a precursor complex ((S,S)-1, Chart 1) are reported, which lead directly to these catalytically competent and enzyme-like complexes.

Experimental and Results:

Reduction of acetophenone and other ketone substrates using iron-based complexes (S,S)-1 and (S,S)-1tol.

The procedures for the transfer hydrogenation using complexes (S,S)-1 and (S,S)-1tol as catalyst precursors were similar to those that are described in previous examples. Stock solution 1 (SS1) was prepared by measuring a certain quantity of the complex into a small vial and then dissolving it in 3.04 g of dichloromethane (DCM). The stock solution 2 (SS2) was prepared by dissolving KO$^t$Bu in iPrOH. These solutions were used only after all the solids were completely dissolved and were stored for less than two days. The pre-calculated mass of stock solution 1 was measured into a vial and the DCM was evaporated to obtain a yellow solid. The required mass of the substrate was then added to a measured mass of isopropanol to get mixture 1 (M1). A required mass of SS2 was added to a second vial containing iPrOH to give mixture 2 (M2). To initiate the reaction, M1 and M2 were efficiently mixed by transferring the solutions from vial to vial. The final concentrations of the reagents were adjusted to be as follows: [Cat. (S,S)-1]=$6.73\times10^{-5}$ M, [KOtBu]=$5.45\times10^{-4}$ M, [substrate]=0.412 M, [iPrOH]=12.4 M, 28° C. The samples were taken by injecting small portions of the reaction mixture into septa-sealed GC vials containing aerated iPrOH for efficient quenching of the reaction. Samples were analyzed using a Perkin-Elmer Autosystem XL chromatograph with a chiral column (CP chirasil-Dex CB 25 m×2.5 mm). Hydrogen gas was used as a mobile phase at a column pressure of 5 psi. The injector temperature was 250° C., and the FID temperature was 275° C. The amount of reduced alcohol in the sample was determined relative to the amount of the substrate.

In the presence of 8 equiv of KO$^t$Bu at room temperature, complex (S,S)-1tol was an extremely efficient catalyst for the asymmetric transfer hydrogenation of acetophenone. No induction period was observed unlike previous catalysis with previous catalyst precursors that have been reported. (Mikhailine, A.; Lough, A. J.; Morris, R. H. J. Am. Chem. Soc. 2009, 131, 1394; and Mikhailine, A. A.; Maishan, M. I.; Lough, A. J.; Morris, R. H. J. Am. Chem. Soc. 2012, 134, 12266) The observed reaction profile in terms of the formation of 1-phenylethanol with time and the change of ee with time is presented in FIG. 8. The TOF of 550,000 h$^{-1}$ at 50% conversion was notable and it took less than 180 seconds for the reaction to reach equilibrium at a maximum turnover number (TON) of 6100. To the best of the inventors' knowledge this is the most active transfer hydrogenation system at this temperature. (Junge, K.; Schroeder, K.; Beller, M. Chem. Commun. 2011, 47, 4849; Sui-Seng, C.; Freutel, F.; Lough, A. J.; Morris, R. H. Angew. Chem., Int. Ed. 2008, 47, 940; Baratta, W.; Chelucci, G.; Gladiali, S.; Siega, K.; Toniutti, M.; Zanette, M.; Zangrando, E.; Rigo, P. Angew. Chem., Int. Ed. 2005, 44, 6214; Zweifel, T.; Naubron, J.-V.; Buettner, T.; Ott, T.; Gruetzmacher, H. Angew. Chem., Int. Ed. 2008, 47, 3245; Thoumazet, C.; Melaimi, M.; Ricard, L.; Mathey, F.; Le Floch, P. Organometallics 2003, 22, 1580; Baratta, W.; Herdtweck, E.; Siega, K.; Toniutti, M.; Rigo, P. Organometallics 2005, 24, 1660; and Del Zotto, A.; Baratta, W.; Ballico, M.; Herdtweck, E.; Rigo, P. Organometallics 2007, 26, 5636)

The initial turnover frequency ($7.3\times10^6$ h$^{-1}$) was close to the previous theoretical prediction ($1.1\times10^7$ h$^{-1}$), which was equal to an activation free energy barrier of 13.4 kcal/mol of the catalytic cycle. (Prokopchuk, D. E.; Morris, R. H. Organometallics 2012, 31, 7375) The observed higher activity compared to the previous PNNP system, was attributed to the disappearance of the long-term induction period during which the slowest step was the activation of the catalyst precursor by the reduction of the PNNP ligand to an unsymmetrical P—N—NH—P ligand. This activation reaction was found to occur throughout the whole catalysis and the formation of the active catalyst is a continuous process. In addition, side reactions were also found during the induction period. (Mikhailine, A. A.; Maishan, M. I.; Lough, A. J.; Morris, R. H. J. Am. Chem. Soc. 2012, 134, 12266) All of these factors may lead to only partial transformation of the catalyst precursor to the real active species, while most of the catalyst related species are staying in the resting state or outside of the catalytic cycle. In comparison, the current P—N—N—P catalyst precursors were activated instantaneously without an induction period and, as discussed below, the generated active species can directly enter the catalytic cycle without obvious side reactions under optimistic conditions.

Figure 8:
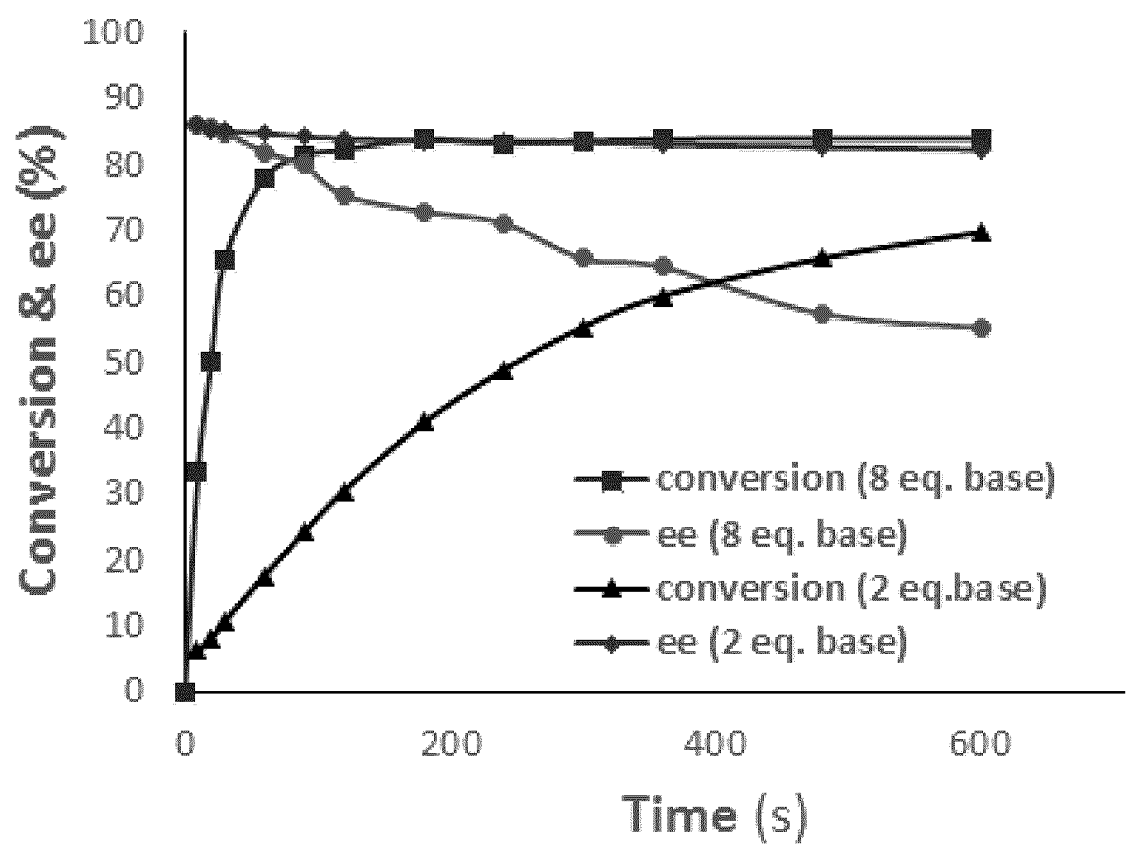
FIG. 8 graphically depicts the reaction profile of catalytic reduction of acetophenone using complex (S,S)-1tol as catalyst (reaction conditions: catalyst=$6.48\times10^{-5}$M, [KO$^t$Bu]=$5.45\times10^{-4}$M, [substrate]=0.412 M, [$^i$PrOH]=12.4 M (8 mL), (catalyst/KO$^t$Bu/substrate=1/8.4/6358, 28° C.)
Figure 9:
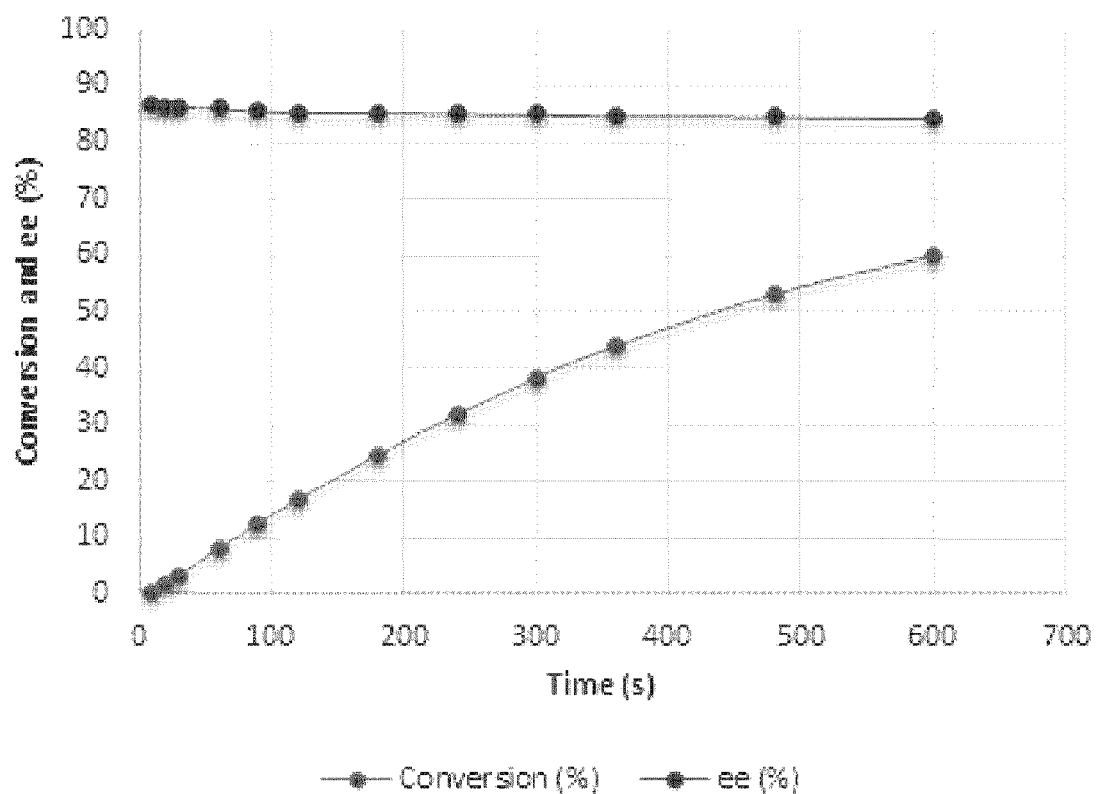
FIG. 9 graphically depicts the reaction profile of catalytic reduction of acetophenone using complex (S,S)-2 as catalyst in the absence of base.

The enantiomeric excess (ee) of the 1-phenylethanol (R) produced decreased gradually from 86.5% in the initial 10 seconds to 55.1% at 10 min (FIG. 8). Using complex (S,S)-1 as catalyst precursor gave a 2% of higher ee with similar catalytic behavior. The addition of 2 equiv of KO$^t$Bu was enough to activate the catalyst although the catalytic activity was lower, and this was consistent with the previous hypothesis that the neutral iron(II) complex containing an eneamido structure and an amido structure on each sides of the ligand was the active catalyst in the asymmetric transfer hydrogenation of acetophenone (FIG. 8). (Mikhailine, A. A.; Maishan, M. I.; Lough, A. J.; Morris, R. H. *J. Am. Chem. Soc.* 2012, 134, 12266) The decreased activity compared to the 8 equiv of base case was attributed to a major side reaction forming an inactive species that stays outside of the catalytic cycle. This side reaction will be discussed in detail later. In the current case, 2 equiv of base were required to deprotonate the tetradentate backbone in (S,S)-1 and (S,S)-1tol complexes, especially at the amine N and carbon a to the phosphorus to form the unsymmetrical amido-(ene-amido) ligand in a neutral iron(II) complex as we will mention below. However, one advantage of using less base was that the ee did not drop significantly within 10 minutes (FIG. 8). This observation when compared to the above 8 equiv base case indicates that the catalyst causes the very slow racemization of enantiopure 1-phenylethanol in the presence of excess base. In fact, KO$^t$Bu was independently observed to racemize enantiopure 1-phenylethanol in isopropanol.

An inherent drawback of catalytic transfer hydrogenation caused by the thermodynamic factors of the system is the reversibility of the reaction, which prevents complete conversion and can also leads to a deterioration in the enantiomeric purity of the products upon long-term exposure of the reaction mixture to the catalyst. (Ikariya, T.; Blacker, A. J. *Acc. Chem. Res.* 2007, 40, 1300; Gao, J. X.; Ikariya, T.; Noyori, R. *Organometallics* 1996, 15, 1087; Hashiguchi, S.; Fujii, A.; Haack, K. J.; Matsumura, K; Ikariya, T.; Noyori, R. *Angew. Chem., Int. Ed.* 1997, 36, 288; Hashiguchi, S.; Fujii, A.; Takehara, J.; Ikariya, T.; Noyori, R. *J. Am. Chem. Soc.* 1995, 117, 7562; Takehara, J.; Hashiguchi, S.; Fujii, A.; Inoue, S.; Ikariya, T.; Noyori, R. *Chem. Commun.* 1996, 233; and Noyori, R.; Hashiguchi, S. *Acc. Chem. Res.* 1997, 30, 97) The relatively high activity of the current catalyst system and the fact that the ee keeps relatively constant when 2 equiv of base are used makes it possible to overcome such a general limitation. By slightly modifying the catalytic procedure, it was possible to achieve a 99.9% conversion of acetophenone while at the same time the ee of the reduced product was maintained at 82.5%. In the presence of 2 equiv of base, the catalytic reaction was first run for 5 min to a conversion of 71% and an ee of 83.5%, and then the solvent was removed under vacuum. A new portion of solvent of equal volume to the first reaction, together with one additional equiv of catalyst and two equiv of base were added to restart the catalysis, and after 10 seconds all of the remaining substrate was converted while the ee did not change significantly. This procedure would also be practical in similar situations where the substrates cannot be fully converted due to the equilibrium of the reaction.

In the presence of 8 equiv of base, complex (S,S)-1 was broadly reactive towards a series of ketone substrates (i.e., in addition to acetophenone), with from good to high enantioselectivities (Table 3). The reduction of 3,5-bistrifluoromethylacetophenone proceeded with comparable activity to that of acetophenone but with better conversion and enantioselectivity. It is noteworthy that benzylaldehyde was near quantitatively converted at a substrate/catalyst ratio of 6100 within 25 seconds with TOF=870 000 h$^{-1}$. The reaction rate stayed almost constant from the beginning of the reaction until all the substrate was converted. When the reduction of 3-methyl-2-butanone was carried out in the presence of (S,S)-1 and base, the ee value reached 51.9% with 66.8% maximal conversion after 1 h. The reduction of 2-acetonaphthone with (S,S)-1 led to 83.5% conversion and 91.2% ee within 3 min. Of further interest was the observed tolerance to a variety of functional groups; for example 2-acetalpyridine was efficiently reduced to the corresponding alcohol (R) in 95.6% conversion within 4 min. However, the enantioselectivity for this substrate was relatively low. 2-Acetyl furan was also quickly reduced, albeit with a relatively low selectivity. 3,4-Dihydronaphthalen-1-one was converted to the corresponding alcohol less efficiently than acetophenone with a relatively low, but approximately constant, selectivity. When benzophenone was used as the substrate, the corresponding alcohol was obtained in 91% within 20 minutes. In addition, complex (S,S)-1 catalyzed the transfer hydrogenation of N-(diphenylphosphinoyl)-acetophenimine in >99.9% ee, which is 100 times faster than was observed using the previously reported bis(imine) analogue. (Mikhailine, A. A.; Maishan, M. I.; Morris, R. H. *Org. Lett.* 2012, 14, 4638)

TABLE 3

Transfer Hydrogenation of Ketones and Imines Catalyzed by Complex (S,S)-1 prepared by method 3.

| Substrate | Time(s) | Conv(%)$^b$ | TOF (×10$^3$h$^{-1}$)$^c$ | ee % |
|---|---|---|---|---|
| 3,5-bis(trifluoromethyl)acetophenone | 10/20/180 | 33.3/48.7/99.2 | 730/530/120 | 90.3/90.2/90.2 |
| benzaldehyde | 10/25 | 42.1/99.3 | 920/870 | — |
| 3-methyl-2-butanone | 30/1200/3600 | 0.3/57.0/66.8 | 2.2/10/4.1 | 95.5/54.0/48.8 |

TABLE 3-continued

Transfer Hydrogenation of Ketones and Imines Catalyzed by Complex (S,S)-1 prepared by method 3.

| Substrate | Time(s) | Conv(%)[b] | TOF (×10³h⁻¹)[c] | ee % |
|---|---|---|---|---|
| 2-acetonaphthone | 10/20/180 | 35.4/51.5/83.5 | 780/570/100 | 92.3/92.1/76.8 |
| 2-acetylpyridine | 10/60/360 | 36.5/61.0/98.1 | 800/37/60 | 22.5/22.3/22.2 |
| 2-acetylfuran | 10/60/360 | 22.1/59.4/84.2 | 490/217/51 | 50.8/39.6/31.1 |
| benzophenone | 10/90/600 | 12.6/50.3/88.4 | 280/120/32 | — |
| α-tetralone | 10/600/3600 | 1.52/42.6/73.2 | 33/16/4.5 | 34.1/33.3/33.1 |
| N-phosphinyl ketimine [d] | 10 | 99.9 | 36 | >99.9 |

[a]General condition: [(S,S)-1] = 6.73 × 10⁻⁵M, [KO$^t$Bu] = 5.45 × 10⁻⁴M, [substrate] = 0.412M, [$^i$PrOH] = 12.4M, 28° C.;
[b]The initial reaction time, the time at around 50% conversion and the time at the maximal conversion.
[c]Turnover frequency in the beginning, at around 50% and the maximal conversion.
[d]Reaction condition: [(S,S)-1] = 5.89 × 10⁻⁵M, [KO$^t$Bu] = 4.71 × 10⁻⁴M, [imine] = 5.89 × 10⁻³M, [$^i$PrOH] = 12.4M, 28° C.

Mechanistic Studies

To understand the mechanism of these iron-catalyzed transfer hydrogenation reactions in more detail, the isolation and NMR characterization of the possible intermediates was conducted.

(i) Synthesis of Fe(CO)(PPh₂ CH'CHNCH PhCHPhNCH₂CH₂PPh₂) ((S,S)-2)

Complex (S,S)-1 reacted with 2 equiv of KO$^t$Bu in benzene or THF at room temperature quantitatively and cleanly giving the neutral amido-(ene-amido) iron(II) carbonyl complex [Fe(CO)(Ph₂PCH=CH—N—((S,S)—C(Ph)H—C(Ph)H)—N—CH₂CH₂PPh₂)] ((S,S)-2) (Scheme 28) through the deprotonation of the amine group and CH group located α to the phosphorus, as established by a set of NMR spectra (Scheme 11 above).

Scheme 28

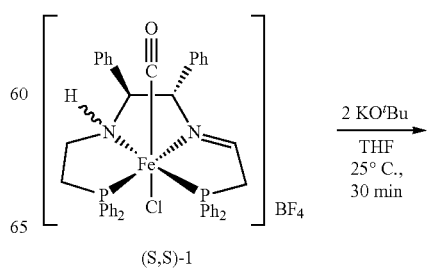

-continued

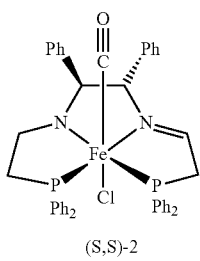

(S,S)-2

A vial was charged with (S,S)-1 (100 mg, 0.120 mmol), KO$^t$Bu (26.7 mg, 0.240 mmol) and THF (5 mL) or benzene (20 mL). The reaction mixture was allowed to stir at room temperature for 30 min (if benzene was used, overnight) to yield a dark purple solution. The solvent was removed under vacuum and the product was dissolved in $C_6D_6$ for NMR analysis. (S,S)-2: $^1$H NMR (400 MHz, $C_6D_6$) δ: 2.03 (m, 1H, PCH$_2$), 2.19 (m, 1H, PCH$_2$), 2.38 (m, 2H, NCH$_2$), 3.88 (dd, 1H, $^3J_{HH}$=5.2 Hz; J$_{HP}$=4.5 Hz, PCH), 4.22 (brs, 1H, —NC (Ph)H, adjacent to amido N atom), 4.70 (brs, 1H, NC(Ph)H, adjacent to ene-amido N atom), 7.70-7.80 (ddd, 1H, $^3J_{HP}$=40.4 Hz, $^4J_{HP}$=2.1 Hz, $^3J_{HH}$=5.1 Hz, NCH). 6.62-7.85 (m, 3H, ArH). $^{13}$C {$^1$H} NMR (100 MHz; $C_6D_6$) δ: 36.3 (d, J$_{CP}$=97.6 Hz, PCH$_2$), 56.3 (NCH$_2$), 71.1 (dd, J$_{CP}$=214.8 Hz, $^3J_{CP}$=24.4 Hz, PCH), 79.3 (NC(Ph)H, adjacent to ene-amido N atom), 89.8 (NC(Ph)H, adjacent to amido N atom), 126.9 (NCH). $^{31}$P {$^1$H} NMR (161 MHz; CD$_2$Cl$_2$) δ: 75.8, 85.3 J$_{PP}$=28 Hz.

The observed absence of fluorine and boron resonances in the $^{19}$F and $^{11}$B spectra, respectively, is consistent with (S,S)-2 being a neutral compound. The $^{31}$P NMR spectrum of (S,S)-2 in $C_6D_6$ provided evidence for two diastereomers in a ratio of 1:20 with the major one displaying two doublets at 75.8 and 85.3 ppm with a $^2$J(P,P) coupling constant of 28 Hz. The resonances of the hydrogens of the (S,S)-stilbenyl (CHPhCHPh) backbone in the $^1$H NMR spectrum of (S,S)-2 in $C_6D_6$ appeared as two broad singlets at 4.22 and 4.70 ppm. These were shifted downfield by 0.28 and 0.76 ppm, respectively, compared to those of (S,S)-1. The $^1$H—H$^1$H COSY results indicate that they are coupled to each other. The proton signal for the —CH$_2$— moiety next to the amido group appears as a upheld-shifted multiplet at 2.38 ppm, whereas the other geminal protons of the CH$_2$ group next to the phosphorus exhibit multiplets at 2.03 and 2.19 ppm. The $^{13}$C {$^1$H} NMR peak of the CH$_2$ moiety next to amido N atom appears at 56.3 ppm and it is shifted downfield relative to that in (S,S)-1. The other CH$_2$ carbon nucleus produces a doublet at 36.3 ppm with J$_{CP}$=97.6 Hz. Similar NMR properties of the ene-amido group were observed in the previously reported bis(ene-amido) complexes. (Lagaditis, P. O.; Lough, A. J.; Morris, R. H. J. Am. Chem. Soc. 2011, 133, 9662) For example, in the $^1$H NMR spectrum, (S,S)-2 showed a characteristic doublet of doublet of doublets signal for the CH proton next to the ene-amido N atom ranging from 7.70-7.80 ppm, with $^3J_{HP}$=40.4, $^3J_{HH}$=5.1 and $^4J_{HP}$=2.1 Hz, respectively. The corresponding carbon nucleus showed a singlet at 126.9 ppm. In the $^1$H NMR spectrum, the CH moiety adjacent to the phosphorus presented a doublet of doublets at 3.88 ppm ($^3J_{HH}$=5.2, J$_{HP}$=4.5 Hz), whereas the carbon resonance appeared at 71.1 ppm as a doublet of doublets (J$_{CP}$=214.8 Hz). Complex (S,S)-2 was highly sensitive to air and such high reactivity prevented the full characterization of this compound using elemental analysis, high resolution mass spectroscopy or X-ray diffraction. The minor isomer showed three distinct resonances at 3.95, 4.42 and 5.25 ppm as small and broad signals in the $^1$H NMR spectrum. The $^{31}$H NMR spectrum displayed two doublets at 77.2 and 82.7 ppm with a $^2$J(P,P) coupling constant of 31 Hz. The two diastereomers may originate from the up/down mixture of the CO ligand relative to the coordination plane or conformations of the 5-membered dpen-Fe backbone.

(ii) Reduction of Acetophenone Using Complex (S,S)-2

Complex (S,S)-2 was used as a catalyst in the reduction of acetophenone according to the following procedure.

The required mass of stock solution 1 was measured into a vial, and then evaporated to obtain a yellow solid. The yellow solid was dissolved in THF to obtain a yellow solution. The required amount of solution 2 was weighed in a vial, and then evaporated to obtain a white solid, to which the yellow THF solution was added. The reaction mixture was stirred at room temperature for 30 min, and then the THF was removed in vacuum to obtain a dark solid. A mixture containing the required amount of substrate and isopropanol was mixed, and this mixture was added to the solid in a vial described above with vigorous stirring. It took only up to 5 s for complex (S,S)-2 to be fully dissolved in the acetophenone/isopropanol mixture and as a result, the effect of the solubility on the reaction profile was negligible. The final concentrations of the reagents were adjusted to be as follows [(S,S)-2]=6.73×10$^{-5}$M, [substrate]=0.412 M, [$^i$PrOH]=12.4 M, 28° C.

Complex (S,S)-2 was found to be a highly active catalyst for the asymmetric transfer hydrogenation of acetophenone to 1-phenylethanol (R) in isopropanol without the addition of base. Approximately 60% of the substrate was reduced at room temperature within 10 min with an 82.4% ee and a remarkably high TOF of 24 000 h$^{-1}$ at 50% conversion. No induction period was observed and the reaction profile was similar to that obtained when only 2 equiv of base were used while other conditions were kept identical to the standard conditions. These observations are consistent with the previous hypothesis that complex (S,S)-2 is the active catalyst for the transfer hydrogenation of ketone substrates using bis(imine) iron(II) carbonyl complex as the catalyst precursor in basic isopropanol. (Mikhailine, A. A.; Maishan, M. I.; Lough, A. J.; Morris, R. H. J. Am. Chem. Soc. 2012, 134, 12266) However, it should be noted that a little variation of this conversion curve relative to that in FIG. 8 where 2 equiv of base was employed, was observed. This likely arose from the different extents to which the side reaction between (S,S)-2 and isopropanol to form inactive species occurred in the presence and absence of acetophenone.

(iii) Synthesis of Trans-[FeH(CO)(Ph$_2$PCH=CH—N—((S,S)—C(Ph)H—C(Ph)H)—NH—CH$_2$CH$_2$PPh$_2$)] ((S,S)-3) in Basic Isopropanol.

Scheme 29. Generation of (S,S)-3 from (S,S)-2

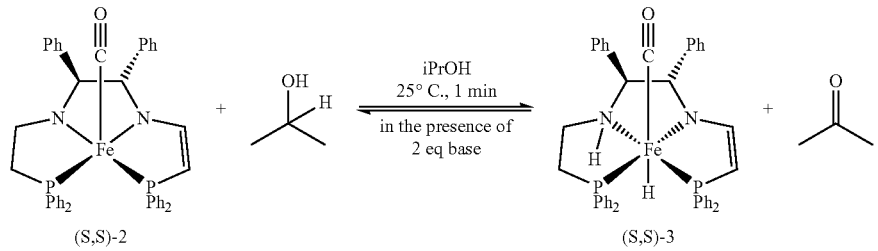

Further reaction of this amido-(ene-amido) complex (S,S)2 with isopropanol in isopropanol in the presence of an additional 2 equiv of KO$^t$Bu at room temperature over a short period of 1 min led to the formation of an amine iron hydride complex (S,S)-3 which shows a characteristic doublet of doublet hydride resonances at −2.3 ppm (dd, J$_{HP}$=70, 70.8 Hz) in $^1$H nmr and two coupling doublets (70.4, 84.9, J$_{PP}$=33.2 Hz) in the $^{31}$P NMR spectrum. More detailed $^1$H NMR data of this hydride complex: $^1$H NMR (600 MHz, CD$_6$D$_6$) δ: 3.8 (dd, J$_{HH}$=10.4, 10.8 Hz, —CH(Ph) amine part), 4.6 (d, J$_{HH}$=10.4 Hz, —CH(Ph) ene-amido part), 7.75 (ddd, $^3$J$_{HP}$=40.4 Hz, $^3$J$_{HH}$=5.4 Hz, $^4$J$_{HP}$=2.2 Hz, —NCH=CH), 4.35 (m, —CH=CHP), 4.0 (m, NH).

However, such hydride species can only survive for 5 min at room temperature in deuterated benzene and isomerized to another hydride analogue which is more stable. $^1$H NMR of this new hydride complex: $^1$H NMR (600 MHz, CD$_6$D$_6$) δ: 2.77 (dd, J$_{HH}$=10.4, 10.8 Hz, —CH(Ph) amine part), 4.36 (d, J$_{HH}$=10.4 Hz, —CH(Ph) ene-amido part), 7.70 (ddd, $^3$J$_{HP}$=40.1 Hz, $^3$J$_{HH}$=5.1 Hz, $^4$J$_{HP}$=2.2 Hz, —NCH=CH), 4.87 (m, NH), 4.43 (m, —CH=CHP), −9.1 (dd, J$_{HP}$=78.6, 79.8 Hz, hydride). $^{31}$P {$^1$H} NMR (243 MHz; CD$_6$D$_6$) δ: 71.4, 75.7, d, J$_{PP}$=27.5 Hz.

Synthesis of the Hydride Complexes

Isopropanol (2 mL) was added into the vial charged with complex (S,S)-2 (0.01 mmol) obtained from the last step, and the resultant solution was stirred at room temperature for 1 min. The solvent isopropanol was immediately removed under vacuum to obtained a slightly red powder, which was extracted with C$_6$D$_6$ for the NMR analysis. The second hydride complex was observed by leaving the first hydride in C$_6$D$_6$ over 10 min at room temperature.

NOESY experiment on this relatively more stable species revealed that the amino N—H and the hydride were on the same side of the coordination plane, which is different from the case of the starting precatalyst. We propose that these two hydrides are a couple of isomers originating from the rotation of C—C bonds of the dpen backbone. One of the hydride complex has an axial disposition of the two phenyl groups of the dpen backbone and the other has the equatorial configuration. Similar isomerization were observed in the BPh$_4$ analogue of (S,S)-1-tol.

More importantly, the reaction of both hydride species in deteurated benzene with added acetophenone produced phenylethanol accompanied by the disappearance of both the hydride $^1$H NMR and the corresponding $^{31}$P NMR signals. This indicates that these hydride species act as reactive reductants of the acetophenone in the catalytic reactions.

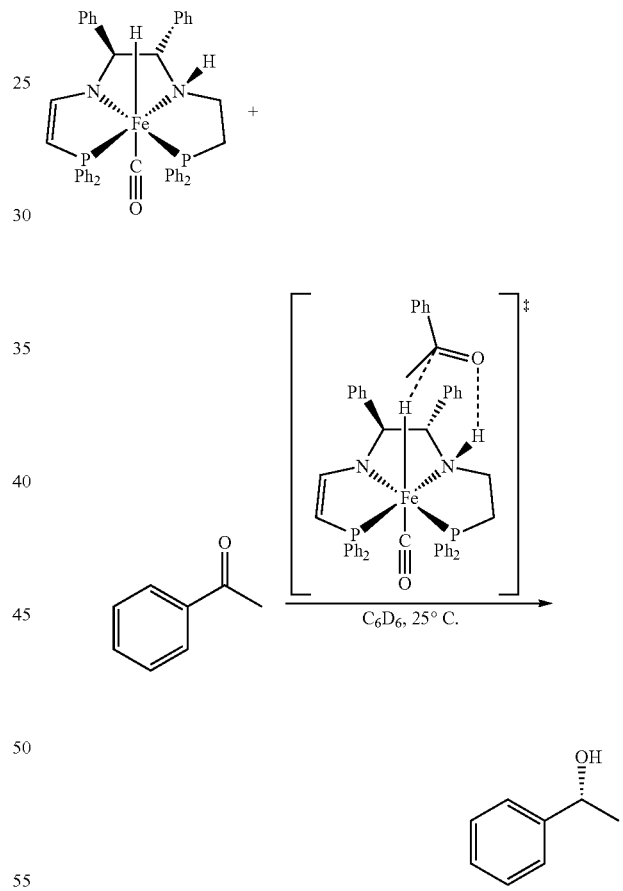

Scheme 30. The reaction of (S,S)-3 with acetophenone to give phenylethanol

In summary, the imine-amine iron carbonyl complexes are extremely efficient pre-catalysts for the asymmetric transfer hydrogenation of a series of prochiral ketone and imine substrates to give valuable chiral alcohols and amines. Mechanistic studies based on the isolation of reactive intermediates of each single step along catalytic cycle and stoichiometric reaction studies of each immediate confirmed our previously proposed mechanism.

Scheme 30. The reaction of (S,S)-3 with ketone to give (S,S)-2-acetophenone

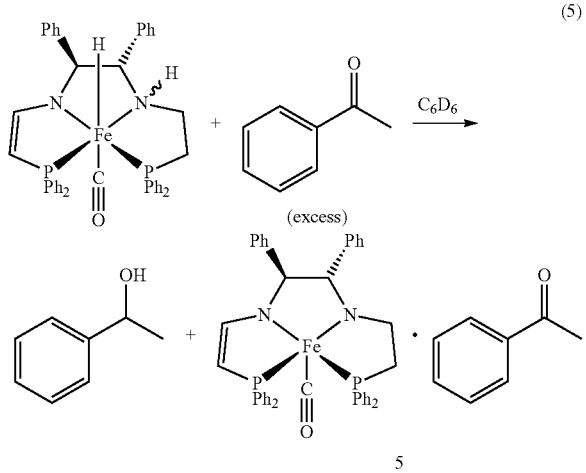

In conclusion, the presently described iron complexes are highly efficient catalysts for the asymmetric transfer hydrogenation of ketones and imine that have useful, exceptionally high activity and enantioselectivity in the production of various valuable enantioenriched alcohols and amines. The first key to success is the combination of both amine and imine functionalities in the PNN(H)P ligand backbones, which can be deprotonated to form an active neutral amido-(ene-amido) carbonyl iron(II) complex. The relatively simple and fast acid-base neutralization reaction in the precatalyst activation step facilitates clean and full transformation of the catalyst precursor, thus, maximizing the concentration of the active catalysts. The reactivity of the observed hydride complex is consistent with the proposed outsphere reduction of the ketone.

As detailed in previous Example 1, in order to synthesize the catalyst precursor of desired structure, the present application describes for the first time, the preparation of the enantiopure P—NH—NH$_2$ ligand by a metal assisted organometallic process via the formation of mer-bis-tridentate iron(II) dichloride complex.

Mechanistic studies have shown that the catalysis begins with the formation of neutral amido-(ene-amido) iron intermediate [Fe(CO)(Ph$_2$PCH=CH—N—((S,S)—C(Ph)H—C (Ph)H)—N—CH$_2$CH$_2$PPh$_2$)] ((S,S)-2), which could be the active catalyst and dehydrogenates isopropanol to form the amine iron hydride species trans-[FeH(CO) (Ph$_2$PCH=CH—N—((S,S)—C(Ph)H—C(Ph)H)—NH— CH$_2$CH$_2$PPh$_2$)] ((S,S)-3). The subsequent transfer of a hydride from the iron and a proton from the amine on (S,S)-3 to the carbonyl of the ketone affords the chiral alcohol product with recovery of (S,S)-2. DFT calculations have revealed very low activation free energies for these transformations and this was the second and more importantly, the likely reason for the highly catalytic activity of the current catalyst system.

Base was found to be important for the efficient catalysis. First, 2 equiv of strong base are required for the irreversible elimination of HCl and HBF$_4$ from the precatalyst to form the active amido-(ene-amido) neutral iron complex (S,S)-2. Another important role of the base was to inhibit the catalyst deactivation by disfavouring the protonation of the ene-amido moiety in (S,S)-2 which otherwise would lead to the inactive species. However, the presence of excess base would racemize of the initial alcohol product, thus decreasing the enantioselectivity of the catalytic system. Furthermore, by modifying the catalytic reaction procedure, full conversion of the substrates without significant deterioration of the enantiomeric purity could be achieved for the present transfer hydrogenation catalyst system. This advance results from the combination of fast hydrogenation step and slow reverse racemization reaction of our catalyst.

All publications, patents and patent applications mentioned in this Specification are indicative of the level of skill of those skilled in the art to which this invention pertains and are herein incorporated by reference to the same extent as if each individual publication, patent, or patent application was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A complex of formula (I)

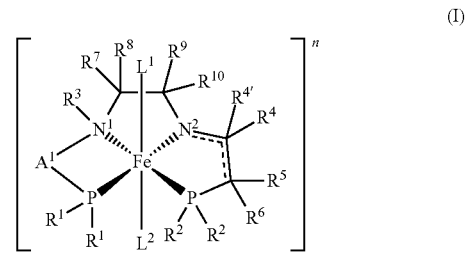

wherein:

$N^1$ and $N^2$ are nitrogen atoms;

$A^1$ is $C_{1-4}$ alkylene, optionally as part of a five or six-membered ring, or ortho-benzylene optionally as part of a six-membered ring, each of which may be optionally substituted by one or more of $C_1$-$C_{20}$ alkyl, $C_1$-$C_6$ alkoxy, halogen, or amine, wherein the five or six membered ring optionally comprises one or more heteroatom;

each $R^1$ and $R^2$ is independently $C_1$-$C_8$ alkyl, $C_2$-$C_8$ alkenyl, $C_1$-$C_8$ alkoxy, aryloxy, $C_3$-$C_8$ cycloalkyl, aryl or heteroaryl, all of which may be optionally substituted, or both $R^1$ substituents combine to form an optionally substituted $C_2$-$C_4$ linear or $C_3$-$C_8$ branched alkylene, or form a ring together with the phosphorus atom to which they are attached, and/or both $R^2$ substituents combine to form an optionally substituted $C_2$-$C_4$ linear or $C_3$-$C_8$ branched alkylene, or form a ring together with the phosphorus atom to which they are attached;

$R^3$ is H or absent;

$R^4$, $R^5$ and $R^8$ are each independently H, or $C_1$-$C_8$ alkyl, $C_2$-$C_8$ alkenyl, aryl, or cycloalkyl, each of which may be optionally substituted;

$R^{4'}$ is H or absent;

$R^6$ is H or absent;

$R^7$, $R^9$ and $R^{10}$ are each independently H, $NH_2$, or $C_1$-$C_8$ alkyl, $C_2$-$C_8$ alkenyl, aryl, or cycloalkyl, each of which may be optionally substituted, or $R^7$ and $R^9$ together with the carbon atoms to which they are attached form an optionally substituted $C_{5-8}$ cycloalkyl ring, or $R^9$ and $R^{10}$ together with the carbon atom to which they are attached form a carbonyl group;

$L^1$ is CO, CNR, CN$^-$, N-heterocyclic carbene or NO, wherein R is $C_1$-$C_8$ alkyl, linear or branched, optionally substituted with vinyl or triethoxysilane, or aryl which may be optionally substituted with vinyl, triethoxysilane or phosphinate;

$L^2$ is absent or is hydride, optionally substituted pyridine, N-methylacetamide, N-methylformamide, optionally substituted imidazole, halide, or $R^aOH$, $NCR^a$ or $^-OR^a$, wherein $R^a$ is aryl, heteroaryl, $C_1$-$C_8$ alkyl, $C_2$-$C_8$ alkenyl or $C_3$-$C_8$ cycloalkyl, all of which may be optionally substituted, or $R^b{}_3N$ wherein each $R^b$ is independently H, methyl or ethyl, or $R^c(CO)R^c$ wherein each $R^c$ is independently $C_1$-$C_8$ alkyl, aryl, or heteroaryl;

n is 0, +1, or +2, wherein when n is +1 or +2, the complex further comprises at least one non-coordinating anion Y, wherein the total charge of all non-coordinating anions in the complex is equal to −n; and each dashed line is either present and denotes the presence of one bond of a double bond or is absent; and wherein the ligand of complex (1) is an unsymmetrical (P—N$^1$—N$^2$—P) ligand.

2. The complex of claim 1, wherein $R^3$ is H and $L^2$ is hydride, optionally substituted pyridine, N-methylacetamide, N-methylformamide, optionally substituted imidazole, halide, or $R^aOH$, $NCR^a$, $^-OR^a$, $R^b{}_3N$, or $R^c(CO)R^c$.

3. The complex of claim 1, wherein $R^{4'}$ is H.

4. The complex of claim 1, which has the structure of formula (Ia), formula (Ib), formula (II), formula (III), or formula (IV)

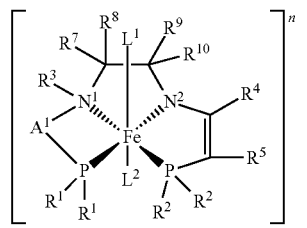
(Ia)

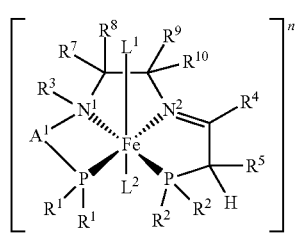
(Ib)

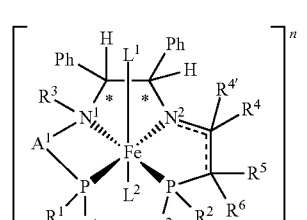
(II)

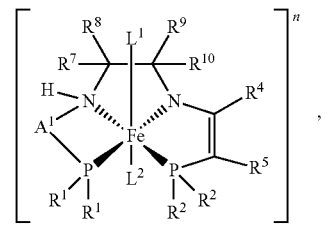
(III)

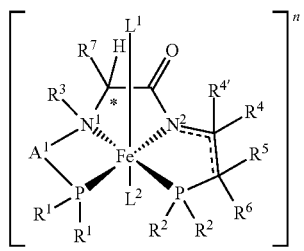
(IV)

5. The complex of claim 1, which comprises at least one non-coordinating anion Y.

6. The complex of claim 1, wherein $A^1$ is

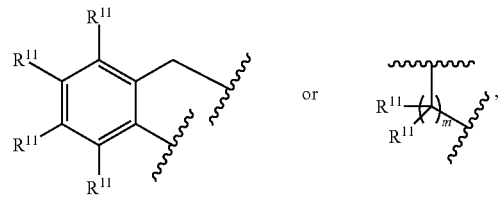

wherein
each $R^{11}$ is independently H, or optionally substituted $C_1$-$C_8$ alkyl, $C_2$-$C_8$ alkenyl, aryl, cycloalkyl, sulfonato, nitro, amino, alkoxy, carboxy, or carboxylato; and
m is 1, 2, or 3.

7. The complex of claim 1, wherein $R^7$ is H, methyl, NH$_2$, —CH$_2$CONH$_2$, —CH$_2$COOH, —CH$_2$SH, —CH$_2$CH$_2$COOH, —CH$_2$CH$_2$CONH$_2$, —CH$_2$(CH$_3$)$_2$, —CH$_2$CH(CH$_3$)$_2$, —CHCH$_3$CH$_2$CH$_3$, —(CH$_2$)NH$_2$, —CH$_2$Ph, —CH$_2$-p-PhOH, —CH$_2$CH$_2$SCH$_3$, —CH$_2$OH, —CHOHCH$_3$, optionally substituted aryl,

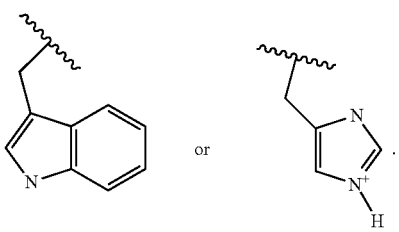 [SMILES: *Cc1c[nH]c2ccccc12 ; *Cc1c[nH+]c[nH]1]

8. The complex of claim 1, wherein the complex is chiral.

9. The complex of claim 4, wherein the complex has the structure of formula (Ia), formula (Ib), formula (II), or formula (III) and has (R,R) or (S,S) stereochemistry or the complex has the structure of formula (IV) and has (R) or (S) stereochemistry.

10. The complex of claim 5, wherein n is +1 or +2 and Y is BF$_4^-$, PF$_6^-$, SbF$_6^-$, ClO$_4^-$, CH$_3$SO$_3^-$, CF$_3$SO$_3^-$, C$_6$H$_5$SO$_3^-$, p-CH$_3$C$_6$H$_4$SO$_3^-$, FeCl$_4^{2-}$, FeBr$_4^{2-}$, phosphates, carboranes, or $B(R^d)_4^-$ or $Al(R^d)_4^-$, wherein each $R^d$ is independently an optionally substituted $C_1$-$C_6$ alkyl, aryl, phenyl, $C_6H_3(CF_3)_2$ and $C_6F_5$, halogen, pseudohalogen, $C_1$-$C_8$ alkoxide, or aryloxide.

11. The complex of claim 1, wherein Y is $BPh_4^-$.

12. The complex of claim 1 having the structure:

[chemical structure] (S,S)-1 [BPh₄],

[chemical structure] (S,S)-1-Br [BPh₄],

[chemical structure] (S,S)-4 [BPh₄],

[chemical structure] (R,R)-9 [BPh₄]

[chemical structure] 20 [BPh₄]

[chemical structure] (S,S)-1tol BF₄,

[chemical structure] (S,S)-1-bis-tol BPh₄ or any diastereomer thereof.

13. A method for transfer hydrogenation of a substrate comprising the step of contacting a substrate with a complex of claim 1.

14. The method of claim 13, wherein the complex is chiral and the transfer hydrogenation is an asymmetric transfer hydrogenation.

15. The method of claim 13, wherein the substrate is a ketone, aldehyde, or imine.

16. The method of claim 13, wherein the transfer hydrogenation is a two-phase system.

17. A method for hydrogenation of a substrate comprising the step of contacting the substrate with a hydrogen source in the presence of a complex of claim 1.

18. The method of claim 17, wherein the substrate is a ketone, aldehyde, imine, ester, amide, or epoxide.

19. The method of claim 17 wherein the hydrogen source is a primary or secondary alcohol, a boron or aluminum hydride compound, a formate salt or other organic hydride source.

20. The method of claim 19, wherein the hydrogen source is isopropanol.

21. A composition comprising:
(a) The complex of claim 1; and
(b) a substrate; a hydrogen source; at least one additive, promoter, or additional catalyst; or any combination thereof.

22. The composition of claim 21, wherein the substrate is a ketone, aldehyde, imine, ester, amide, or epoxide.

23. The composition of claim 21 wherein the hydrogen source is a primary or secondary alcohol, a boron or aluminum hydride compound, a formate salt or other organic hydride source.

24. The composition of claim 23, wherein the hydrogen source is isopropanol.

25. A composition comprising the complex of claim 1 bound to, or immobilized on, a support structure.

26. The composition of claim 25, wherein the support structure is a polymeric support, metal support or silica support.

27. A process for the preparation of the complex of formula (I)

[chemical structure] (I)

wherein:

N¹ and N² are nitrogen atoms;

A¹ is $C_{1-4}$ alkylene, optionally as part of a five or six-membered ring, or ortho-benzylene optionally as part of a six-membered ring, each of which may be optionally substituted by one or more of $C_1$-$C_{20}$ alkyl, $C_1$-$C_6$ alkoxy, halogen, or amine, wherein the five or six membered ring optionally comprises one or more heteroatom;

each $R^1$ and $R^2$ is independently $C_1$-$C_8$ alkyl, $C_2$-$C_8$ alkenyl, $C_1$-$C_8$ alkoxy, aryloxy, $C_3$-$C_8$ cycloalkyl, aryl or heteroaryl, all of which may be optionally substituted, or both $R^1$ substituents combine to form an optionally substituted $C_2$-$C_4$ linear or $C_3$-$C_8$ branched alkylene, or form a ring together with the phosphorus atom to which they are attached, and/or both $R^2$ substituents combine to form an optionally substituted $C_2$-$C_4$ linear or $C_3$-$C_8$ branched alkylene, or form a ring together with the phosphorus atom to which they are attached;

$R^3$ is H or absent;

$R^4$, $R^5$ and $R^8$ are each independently H, or $C_1$-$C_8$ alkyl, $C_2$-$C_8$ alkenyl, aryl, or cycloalkyl, each of which may be optionally substituted;

$R^{4'}$ is H or absent;

$R^6$ is H or absent;

$R^7$, $R^9$ and $R^{10}$ are each independently H, or $C_1$-$C_8$ alkyl, $C_2$-$C_8$ alkenyl, amino, amido, thio, aryl, or cycloalkyl, each of which may be optionally substituted, or $R^7$ and $R^9$ together with the carbon atoms to which they are attached form an optionally substituted $C_{5-8}$ cycloalkyl ring, or $R^9$ and $R^{10}$ together with the carbon atom to which they are attached form a carbonyl group;

$L^1$ is CO, CNR, CN⁻, N-heterocyclic carbene or NO, wherein R is $C_1$-$C_8$ alkyl, linear or branched, optionally substituted with vinyl or triethoxysilane, or aryl, all of which may be optionally substituted with vinyl, triethoxysilane or phosphinate;

$L^2$ is absent or is hydride, optionally substituted pyridine, N-methylacetamide, N-methylformamide, optionally substituted imidazole, halide, or $R^aOH$, $NCR^a$ or $^-OR^a$, wherein $R^a$ is aryl, heteroaryl, $C_1$-$C_8$ alkyl, $C_2$-$C_8$ alkenyl or $C_3$-$C_8$ cycloalkyl, all of which may be optionally substituted, or $R^b{}_3N$ wherein each $R^b$ is independently H, methyl or ethyl, or $R^c(CO)R^c$ wherein each $R^c$ is independently $C_1$-$C_8$ alkyl, aryl, or heteroaryl;

n is 0, +1, or +2, wherein when n is +1 or +2, the complex further comprises at least one non-coordinating anion Y, wherein the total charge of all non-coordinating anions in the complex is equal to −n; and each dashed line is either present and denotes the presence of one bond of a double bond or is absent;

wherein the ligand of complex (1) is an unsymmetrical (P—N¹—N²—P) ligand;

the process comprising the step of reducing one imine group in a diimine complex of formula (X)

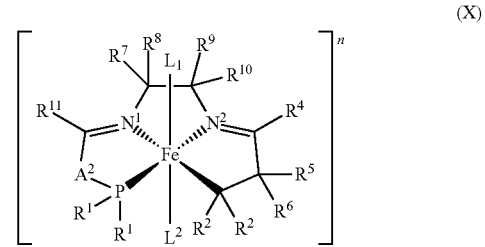

(X)

where $N^1$, $N^2$, $L^1$, $L^2$, n, and substituents $R^1$, $R^2$ and $R^4$-$R^{10}$ are the same as defined above, $R^{11}$ is H, or optionally substituted $C_1$-$C_8$ alkyl, $C_2$-$C_8$ alkenyl, aryl, cycloalkyl, sulfonato, nitro, amino, alkoxy, carboxy, or carboxylato, and $A^2$ is $C_{1-3}$ alkylene, optionally as part of a five or six-membered ring together with $R^{11}$ and the carbon to which it is attached, or ortho-benzylene optionally as part of a six-membered ring, each of which may be optionally substituted by one or more of $C_1$-$C_{20}$ alkyl, $C_1$-$C_6$ alkoxy, halogen, or amine, wherein the five or six membered ring optionally comprises one or more heteroatom, and wherein, in the complex of formula (I), $R^3$ is H and $A^1$ is $A^2$-$CHR^{11}$—.

28. The process of claim 27, wherein the complex of formula (X) is first treated with a hydride reductant and then with an acid.

29. The process of claim 28, wherein the hydride reductant is a mixture of a primary or secondary alcohol with a base.

30. The process of claim 29, wherein the base is an amine, phosphazene, amide, alkoxide, hydroxide or hydride salt.

31. The process of claim 29, wherein the hydride reductant is isopropoxide, a boron or aluminum hydride compound, a formate salt or other organic hydride source.

32. A process for the preparation of the complex of claim 4 having the structure of formula (Ia), the process comprising the step of converting the dienamido complex of Formula (XI) to the complex of formula (Ia)

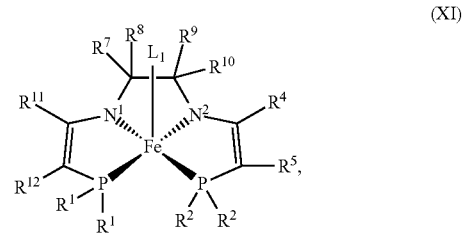

(XI)

$N^1$ and $N^2$ are nitrogen atoms;

each $R^1$ and $R^2$ is independently $C_1$-$C_8$ alkyl, $C_1$Chd 8 alkenyl, $C_1$-$C_8$ alkoxy, aryloxy, $C_3$-$C_8$ cycloalkyl, aryl or heteroaryl, all of which may be optionally substituted, or both $R^1$ substituents combine to form an optionally substituted $C_2$-$C_4$ linear or $C_3$-$C_8$ branched alkylene, or form a ring together with the phosphorus atom to which they are attached, and/or both $R^2$ substituents combine to form an optionally substituted $C_2$-$C_4$ linear or $C_3$-$C_8$ branched alkylene, or form a ring together with the phosphorus atom to which they are attached;

$R^4$, $R^5$ and $R^8$ are each independently H, or $C_1$-$C_8$ alkyl, $C_2$-$C_8$ alkenyl, aryl, or cycloalkyl, each of which may be optionally substituted;

$R^7$, $R^9$ and $R^{10}$ are each independently H, $NH_2$, or $C_1$-$C_8$ alkyl, $C_2$-$C_8$ alkenyl, aryl, or cycloalkyl, each of which may be optionally substituted, or $R^7$ and $R^9$ together with the carbon atoms to which they are attached form an optionally substituted $C_{5-8}$ cycloalkyl ring, or $R^9$ and $R^{10}$ together with the carbon atom to which they are attached form a carbonyl group;

$L^1$ is CO, CNR, $CN^-$, N-heterocyclic carbene or NO, wherein R is $C_1$-$C_8$ alkyl, linear or branched, optionally substituted with vinyl or triethoxysilane, or aryl which may be optionally substituted with vinyl, triethoxysilane or phosphinate;

$R^{11}$ and $R^{12}$ are each independently H, or optionally substituted $C_1$-$C_8$ alkyl, $C_2$-$C_8$ alkenyl, aryl, cycloalkyl, sulfonato, nitro, amino, alkoxy, carboxy, or carboxylato, or $R^{11}$ and $R^{12}$, together with the carbons to which they are attached, form a five or six membered ring that is optionally substituted by one or more of $C_1$-$C_{10}$ alkyl, $C_1$-$C_6$ alkoxy, halogen, or amine, wherein the five or six membered ring optionally comprises one or more heteroatom, and wherein, in the complex of formula (Ia), $L^2$, $R^3$, $R^6$ and $R^{4'}$ are absent and where $A^1$ is —$CHR^{12}CHR^{11}$—.

33. The process of claim 32, wherein the complex of formula (XI) is:
(a) first treated with a weak acid and then treated with a hydride source; or
(b) treated with a reagent that functions as an acid and a hydride source.

34. The process of claim 33, wherein the reagent that functions as an acid and a hydride source is isopropanol.

35. A process for the preparation of the complex of claim 1, the process comprising the step of reacting a phosphonium dimer of Formula (VI) with a PNN proligand of Formula (V) and an iron complex in the presence of a base

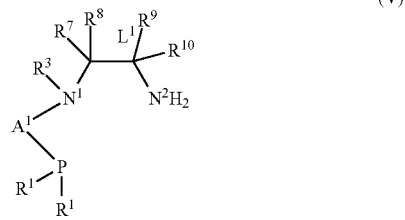

(V)

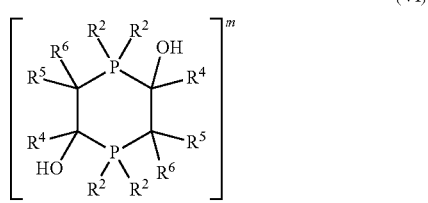

(VI)

where
$N^1$ and $N^2$ are nitrogen atoms;
$A^1$ is $C_{1-4}$alkylene, optionally as part of a five or six-membered ring, or ortho-benzylene optionally as part of a six-membered ring, each of which may be optionally substituted by one or more of $C_1$-$C_{20}$ alkyl, $C_1$-$C_6$alkoxy, halogen, or amine, wherein the five or six membered ring optionally comprises one or more heteroatom;

each $R^1$ and $R^2$ is independently $C_1$-$C_8$ alkyl, $C_2$-$C_8$ alkenyl, $C_1$-$C_8$ alkoxy, aryloxy, $C_3$-$C_8$ cycloalkyl, aryl or heteroaryl, all of which may be optionally substituted, or both $R^1$ substituents combine to form an optionally substituted $C_2$-$C_4$ linear or $C_3$-$C_8$ branched alkylene, or form a ring together with the phosphorus atom to which they are attached, and/or both $R^2$ substituents combine to form an optionally substituted $C_2$-$C_4$ linear or $C_3$-$C_8$ branched alkylene, or form a ring together with the phosphorus atom to which they are attached;

$R^3$ is H or absent;

$R^4$, $R^5$ and $R^8$ are each independently H, or $C_1$-$C_8$ alkyl, $C_2$-$C_8$ alkenyl, aryl, or cycloalkyl, each of which may be optionally substituted;

$R^6$ is H or absent;

$R^7$, $R^9$ and $R^{10}$ are each independently H, $NH_2$, or $C_1$-$C_8$ alkyl, $C_2$-$C_8$ alkenyl, aryl, or cycloalkyl, each of which may be optionally substituted, or $R^7$ and $R^9$ together with the carbon atoms to which they are attached form an optionally substituted $C_{5-8}$ cycloalkyl ring, or $R^9$ and $R^{10}$ together with the carbon atom to which they are attached form a carbonyl group; and wherein m is +2.

36. The process of claim 35, wherein the iron complex is $[Fe(H_2O)]_6[BF_4]_2$ or another ferrous salt.

37. The process of claim 35, which comprises a subsequent step of reacting the product of the reaction of the phosphonium dimer, the PNN proligand and the iron complex with a ligand $L^1$ and, optionally, a salt of ligand $L^2$, wherein $L^1$ is CO, CNR, $CN^-$, N-heterocyclic carbene or NO, wherein R is $C^1$-$C^8$ alkyl, linear or branched, optionally substituted with vinyl or triethoxysilane, or aryl which may be optionally substituted with vinyl, triethoxysilane or phosphinate; and $L^2$ is absent or is hydride, optionally substituted pyridine, N-methylacetamide, N-methylformamide, optionally substituted imidazole, halide, or $R^aOH$, $NCR^a$ or $OR^a$, wherein $R^a$ is aryl, heteroaryl, $C_1$-$C_8$ alkyl, $C_2$-$C_8$ alkenyl or $C_3$-$C_8$ cycloalkyl, all of which may be optionally substituted, or $R^b{}_3N$ wherein each $R^b$, is independently H, methyl or ethyl, or $R^c(CO)R^c$ wherein each $R^c$ is independently $C_1$-$C_8$ alkyl, aryl, or heteroaryl.

* * * * *

UNITED STATES PATENT AND TRADEMARK OFFICE
CERTIFICATE OF CORRECTION

PATENT NO. : 9,597,673 B2  
APPLICATION NO. : 14/403770  
DATED : March 21, 2017  
INVENTOR(S) : Alexandre Mikhailine et al.

Page 1 of 1

It is certified that error appears in the above-identified patent and that said Letters Patent is hereby corrected as shown below:

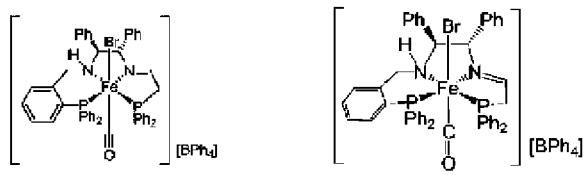

At Column 67 Lines 35-40 (Claim 12), replace " (S,S)-I " with -- (S, S)-I --.

At Column 67 Lines 50-55, and at Column 67 Lines 60-65, add -- , -- between structures.

At Column 70 Line 56 (Claim 32), replace "C₁Chd 8" with -- $C_2$-$C_8$ --.

Signed and Sealed this  
Fifteenth Day of August, 2017

Joseph Matal  
*Performing the Functions and Duties of the*  
*Under Secretary of Commerce for Intellectual Property and*  
*Director of the United States Patent and Trademark Office*